(12) United States Patent
Watanabe et al.

(10) Patent No.: US 10,505,116 B2
(45) Date of Patent: Dec. 10, 2019

(54) ORGANIC ELECTROLUMINESCENT ELEMENT AND COMPOUND

(75) Inventors: Kousuke Watanabe, Kanagawa (JP); Wataru Sotoyama, Kanagawa (JP)

(73) Assignee: UDC IRELAND LIMITED, Dublin (IE)

( * ) Notice: Subject to any disclaimer, the term of this patent is extended or adjusted under 35 U.S.C. 154(b) by 859 days.

(21) Appl. No.: 13/812,785

(22) PCT Filed: Jul. 20, 2011

(86) PCT No.: PCT/JP2011/066474
§ 371 (c)(1),
(2), (4) Date: Jul. 1, 2013

(87) PCT Pub. No.: WO2012/014752
PCT Pub. Date: Feb. 2, 2012

(65) Prior Publication Data
US 2013/0320312 A1 Dec. 5, 2013

(30) Foreign Application Priority Data

Jul. 30, 2010 (JP) ................................. 2010-173184

(51) Int. Cl.
| | | |
|---|---|---|
| *H01L 51/50* | (2006.01) | |
| *H01L 51/00* | (2006.01) | |
| *C07D 215/04* | (2006.01) | |
| *C07D 307/91* | (2006.01) | |
| *C07D 333/76* | (2006.01) | |
| *C09K 11/06* | (2006.01) | |
| *H05B 33/14* | (2006.01) | |
| *C09B 57/00* | (2006.01) | |

(52) U.S. Cl.
CPC ........ *H01L 51/0052* (2013.01); *C07D 215/04* (2013.01); *C07D 307/91* (2013.01); *C07D 333/76* (2013.01); *C09B 57/00* (2013.01); *C09K 11/06* (2013.01); *H01L 51/0074* (2013.01); *H01L 51/5016* (2013.01); *H01L 51/5048* (2013.01); *H05B 33/14* (2013.01); *C09K 2211/1007* (2013.01); *C09K 2211/1011* (2013.01); *C09K 2211/1029* (2013.01); *C09K 2211/1044* (2013.01); *C09K 2211/1059* (2013.01); *C09K 2211/1088* (2013.01); *C09K 2211/1092* (2013.01); *H01L 51/0054* (2013.01); *H01L 51/0072* (2013.01); *H01L 51/0073* (2013.01); *H01L 51/0085* (2013.01)

(58) Field of Classification Search
CPC ............ C09K 11/06; C09K 2211/1007; C09K 2211/1011; C09K 2211/1018; C09K 2211/1025; C09K 2211/1029; C09K 2211/1044; C09K 2211/1059; C09K 2211/1088; C09K 2211/1092; C07D 215/04; C07D 307/91; C07D 333/76; H05B 33/14; H01L 51/0032; H01L 51/005; H01L 51/0052; H01L 51/0058; H01L 51/0062; H01L 51/0065; H01L 51/0068; H01L 51/0071; H01L 51/0074; H01L 51/0072; H01L 51/0073; H01L 51/0085; H01L 51/50; H01L 51/5016; H01L 51/5012; H01L 51/5048; H01L 51/5056; H01L 51/5088; H01L 51/5096
USPC ............ 257/40, 88–104, E51.001–E51.052; 428/690, 691, 917; 427/58, 66; 252/301.16–301.35; 313/500–512
See application file for complete search history.

(56) References Cited

U.S. PATENT DOCUMENTS

| | | | | |
|---|---|---|---|---|
| 2005/0064235 A1* | 3/2005 | Liao | ................... | H01L 51/5012 428/690 |
| 2006/0088728 A1* | 4/2006 | Kwong | ................ | C07D 209/82 428/690 |
| 2007/0141387 A1* | 6/2007 | Nakano | .................. | C09K 11/06 428/690 |
| 2007/0196691 A1 | 8/2007 | Ikemizu et al. | | |
| 2008/0315754 A1* | 12/2008 | Kawamura | .......... | C07D 307/79 313/504 |
| 2009/0131673 A1* | 5/2009 | Tanabe | ................. | C07D 307/91 546/88 |
| 2010/0038634 A1* | 2/2010 | Nagao | ................. | C07D 307/91 257/40 |

FOREIGN PATENT DOCUMENTS

| | | | | |
|---|---|---|---|---|
| JP | 2007077094 | 3/2007 | | |
| JP | 2007238500 | 9/2007 | | |
| JP | 2008545729 | 12/2008 | | |
| JP | 2009246354 A | * 10/2009 | ........ | H01L 51/0054 |
| JP | 2009249378 | 10/2009 | | |
| WO | 2007069569 | 6/2007 | | |
| WO | 2009021126 | 3/2009 | | |
| WO | WO-2010114256 A2 | * 10/2010 | ............ | C07C 15/30 |

OTHER PUBLICATIONS

Nagao et al., JP 2009-246354 A—Machine translation, Oct. 2009, pp. 1-39.*

* cited by examiner

*Primary Examiner* — Andrew K Bohaty
*Assistant Examiner* — Dylan C Kershner
(74) *Attorney, Agent, or Firm* — Riverside Law LLP

(57) ABSTRACT

[Disclosed is] a high-efficiency and durable organic electroluminescent element having a low drive voltage, being an organic electroluminescent element having on a substrate a pair of electrodes comprising an anode and a cathode and at least one organic layer including a light-emitting layer between these electrodes, with this organic electroluminescent element containing a specific compound having a dibenzothiophene or dibenzofuran structure and a phenanthrene structure in at least one layer out of the aforementioned at least one organic layer. [Also disclosed is] this specific compound.

13 Claims, 2 Drawing Sheets

ORGANIC ELECTROLUMINESCENT ELEMENT AND COMPOUND

CROSS-REFERENCE TO RELATED APPLICATIONS

The present application is a U.S. National Stage Entry of International Patent Application No. PCT/JP2011/066474, filed 20 Jul. 2011, which in turn claims priority benefit from Japanese Patent Application No. 2010-173184, filed 30 Jul. 2010, all of which are hereby incorporated by reference herein in their entirety.

TECHNICAL FIELD

The present invention relates to an organic electroluminescent element and a compound used in this element.

BACKGROUND ART

Organic electroluminescent elements (hereinafter also referred to as "elements" or "organic EL elements") emit light at high brightness and at a low drive voltage and have therefore been the subject of active research and development. An organic electroluminescent element has an organic layer between a pair of electrodes. Electrons injected from the cathode and holes injected from the anode are rebound at the organic layer, and the energy of the excitons thus produced is utilized to emit light.

Patent Document 1 discloses that a specific compound having a benzothiophene structure or a benzofuran structure is effective in providing an organic EL element that has excellent luminous efficiency, low pixel defects, excellent heat resistance, and a long service life.

Furthermore, Patent Document 2 discloses a compound having a benzothiophene structure in which a triphenylene group has been substituted, as being particularly effective as a host material for an organic EL element.

RELATED ART DOCUMENTS

Patent Documents

Patent Document 1: WO 07/069569
Patent Document 2: WO 09/021126

SUMMARY OF THE INVENTION

Problems to be Solved by the Invention

An organic electroluminescent element needs to have excellent efficiency and durability, as well as being capable of being driven at a low voltage, and there is a need for an element in which these characteristics are even better.

None of the elements featuring comparative compounds 1 to 4, etc., given in the working examples which will be described later was satisfactory in terms of efficiency, drive voltage, and so forth.

Specifically, it is an object of the present invention to provide an organic electroluminescent element that is satisfactory at a high level in terms of high efficiency, high durability, and reduced drive voltage.

Moreover, it is another Object of the present invention to provide a compound that is useful in an organic electroluminescent element as a host material, an electron transport material, or the like, in addition, it is yet another object of the present invention to provide a light-emitting device, a display device, and a lighting device that include the organic electroluminescent element of the present invention.

Means for Solving the Problems

Study by the inventors has revealed that an organic electroluminescent element which is satisfactory at a high level in terms of high efficiency, high durability, and reduced drive voltage can be provided by using a compound having a structure in which dibenzothiophene or dibenzofuran is bound to phenanthrene via an arylene. The source of the high efficiency is surmised to be that there is plenty of triplet energy for a light-emitting material and that energy transfer quenching in the material of a hole transport layer is suppressed. The source of high durability is surmised to be that the introduction of a phenanthrene structure improves stability with respect to radical anions of the molecule. The source of the reduction in drive voltage is surmised to be the high charge transferability of the dibenzothiophene structure and the phenanthrene structure.

Specifically, the present invention can be achieved by the following means:

1.

An organic electroluminescent element having on a substrate a pair of electrodes comprising an anode and a cathode and at least one organic layer including a light-emitting layer between these electrodes, wherein at least one layer out of the aforementioned at least one organic layer contains at least one type of compound expressed by General Formula 1[1] below:

[1] Translator's note: In the Japanese original document, the labeling number for each of the general formulas is indicated in parentheses, but we have omitted the parentheses in the translation to avoid nested parentheses and confusion with other parenthetical notations.

[First Chemical Formula]

General Formula 1

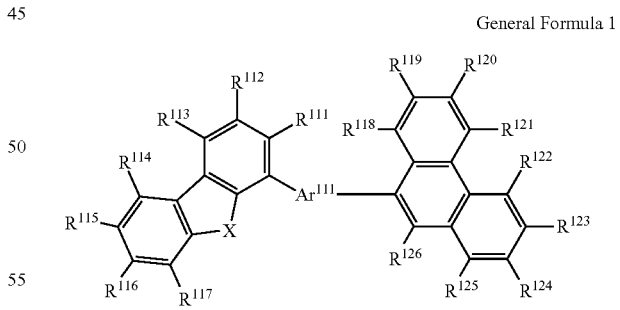

(in General Formula 1, X represents an oxygen atom or a sulfur atom, $R^{111}$ to $R^{126}$ represent each independently a hydrogen atom or a substituent, and $Ar^{111}$ represents an arylene group).

2.

The organic electroluminescent element according to 1 above, wherein the compound expressed by General Formula 1 above is a compound expressed by General Formula 3 below:

[Second Chemical Formula]

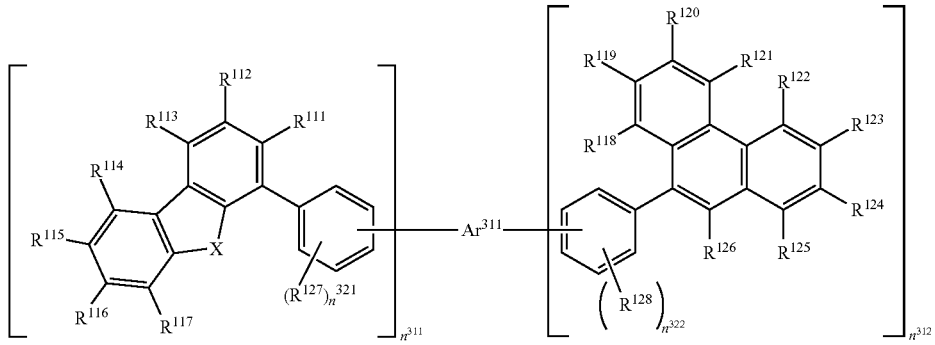

General Formula 3

(in General Formula 3, X represents an oxygen atom or a sulfur atom, $R^{111}$ to $R^{126}$ represent each independently a hydrogen atom or a substituent, $R^{127}$ and $R^{128}$ represent each independently a substituent, $n^{311}$ and $n^{312}$ represent each independently 1 or 2, $n^{321}$ and $n^{322}$ represent each independently an integer from 0 to 4, and $Ar^{311}$ represents a single bond or an aromatic group of $n^{311}+n^{312}$ valence).

3.

The organic electroluminescent element according to 1 or 2 above, wherein the aforementioned light-emitting layer contains a compound expressed by either General Formula 1 or 3 above.

4.

The organic electroluminescent element according to any one of 1 to 3 above, wherein the aforementioned light-emitting layer contains an iridium complex.

5.

The organic electroluminescent element according to any one of 1 to 4 above, wherein the aforementioned light-emitting layer contains an iridium complex expressed by General Formula T-1 below:

[Third Chemical Formula]

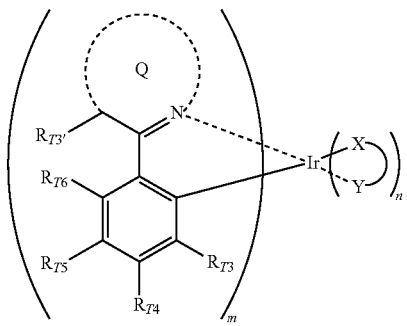

(T-1)

(In General Formula T-1. $R_{T3}'$, $R_{T3}$, $R_{T4}$, $R_{T5}$, and $R_{T6}$ represent each independently a hydrogen atom or a substituent;

any adjacent two of $R_{T3}$, $R_{T4}$, $R_{T5}$, and $R_{T6}$ may bind together to form a condensed four- to seven-member ring, this condensed four- to seven-member ring is a cycloalkyl, an aryl, or a heteroaryl, and this condensed four- to seven-member ring may further have a substituent;

$R_{T3}'$ and $R_{T6}$ may form a ring by being linked by a linking group selected from among —C($R_T$)$_2$—C($R_T$)$_2$—, —C$R_T$=C$R_T$—, —C($R_T$)$_2$—, —O—, —N$R_T$—, —O—C($R_T$)$_2$—, —N$R_T$—C($R_T$)$_2$—, and —N=C$R_T$—, and the $R_T$ [groups] represent each independently a hydrogen atom, an alkyl group, an alkenyl group, an alkynyl group, an aryl group, or a heteroaryl group, and may further have a substituent;

the ring Q is a five- or six-member aromatic heterocycle or condensed aromatic heterocycle including at least one nitrogen; and (X—Y) represents an auxiliary ligand, m represents an integer of 1 to 3, n represents an integer of 0 to 2, and m+n=3).

6.

The organic electroluminescent element according to any one of 1 to 5 above, wherein there is an electron transport layer between the aforementioned light-emitting layer and the aforementioned cathode, there is an intermediate layer between this electron transport layer and the aforementioned light-emitting layer, and this intermediate layer contains a compound expressed by General Formula 1 or 3 above.

7.

A compound expressed by General Formula 3:

[Fourth Chemical Formula]

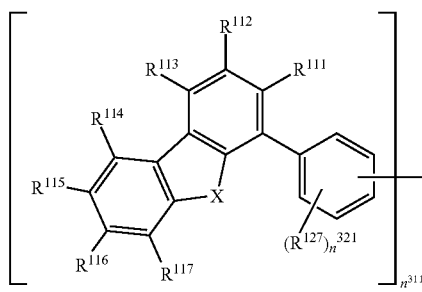 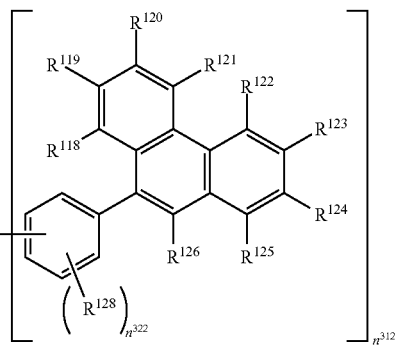

General Formula 3

(in General Formula 3, X represents an oxygen atom or a sulfur atom, $R^{111}$ to $R^{126}$ represent each independently a hydrogen atom or a substituent, $R^{127}$ and $R^{128}$ represent each independently a substituent, $n^{311}$ and $n^{312}$ each independently 1 or 2, $n^{321}$ and $n^{322}$ represent each independently an integer from 0 to 4, and $Ar^{311}$ represents a single bond or an aromatic group of valence).

8.

A composition, containing the compound expressed by General Formula 1 or 3 above according to any one of 1 to 7 above.

9.

A thin film, containing the compound expressed by General Formula 1 or 3 above according to any one of 1 to 7 above.

10.

A light-emitting device featuring the organic electroluminescent element according to any one of 1 to 6 above.

11.

A display device featuring the organic, electroluminescent element according to any one of 1 to 6 above.

12.

A lighting device featuring the organic electroluminescent element according to any one of 1 to 6 above.

Effects of the Invention

With the present invention, it is possible to provide an organic electroluminescent element with high efficiency, high durability, and low drive voltage.

DETAILED DESCRIPTION OF EMBODIMENTS

Figure 1:
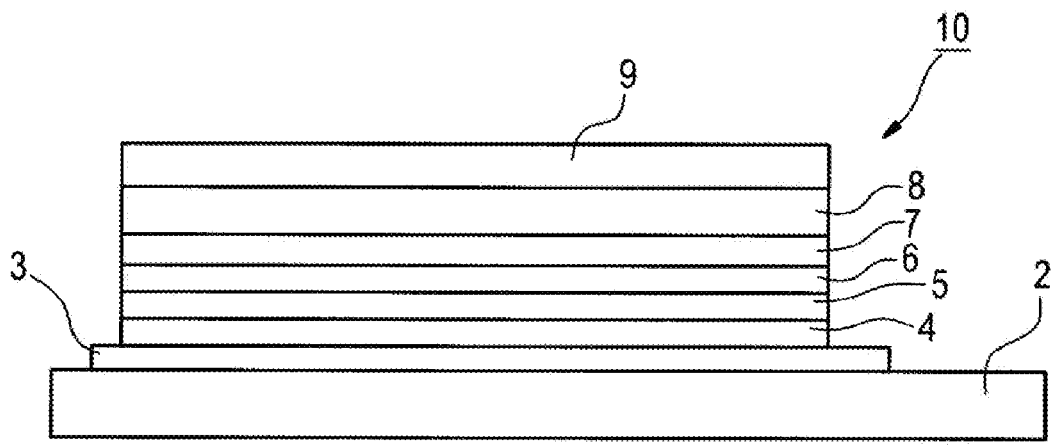
FIG. 1 is a schematic diagram illustrating one example of the configuration of the organic electroluminescent element according to the present invention.

The "hydrogen atom" in the description of General Formulas 1 to 3 below includes isotopes (deuterium atoms, etc.), and the atoms that constitute the substituents also include isotopes thereof.

In the present invention, when the term "substituent" is used, that substituent may be substituted. For example, when "alkyl group" is referred to in the present invention, it encompasses alkyl groups that have been substituted with a fluorine atom (such as a trifluoromethyl group), alkyl groups that have been substituted with an aryl group (such as a triphenylmethyl group), and so forth, and when the term "$C_1$ to $C_6$ alkyl group" is used this indicates that the carbon number is from 1 to 6 for the entire group, including, one that has been substituted.

In the present invention, a Substituent Group A is defined as follows:

(Substituent Group A)

Examples [of Substituent Group A] include alkyl groups (preferably with a carbon number of 1 to 30, more preferably with a carbon number of 1 to 20, and even more preferably with a carbon number of 1 to 10, such as a methyl, ethyl, isopropyl, tert-butyl, neopentyl, n-octyl, n-decyl, n-hexadecyl, cyclopropyl, cyclopentyl, and cyclohexyl); alkenyl groups (preferably with a carbon number of 2 to 30, more preferably with a carbon number of 2 to 20, and even more preferably with a carbon number of 2 to 10, such as a vinyl, allyl, 2-butenyl, and 3-pentenyl); alkynyl groups (preferably with a carbon number of 2 to 30, more preferably with a carbon number of 2 to 20, and even more preferably with a carbon number of 2 to 10, such as propargyl and 3-pentynyl); aryl groups (preferably with a carbon number of 6 to 30, more preferably with a carbon number of 6 to 20, and even more preferably with a carbon number of 6 to 12, such as phenyl, p-methylphenyl, naphthyl, anthracenyl, and phenantryl); amino groups (preferably with a carbon number of 0 to 30, more preferably with a carbon number of 0 to 20, and even more preferably with a carbon number of 0 to 10, such as dimethylamino, diethylamino, dibenzylamino, diphenylamino, and ditolylamino); alkoxy groups (preferably with a carbon number of 1 to 30, more preferably with a carbon number of 1 to 20, and even more preferably with a carbon number of 1 to 10, such as methoxy, ethoxy, butoxy, and 2-ethylhexyloxy); aryloxy groups (preferably with a carbon number of 6 to 30, more preferably with a carbon number of 6 to 20, and even more preferably with a carbon number of 6 to 12, such as phenyloxy, 1-naphthyloxy, and 2-naphthyloxy); heterocyclic oxy groups (preferably with a carbon number of 1 to 30, more preferably with a carbon number of 1 to 20, and even more preferably with a carbon number of 1 to 12, such as pyridyloxy, pyrazyloxy, pyrimidyloxy, and quinolyloxy); acyl groups (preferably with a carbon number of 2 to 30, more preferably with a carbon number of 2 to 20, and even more preferably with a carbon number of 2 to 12, such as acetyl, benzoyl, formyl, and pivaloyl); alkoxycarbonyl groups (preferably with a carbon number of 2 to 30, more preferably with a carbon number of 2 to 20, and even more preferably with a carbon number of 2 to 12, such as methoxycarbonyl and ethoxycarbonyl); aryloxycarbonyl groups (preferably with a carbon number of 7 to 30, more preferably with a carbon number of 7 to 20, and even more preferably with a carbon number of 7 to 12, such as phenyloxycarbonyl); acyloxy groups (preferably with a carbon number of 2 to 30, more preferably with a carbon number of 2 to 20, and even more preferably with a carbon number of 2 to 10, such as acetoxy and benzoyloxy); alkylthio groups (preferably with a carbon number of 1 to 30, more preferably with a carbon number of 1 to 20, and even more preferably with a carbon number of 1 to 12, such as methylthio and ethylthio); arylthio groups (preferably with a carbon number of 6 to 30, more preferably with a carbon number of 6 to 20, and even more preferably with a carbon number of 6 to 12, such as phenylthio); heterocyclic thio groups (preferably with a carbon number of 1 to 30, more preferably with a carbon number of 1 to 20, and even more preferably with a carbon number of 1 to 12, such as pyridylthio, 2-benzimidazolylthio, 2-benzoxazolylthio and 2-benzothiazolylthio); sulfonyl groups (preferably with a carbon number of 1 to 30, more preferably with a carbon number of 1 to 20, and even more preferably with a carbon number of to 12, such as mesyl and tosyl); sulfinyl groups (preferably with a carbon number of 1 to 30, more preferably with a carbon number of 1 to 20, and even more preferably with a carbon number of 1 to 12, such as methanesulfinyl and benzenesulfinyl); halogen atoms (such as a fluorine atom, chlorine atom, bromine atom, and iodine atom); a cyano group; a sulfo group; a carboxyl group; a nitro group; a sulfino group; an imino group; heterocyclic groups (including aromatic heterocyclic groups, preferably with a carbon number of 1 to 30 and more preferably with a carbon number of 1 to 12, with examples of the hetero atom including a nitrogen atom, an oxygen atom, a sulfur atom, a phosphorus atom, a silicon atom, a selenium atom, and a tellurium atom, and with concrete examples including pyridyl, pyrazinyl, pyrimidyl, pyridazinyl, pyrrolyl, pyrazolyl, triazolyl, imidazolyl, oxazolyl, thiazolyl, isoxazolyl, isothiazolyl, quinolyl, furyl, thienyl, selenophenyl, tellurophenyl, piperidyl, piperidino, morpholino, pyrrolidyl, pyrrolidino, benzoxazolyl, benzimidazolyl, benzothiazolyl, a carbazolyl group, azepinyl group, and silolyl group); silyl groups (preferably with a carbon number of 3 to 40, more preferably with a carbon number of 3 to 30, and even more preferably with a carbon number of 3 to 24, such as trimethylsilyl and triphenylsilyl); silyloxy groups (preferably with a carbon number of 3 to 40, more preferably with a carbon number of 3 to 30, and even more preferably with a carbon number of 3 to 24, such as trimethylsilyloxy and triphenylsilyloxy), and phosphoryl groups (such as diphenylphosphoryl and dimethylphosphoryl). These substituents may be further substituted, and examples of the further substituent include groups selected from Substituent Group A described above.

The organic electroluminescent element of the present invention is an organic electroluminescent element which has on a substrate a pair of electrodes comprising an anode and a cathode and at least one organic layer including a light-emitting layer between these electrodes, with at least one layer out of the aforementioned at least one organic layer containing a compound expressed by General Formula 1.

The compound expressed by the General Formula 1 is a compound that has a structure in which dibenzothiophene or dibenzofuran is bound to phenanthrene via an arylene. This structure is surmised to increase electron affinity and to contribute to a decrease in drive voltage. Furthermore, it is preferable to use [this compound] as the material of an intermediate layer between the light-emitting layer and the electron transport layer and as the host material of the light-emitting layer in a green-light-emitting element. Moreover, in a red-light-emitting element, it is preferable to use [this compound] as the host material of the light-emitting layer.

(Compound Expressed by General Formula 1)

[Fifth Chemical Formula]

General Formula 1

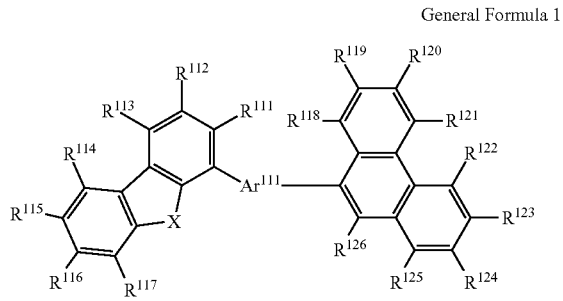

In General Formula 1, X represents an oxygen atom or a sulfur atom, $R^{111}$ to $R^{126}$ represent each independently a hydrogen atom or a substituent, and $Ar^{111}$ represents an arylene group.

X is preferably a sulfur atom.

There are no particular restrictions on the substituents expressed by $R^{111}$ to $R^{112}$, but examples include those substituents listed as examples of the aforementioned Substituent Group A.

$R^{111}$ to $R^{117}$ are preferably each independently a hydrogen atom, an alkyl group, an aryl group, or a cyano group, more preferably a hydrogen atom, an alkyl group, or an aryl group, and even more preferably a hydrogen atom. It is preferable for $R^{111}$ to $R^{117}$ to be hydrogen atoms in terms of contributing to increasing charge transport properties.

The alkyl group expressed by $R^{111}$ to $R^{117}$ is a straight-chain, branched-chain, or cyclic alkyl group, and is preferably a $C_1$ to $C_{18}$ alkyl group, more preferably a $C_1$ to $C_{12}$ alkyl group, and even more preferably a $C_1$ to $C_6$ alkyl group. The alkyl group expressed by $R^{111}$ to $R^{117}$ is particularly preferably a methyl group, ethyl group, n-propyl group, i-propyl group, n-butyl group, t-butyl group, i-butyl group, n-pentyl group, neopentyl group, t-amyl group, s-isoamyl group, cyclopentyl group, n-hexyl group, or cyclohexyl group, and most preferably a methyl group, ethyl group, t-butyl group, or n-pentyl group.

The aryl group expressed by $R^{111}$ to $R^{117}$ preferably has a carbon number of 6 to 30, and more preferably a carbon number of 6 to 20, and even more preferably a carbon number of 6 to 12, examples of which include a phenyl group, p-methylphenyl group, naphthyl group, and anthracenyl group.

In cases where any of $R^{111}$ to $R^{117}$ represents a substituent, it is preferable for $R^{112}$ and $R^{115}$ to $R^{126}$ represent a substituent and for $R^{111}$, $R^{113}$, $R^{114}$, $R^{116}$, and $R^{117}$ to represent a hydrogen atom.

$R^{118}$ to $R^{126}$ represent each independently a hydrogen atom, an alkyl group, an aryl group, or a cyano group, more preferably a hydrogen atom, an aryl group, or a cyano group, and even more preferably a hydrogen atom or an aryl group. A hydrogen atom is preferable in terms of contributing to increasing charge transport properties.

The alkyl group expressed by $R^{118}$ to $R^{126}$ is a straight-chain, branched-chain, or cyclic alkyl group, and is preferably a $C_1$ to $C_{18}$ alkyl group, more preferably a $C_1$ to $C_{12}$ alkyl group, and even more preferably a $C_1$ to $C_6$ alkyl group. The alkyl group expressed by $R^{118}$ to $R^{126}$ is particularly preferably a methyl group, ethyl group, n-propyl group, i-propyl group, n-butyl group, t-butyl group, i-butyl group, n-pentyl group, neopentyl group, t-amyl group, s-isoamyl group, cyclopentyl group, n-hexyl group, or cyclohexyl group, and most preferably a methyl group, i-propyl group, n-butyl group, or t-butyl group.

The aryl group expressed by $R^{118}$ to $R^{126}$ preferably has a carbon number of 6 to 30, more preferably a carbon number of 6 to 20, and even more preferably a carbon number of 6 to 12, examples of which include a phenyl group, p-methylphenyl group, naphthyl group, and anthracenyl group, with a phenyl group being preferable.

The arylene group expressed by $Ar^{111}$ preferably has a larger number of aromatic rings in order to prevent a decrease in efficiency due to high-temperature storage.

Moreover, the aromatic ring included in the arylene group expressed by $Ar^{111}$ is preferably a benzene ring. The arylene group expressed by $Ar^{111}$ is preferably a phenylene group, biphenylene group, terphenylene group, quarter phenylene group, or quinque phenylene group, and more preferably a phenylene group, biphenylene group, or terphenylene group.

The arylene group expressed by $Ar^{111}$ may be substituted with an alkyl group, aryl group, hetero aryl group, cyano group, or other such substituent, with an aryl group, hetero aryl group, or cyano group being preferable as the substituent, and a cyano group being more preferable.

Two or more of the substituents expressed by $R^{111}$ to $R^{117}$ may together form a condensed aromatic ring. An example of the aromatic ring thus formed is a benzene ring, but from the standpoint of luminous efficiency, it is preferable not to form an aromatic ring.

Two or more of the substituents expressed by $R^{118}$ to $R^{126}$ may together form a condensed aromatic ring.

An example of the aromatic ring thus formed is a benzene ring, but from the standpoint of luminous efficiency with a green-light-emitting element, it is preferable not to form an aromatic ring. However, $R^{121}$ and $R^{122}$ never form a condensed aromatic ring.

The substituent expressed by $R^{111}$ to $R^{126}$ may have a further substituent, and examples of further substituents include alkyl groups and aryl groups. The alkyl group serving as a further substituent is defined the same as the alkyl group expressed by $R^{111}$ to $R^{126}$, and preferred examples are also defined the same. The aryl group serving as a further substituent preferably has a carbon number of 6 to 30, more preferably a carbon number of 6 to 20, and even more preferably a carbon number of 6 to 14, and is preferably a phenyl group, naphthyl group, or phenanthryl group, and more preferably a phenyl group.

Note that the substituent expressed by $R^{111}$ to $R^{126}$ may be a group having a phenanthrene structure bound to the $Ar^{111}$ expressed by General Formula 1, and the compound expressed by General Formula 1 can have a plurality of phenanthrene structures, such as from one to three.

Note that when the application is to a green-light-emitting element, in terms of $T_1$ energy, the plurality of benzene rings in the arylene group expressed by $Ar^{111}$ are preferably linked at the meta position (m-) from the standpoint of luminous efficiency in a green-light-emitting element.

$Ar^{111}$ is preferably a linking group expressed by any of General Formulas 1-1 to 13 below,

[Sixth Chemical Formula]

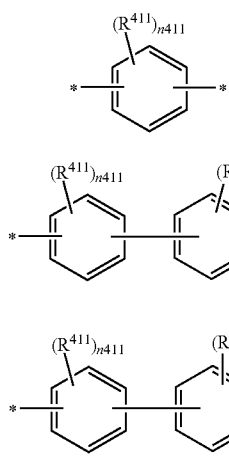

General Formula 1-1

General Formula 1-2

General Formula 1-3

(The $R^{411}$ [groups] represent each independently a substituent. The $n^{411}$ [groups] represent each independently an integer from 0 to 4. The asterisk indicates a bond, with one being a bond with dibenzothiophene or dibenzofuran, and the other a bond with phenanthrene.)

There are no particular restrictions on the substituent expressed by $R^{411}$, but examples include the substituents listed as examples of the aforementioned Substituent Group A. The $R^{411}$ [groups] preferably represent each independently an alkyl group, aryl group, hetero aryl group; or cyano group, more preferably an aryl group, hetero aryl group, or cyano group, and even more preferably a cyano group. A cyano group is preferable in terms of contributing to an increase in heat resistance and charge injection properties.

$R^{411}$ may have a further substituent, and examples of the further substituent include an alkyl group and an aryl group. The alkyl group serving as the further substituent is defined the same as the alkyl group expressed by $R^{111}$ to $R^{126}$, and preferred examples are also defined the same. The aryl group serving as a further substituent preferably has a carbon number of 6 to 30, more preferably a carbon number of 6 to 20, and even more preferably a carbon number of 6 to 14, and is preferably a phenyl group, naphthyl group, or phenanthryl group, and more preferably a phenyl group.

The $n^{411}$ [groups] preferably represent each independently 0 to 2, more preferably 0 or 1, and even more preferably 0.

The compound expressed by General Formula 1 above is preferably a compound expressed by General Formula 2 below and a compound expressed by General Formula 3 below. The present invention also relates to the compound expressed by General Formula 3. The compound expressed by General Formula 3 is useful as a charge transport material or an organic electroluminescent element material.

(Compound Expressed by General Formula 2)

[Seventh Chemical Formula]

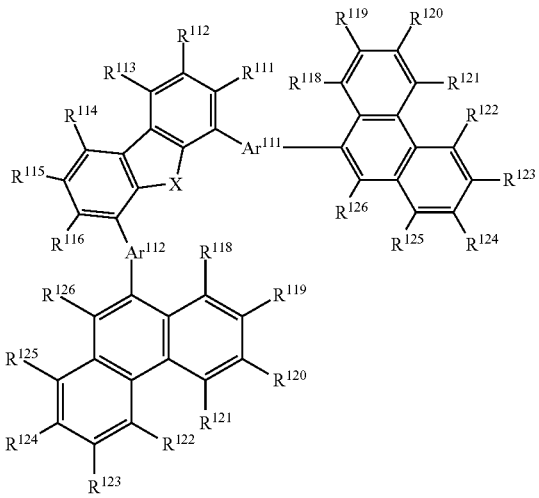

General Formula 2

In General Formula 2, X represents an oxygen atom or a sulfur atom, $R^{111}$ to $R^{116}$ and $R^{118}$ to $R^{126}$ represent each independently a hydrogen atom or a substituent, and $Ar^{111}$ and $Ar^{112}$ represent each independently an arylene group.

$R^{111}$ to $R^{116}$ and $R^{118}$ to $R^{126}$ in General Formula 2 are defined the same as $R^{111}$ to $R^{126}$ in General Formula 1, and the preferred ranges are also the same. $Ar^{111}$ and $Ar^{112}$ in General Formula 2 are defined the same as $Ar^{111}$ in General Formula 1, and the preferred ranges are also the same.

X is preferably a sulfur atom.

(Compound Expressed by General Formula 3)

[Eighth Chemical Formula]

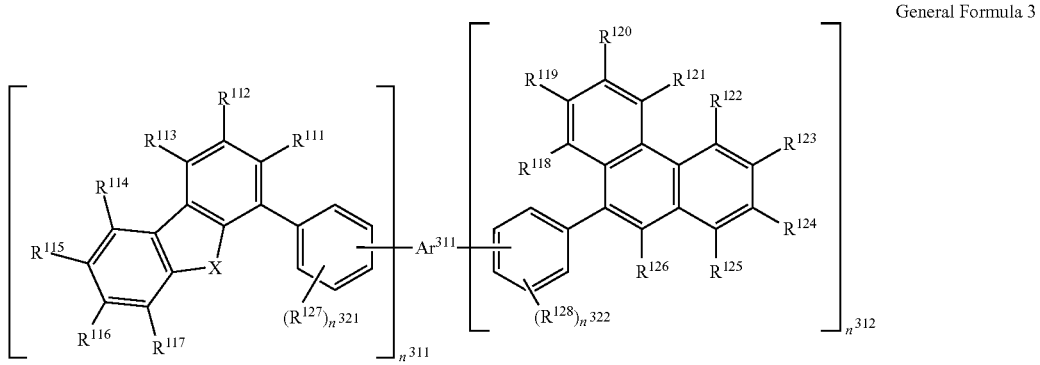

General Formula 3

In General Formula 3, X represents an oxygen atom or a sulfur atom, $R^{111}$ to $R^{126}$ represent each independently a hydrogen atom or a substituent, and $R^{127}$ and $R^{128}$ represent each independently a substituent. $n^{311}$ and $n^{312}$ represent each independently 1 or 2, $n^{321}$ and $n^{322}$ represent each independently an integer from 0 to 4, and $Ar^{311}$ a single bond or an aromatic group of $n^{311}+n^{312}$ valence.

$R^{111}$ to $R^{126}$ in General Formula 3 are defined the same as $R^{111}$ to $R^{126}$ in General Formula 1, and the preferred ranges are also the same.

The substituents expressed by $R^{127}$ and $R^{128}$ are defined the same as the substituents expressed by $R^{111}$ to $R^{126}$ in General Formula 1, and the preferred ranges are also the same.

$n^{311}$ and $n^{312}$ preferably represent each independently 1 or 2, and more preferably are both 1.

If $n^{311}$ and $n^{312}$ are each 1, then $Ar^{311}$ represents a single bond or a divalent aromatic group. The divalent aromatic group is defined the same as the arylene group serving as $Ar^{111}$ in General Formula 1, and the preferred ranges are also the same.

When the total of $n^{311}$ and $n^{312}$ is 3 or 4, $Ar^{311}$ is a trivalent or tetravalent aromatic, ring group, examples of which include trivalent or tetravalent groups from which any one or two hydrogen atoms have been removed from an arylene group serving as $Ar^{111}$ in General Formula 1.

X is preferably a sulfur atom.

The molecular weight of the compounds expressed by any of General Formulas 1 to 3 is usually at least 400 and no more than 1500, preferably at least 450 and no more than 1200, even more preferably at least 500 and no more than 1100, and still more preferably at least 600 and no more than 1000. If the molecular weight is at least 450, this is advantageous in terms of forming a good-quality amorphous thin film, and if the molecular weight is no more than 1200, this is advantageous in terms of enhancing the solubility and sublimation properties and in increasing the purity of the compound.

When a compound expressed by any of General Formulas 1 to 3 is used as the host material of light-emitting layer of an organic electroluminescent element or as the charge transport material of a layer adjacent to the light-emitting layer, if the energy gap in a thin film state (when the light-emitting material is a phosphorescent material, the lowest excitation triplet ($T_1$) energy in a thin film state) is greater than that of the light-emitting, material, this is advantageous in preventing the emission of light from being quenched and in increasing efficiency. On the other hand, from the standpoint of the chemical stability of the compound, it is preferable for the energy gap and the $T_1$ energy not to be too great.

The $T_1$ energy in a film state of a compound expressed by any of General Formulas 1 to 3 is preferably at least 239 eV (55 kcal/mol) and no more than 151 eV (80 kcal/mol) and more preferably at least 2.52 eV (58 kcal/mol) and no more than 3.04 eV (70 kcal/mot) in a green-light-emitting element. In particular, when a phosphorescent material is used as the light-emitting material, the $T_1$ energy is preferably within the aforementioned range.

By measuring the phosphorescence spectrum of a thin film of the material, the $T_1$ energy can be found from the short-wavelength end thereof. For instance, a film of the material is formed in a thickness of approximately 50 nm by a vacuum deposition method over a washed quartz glass substrate, and the phosphorescence spectrum of the thin film is measured using a Hitachi F-7000 spectrofluoro-photometer (Hitachi High-Technologies) at the temperature of liquid nitrogen. The $T_1$ energy can be found by converting the rising wavelength on the short-wavelength side of the emission spectrum thus obtained to energy units.

From the standpoint of stable operation of the organic electroluminescent element with respect to heat emission in element drive or during high-temperature drive, the glass transition temperature (Tg) of the compound expressed by any of General Formulas 1 to 3 is preferably at least 100° C. and no more than 400° C. more preferably at least 110° C. and no more than 400° C., and even more preferably at least 120° C. and no more than 400° C.

If the purity of the compound expressed by any of General Formulas 1 to 3 is low, impurities will become traps for charge transport or accelerate degradation of the element, so the higher the purity of the compound expressed by any of General Formulas 1 to 3 is, the better. The purity can be measured, for example, by high-performance liquid chromatography (HPLC), and the surface area ratio of the compound expressed by any of General Formulas 1 to 3 as detected at an optical absorption intensity of 254 nm is preferably at least 95.0% and more preferably at least 97.0%, with at least 99.0% being particularly preferable and at least 99.9% being most preferable.

As is known from the carbazole-based material described in WO 2008/117889, a material in which some or all of the hydrogen atoms in the compound expressed by any of General Formulas 1 to 3 have been replaced with deuterium atoms can also be used.

Concrete examples of the compound expressed by any of General Formulas 1 to 3 are given below, but the present invention is not limited to or by these.

[Ninth Chemical Formula]

compound 1-1

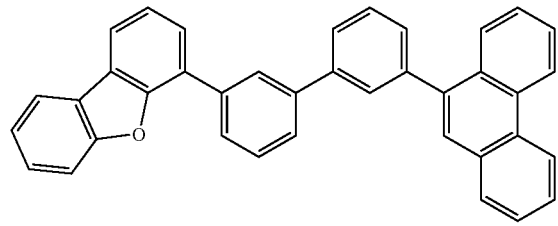

compound 1-2

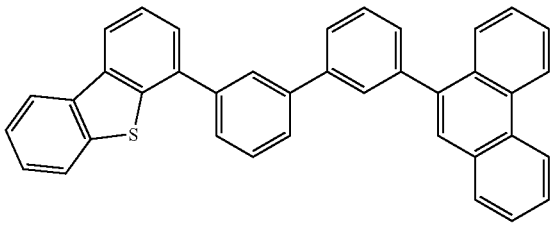

compound 1-3

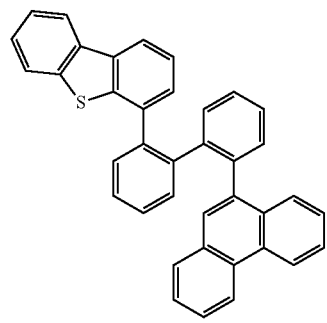

compound 1-4

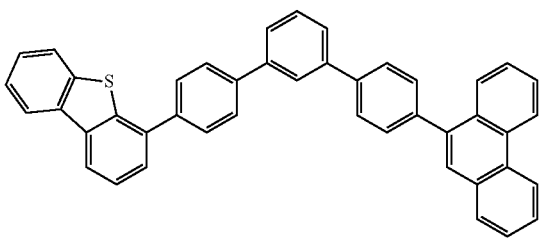

compound 1-5

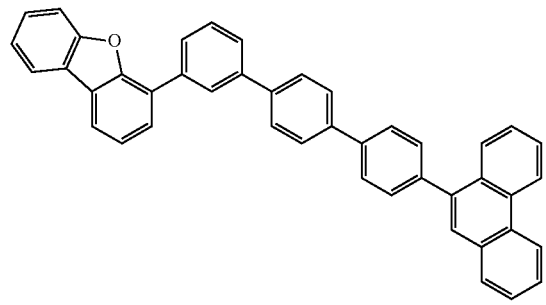

compound 1-6

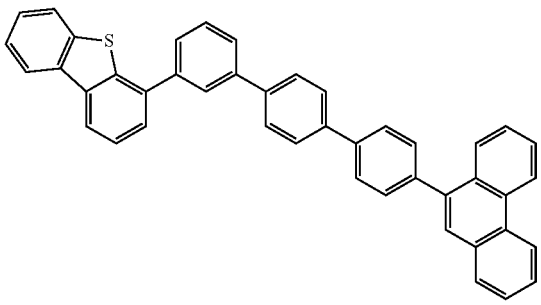

compound 1-7

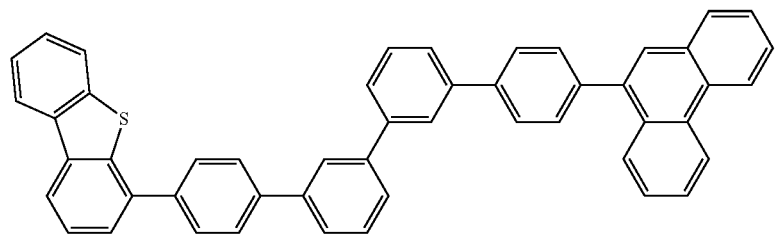

compound 1-8

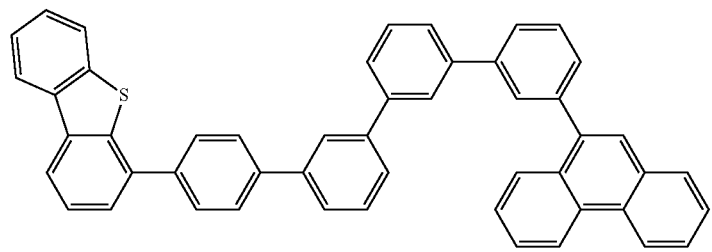

[Tenth Chemical Formula]
compound 1-9
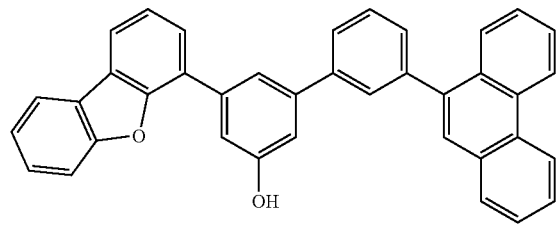
compound 1-10
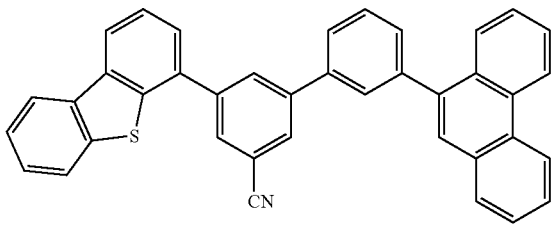
compound 1-11
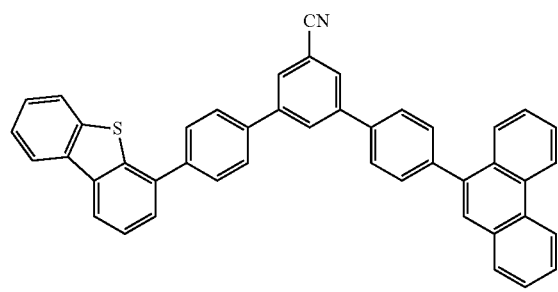
compound 1-12
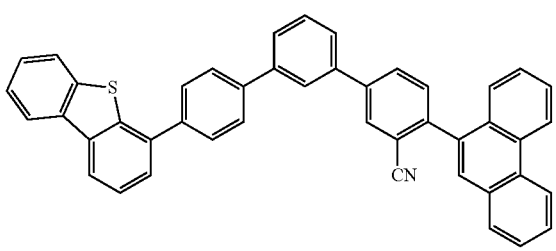
compound 1-13
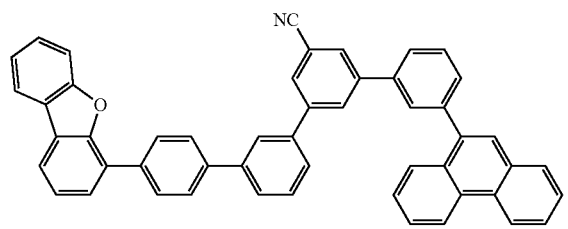
compound 1-14
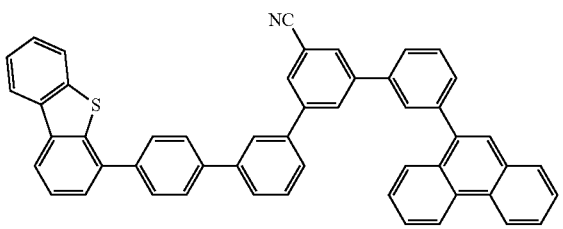
compound 1-15
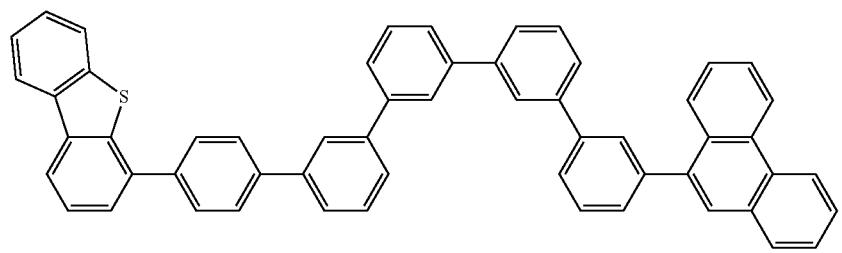
compound 1-16
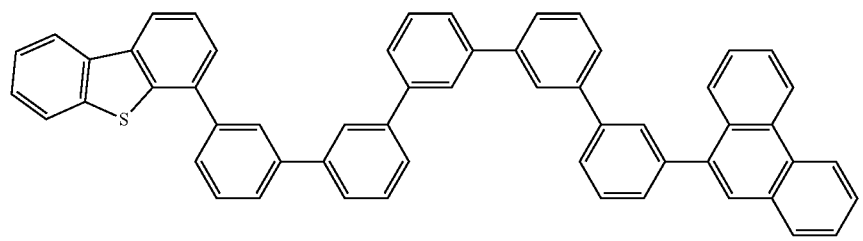

-continued
[Eleventh Chemical Formula]
compound 1-17
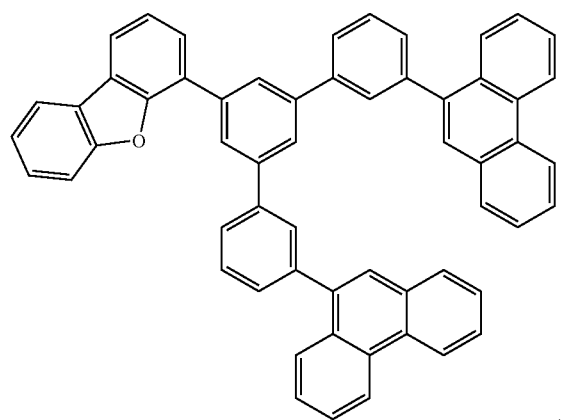
compound 1-18
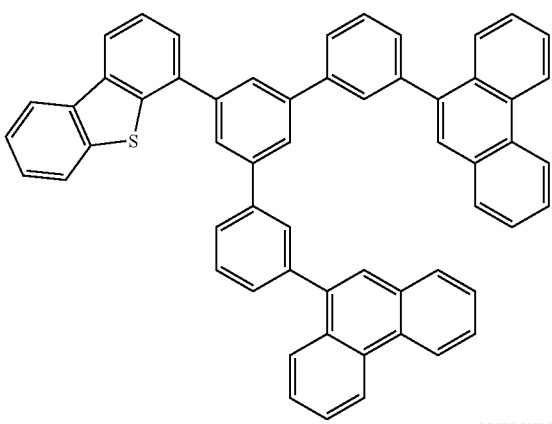
compound 1-19
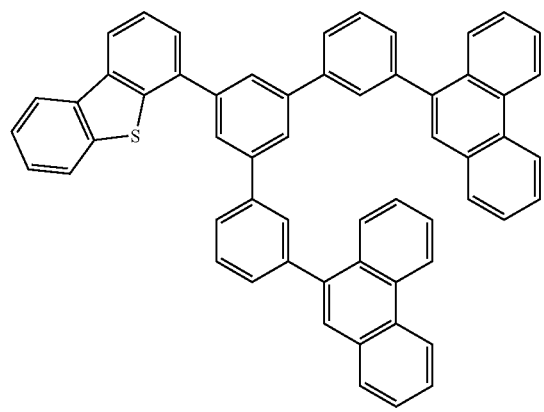
compound 1-20
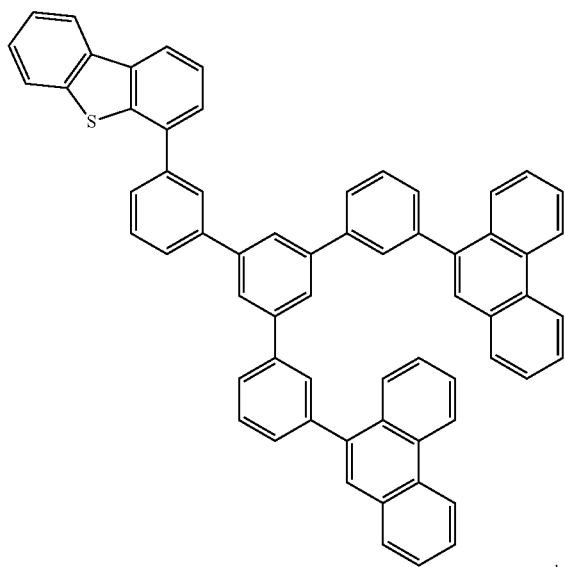
compound 1-21
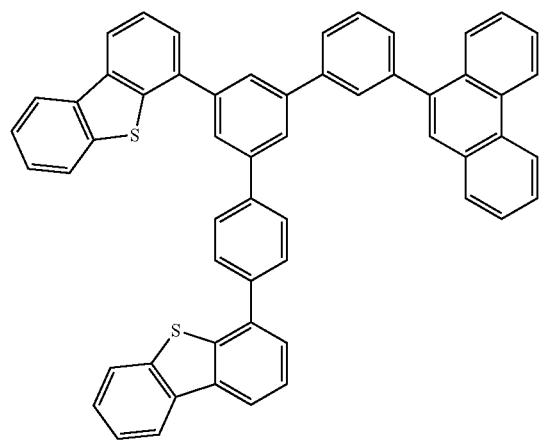
compound 1-22
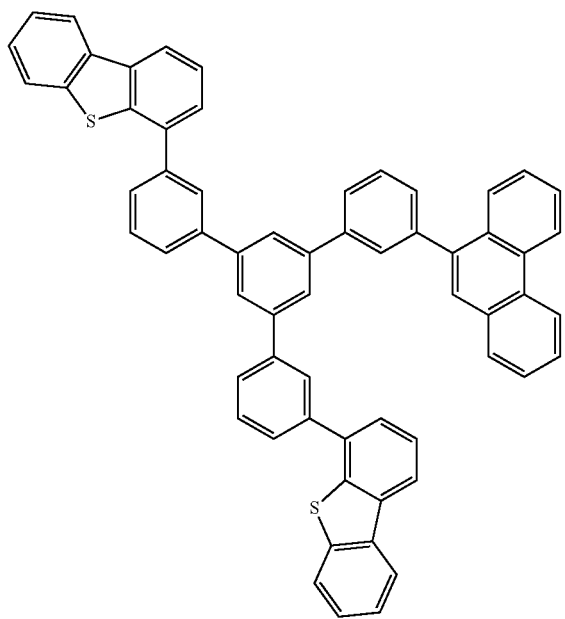

[Twelfth Chemical Formula]
compound 1-23
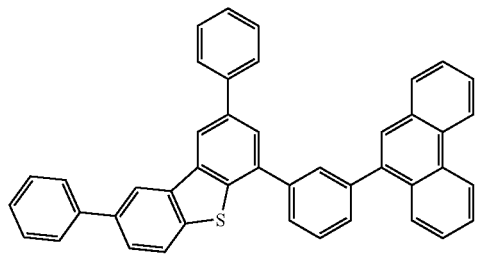
compound 1-24
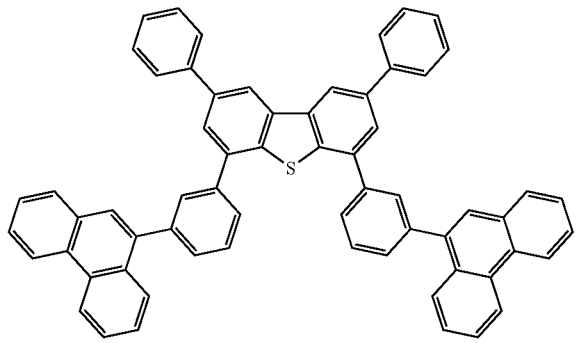
compound 1-25
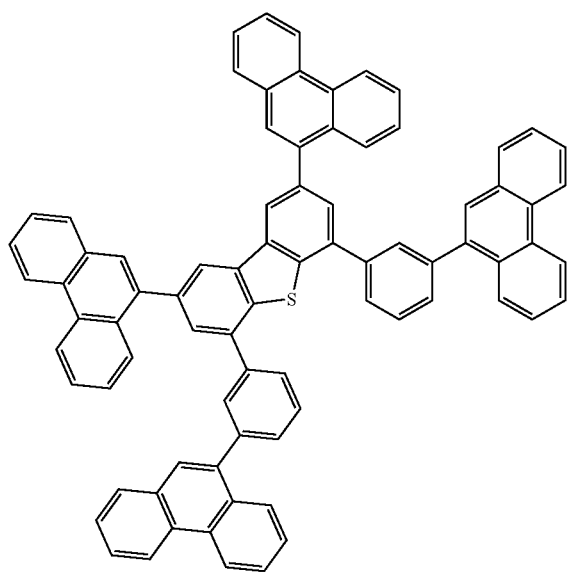
compound 1-26
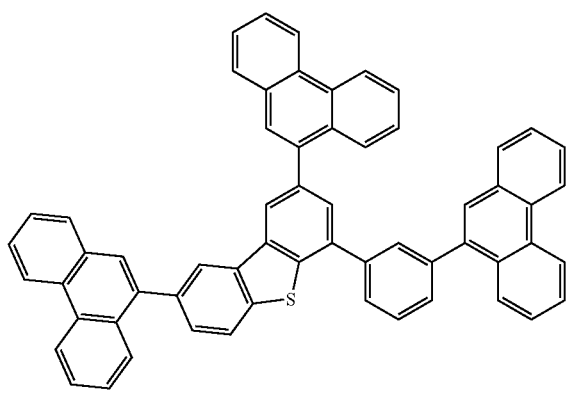
compound 1-27
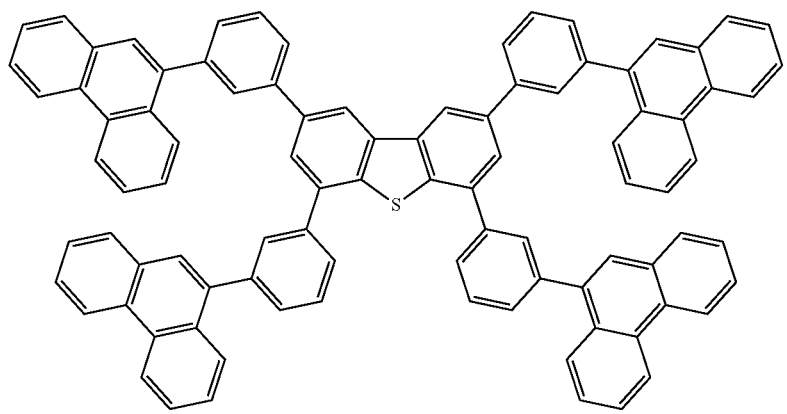

compound 1-28
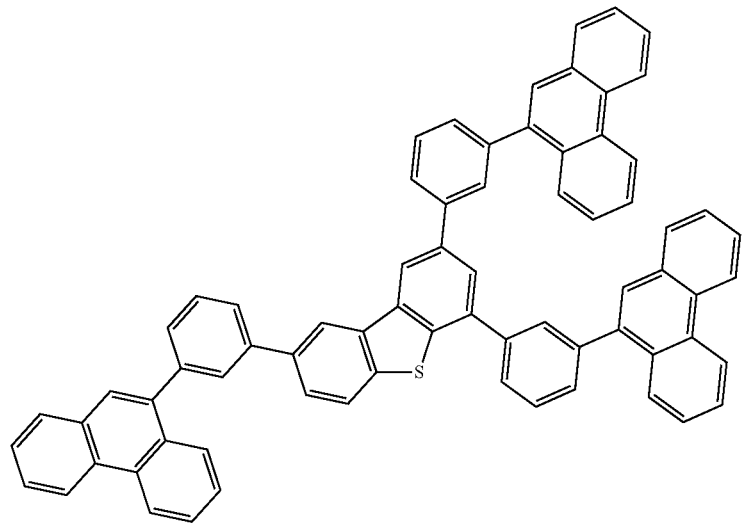
[Thirtheenth Chemical Formula]
compound 1-29
compound 1-30
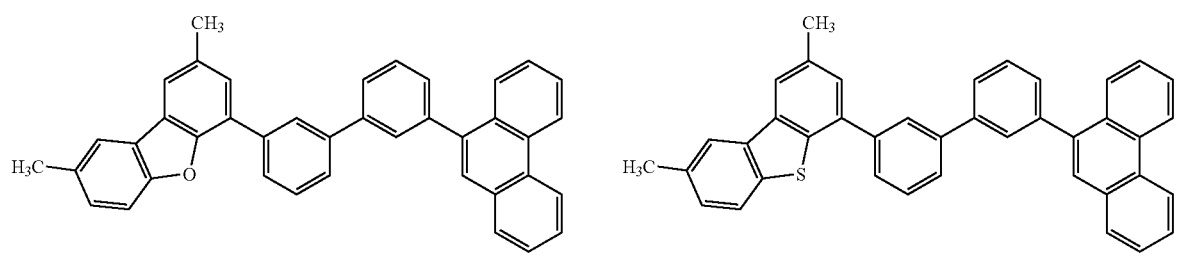
compound 1-31
compound 1-32
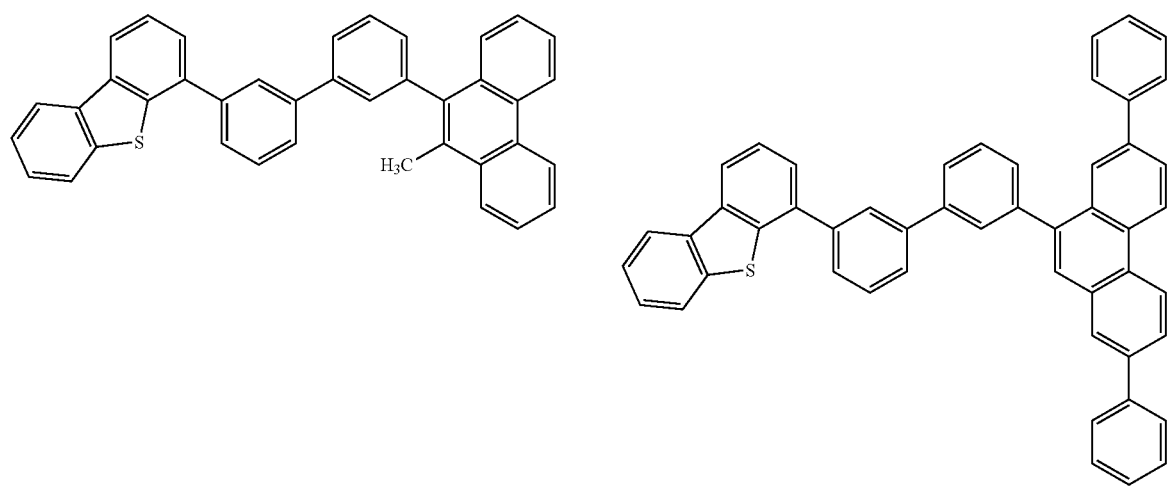

compound 1-33
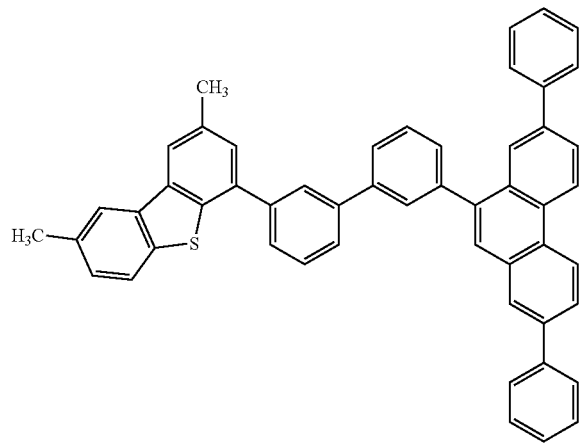
compound 1-34
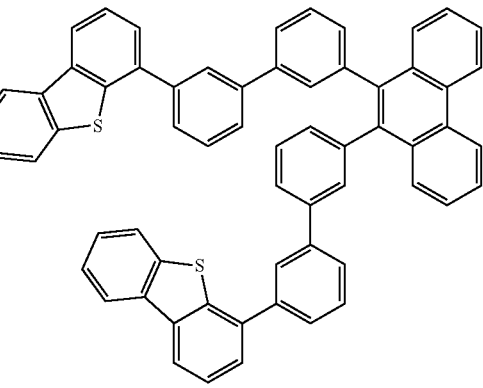
[Fourtheenth Chemical Formula]
compound 1-35
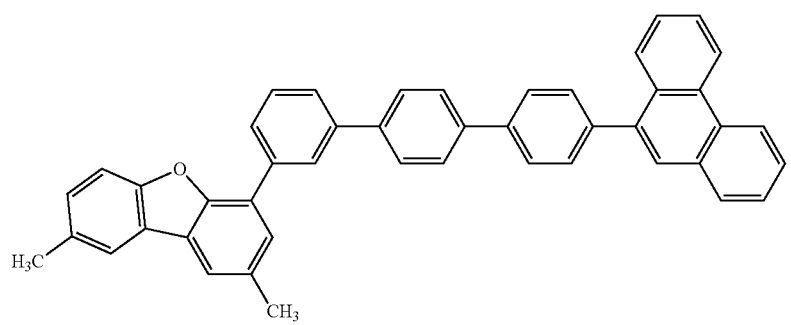
compound 1-36
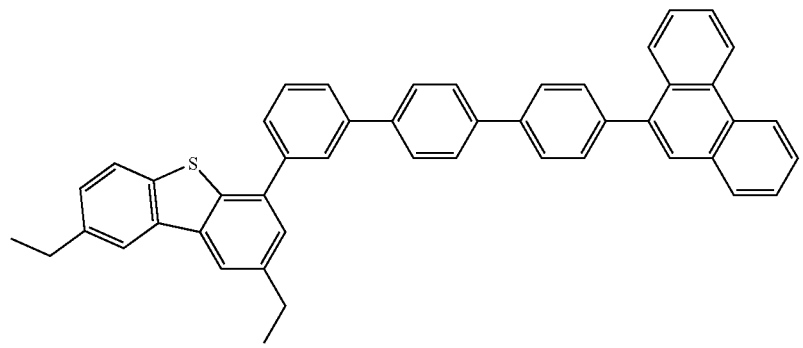
compound 1-37
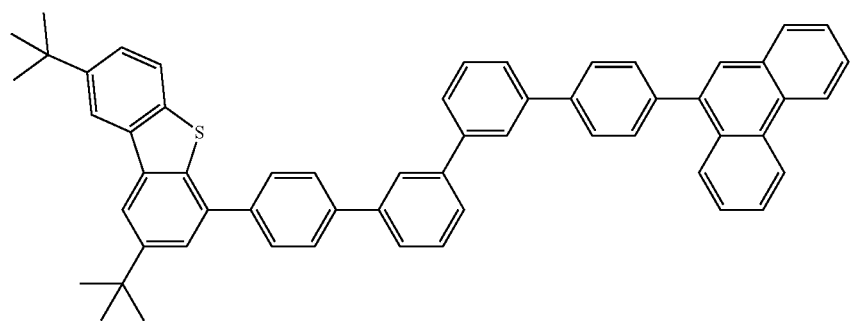

compound 1-38
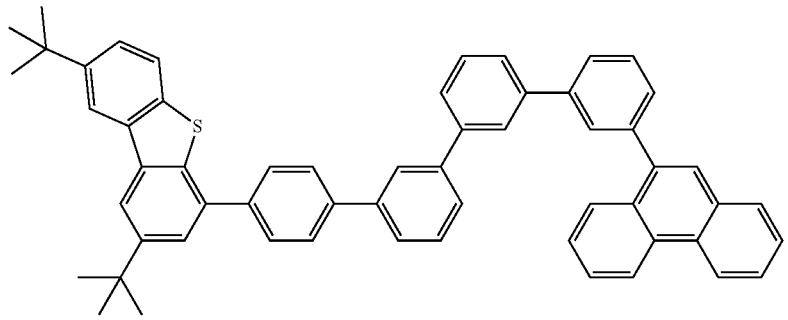
compound 1-39
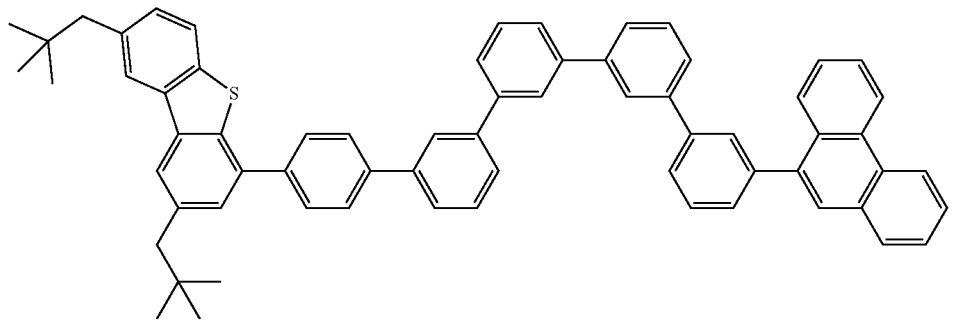
compound 1-40
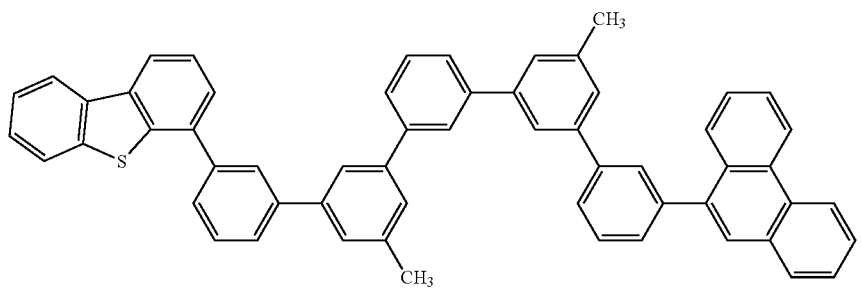
[Fifteenth Chemical Formula]
compound 1-41
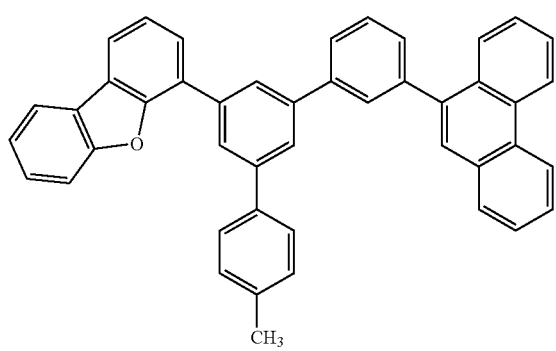
compound 1-42
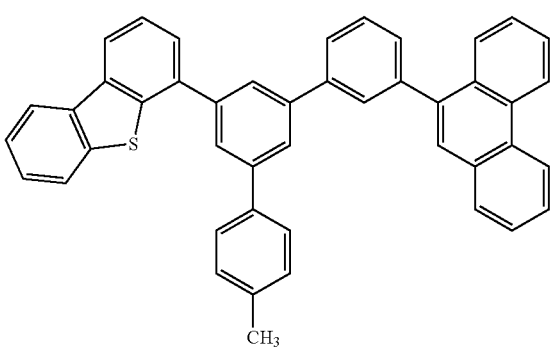
compound 1-43
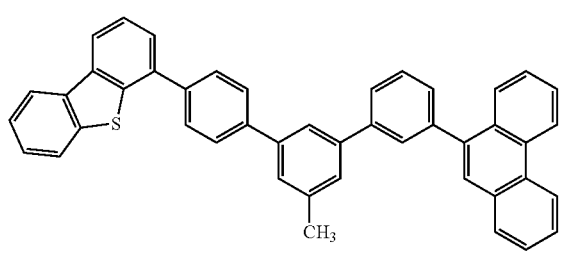
compound 1-44
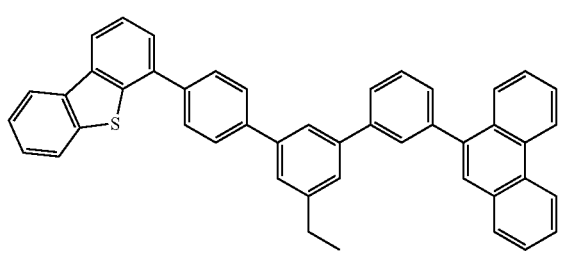

compound 1-45
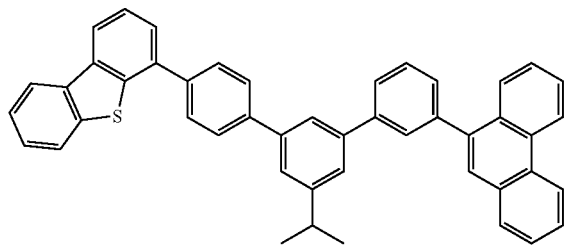
compound 1-46
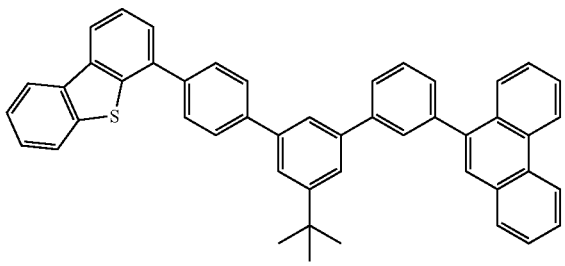
compound 1-47
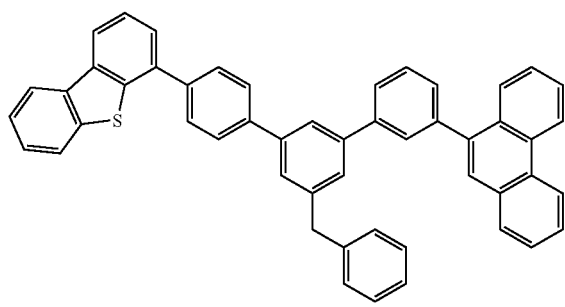
compound 1-48
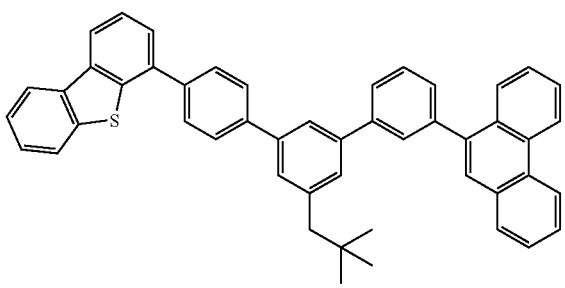
[Sixteenth Chemical Formula]
compound 1-49
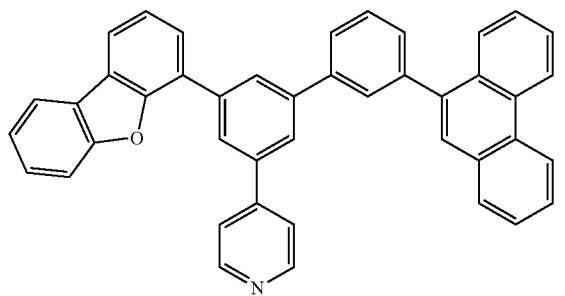
compound 1-50
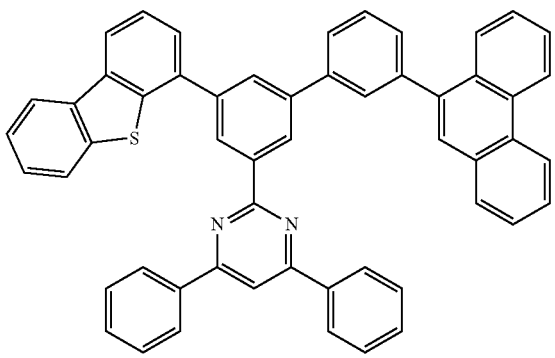
compound 1-51
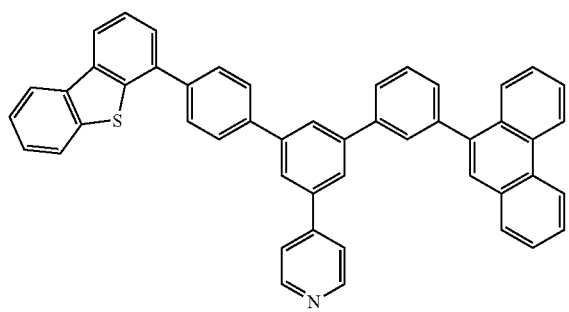
compound 1-52
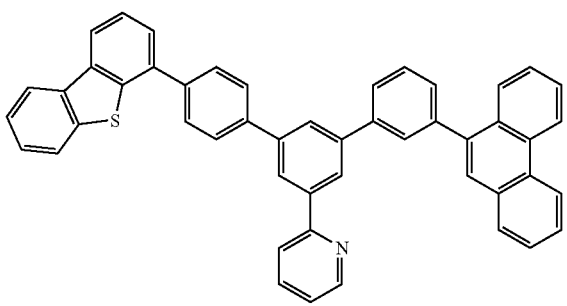

-continued
compound 1-53
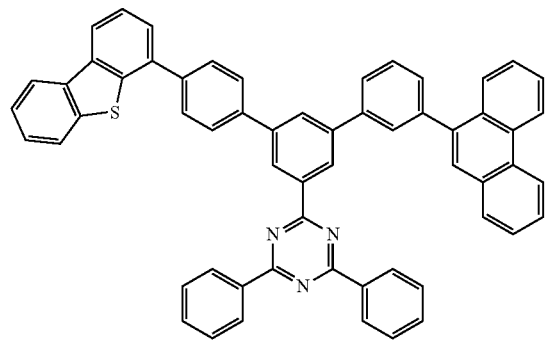
compound 1-54
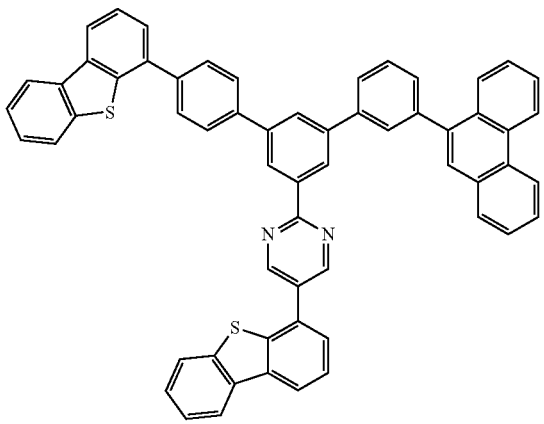
compound 1-55
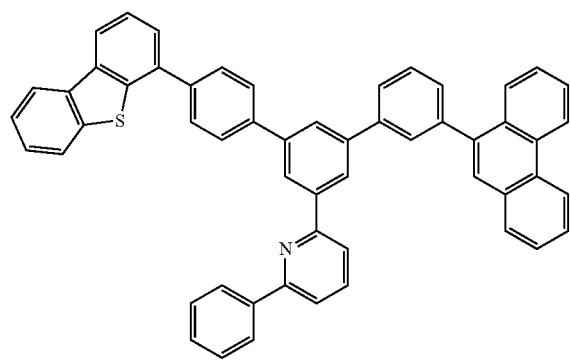
compound 1-56
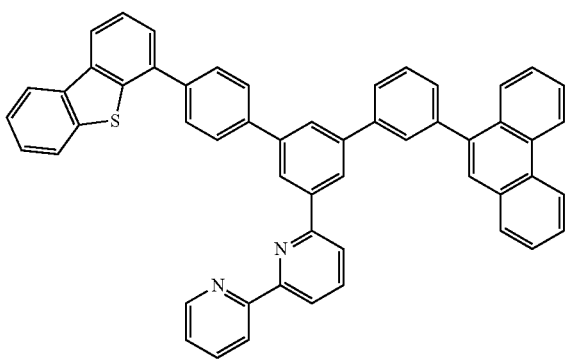
[Seventeenth Chemical Formula]
compound 1-57
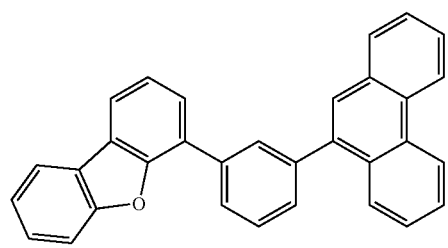
compound 1-58
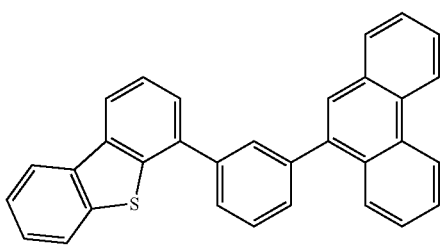
compound 1-59
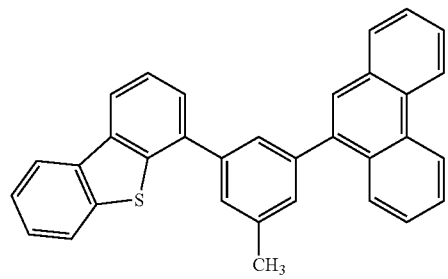
compound 1-60
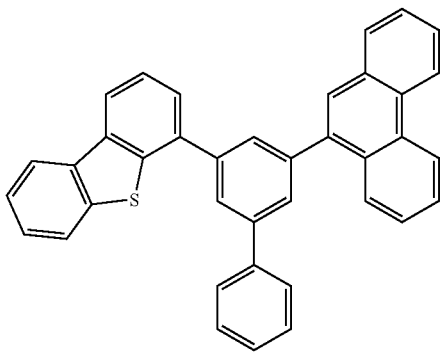

compound 1-61

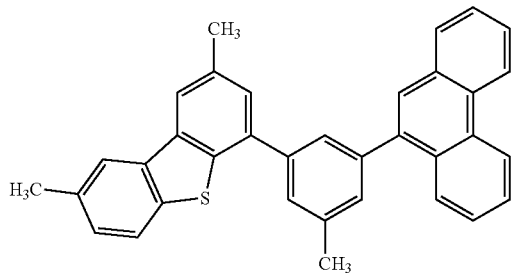

compound 1-62

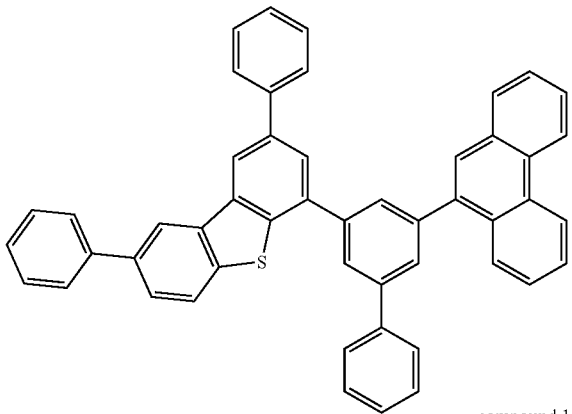

compound 1-63

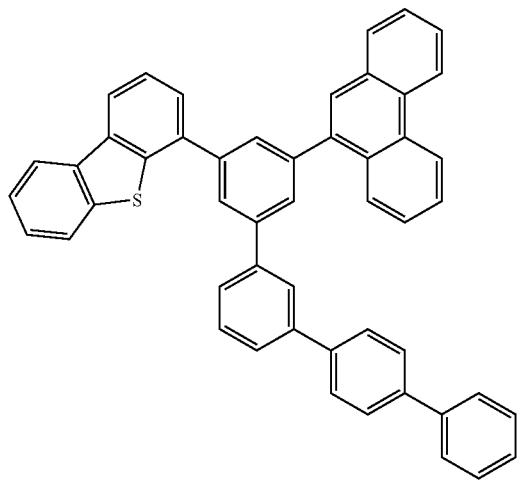

compound 1-64

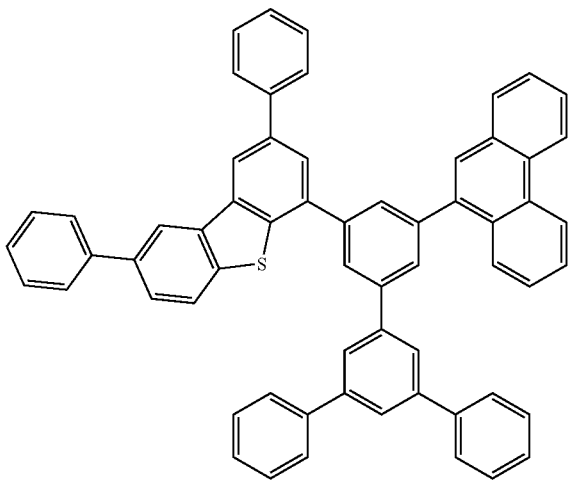

-continued

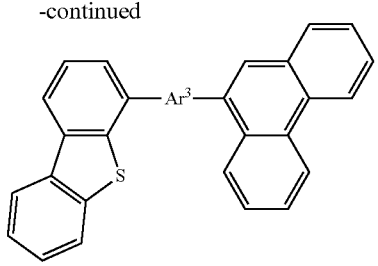

(X = Cl, Br, I, OTs etc.)

The compound expressed by General Formula 1 above can be synthesized, for example, by the method described in WO 2007/069569, etc.

Note that the compound expressed by General Formula 3 is a novel compound but can be synthesized by the aforementioned method or as follows, for example: $Ar^3$ is defined the same as $Ar^{311}$ in General Formula 3,

[Eighteenth Chemical Formula]

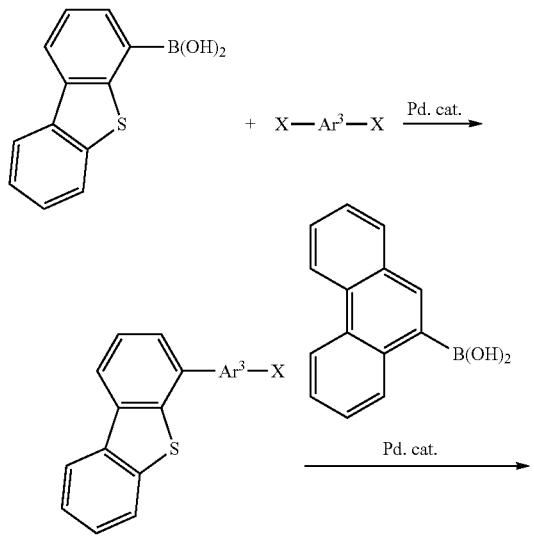

In the present invention, there are no limitations on the applications of the compound expressed by any of General Formulas 1 to 3, and [this compound] may be contained in any of the organic layers. The layer into which the compound expressed by any of General Formulas 1 to 3 is introduced is preferably the light-emitting layer, a layer between the light-emitting layer and the cathode, or a layer between the light-emitting layer and the anode, or [the compound] is contained in a plurality [of layers]. More preferably, [the compound] is contained in the light-emitting layer, a hole injection layer, a hole transport layer, an electron transport layer, an electron injection layer, an exciton blocking layer, or a charge blocking layer, or a plurality [of layers]. Even more preferably, [the compound] is contained in the light-emitting layer, the electron transport layer, or the electron injection layer.

In the present invention, in order to better suppress changes in chromaticity after drive at high temperatures, the compound expressed by any of General Formulas 1 to 3 is preferably contained in the light-emitting layer, an organic layer adjacent to the light-emitting layer between the light-emitting layer and the cathode (a layer adjacent to the light-emitting layer on the cathode side), or an electron injection layer adjacent to the cathode on the light-emitting layer side. More preferably, [the compound] is contained in either the light-emitting layer or a layer adjacent to the light-emitting layer on the cathode side. Even more preferably, it is contained in the light-emitting layer. In addition, the compound expressed by any of General Formulas 1 to 3 may also be contained in both the light-emitting layer and a layer adjacent to the light-emitting layer on the cathode side.

When the compound expressed by any of General Formulas 1 to 3 is contained in the light-emitting layer, the compound expressed by any of General Formulas 1 to 3 of the present invention is preferably contained in an amount of 0.1 to 99 wt %, more preferably 1 to 97 wt %; and even more preferably 10 to 96 wt %, with respect to the total weight of the light-emitting layer. When the compound expressed by any of General Formulas 1 to 3 is further contained in a layer other than the light-emitting layer, it is preferably contained in an amount of 70 to 100 wt % and more preferably 85 to 100 wt % with respect to the total weight of this layer other than the light-emitting layer.

(Charge Transport Material Expressed by General Formula 1)

The present invention also relates to a charge transport material expressed by General Formula 1 above. The charge transport material expressed by General Formula 1 above is preferably a charge transport material expressed by General Formula 2 or 3 above.

(Applications of Compound and Charge Transport Material Expressed by General Formula 1 of the Present Invention)

The compound and the charge transport material expressed by General Formula 1 of the present invention can be used favorably in electrophotography, organic transistors, organic opto-electric conversion elements (energy conversion applications, sensor applications, etc.), organic electroluminescent elements, and other such organic electronics element, and can be used to particular advantage in an organic electroluminescent element.

(Composition Containing the Charge Transport Material of the Present Invention)

The present invention also relates to a composition containing the aforementioned charge transport material. In the composition of the present invention, the content of the compound expressed by any of General Formulas 1 to 3 is preferably 30 to 99 wt %, more preferably 50 to 97 wt %, and even more preferably 70 to 96 wt %, with respect to the total solids in the composition. Other components that may be contained in the composition of the present invention may be organic or inorganic; as organic substances, materials listed as the host material (described later), fluorescent materials, phosphorescent materials, and hydrocarbon materials are applicable, with the host material, phosphorescent materials, and hydrocarbon materials being preferable.

The composition of the present invention can be formed into an organic layer of an organic electroluminescent element by vapor deposition, sputtering, or another such dry film formation method, or by transfer, printing, or another such wet film formation method.

(Thin Film Containing the Charge Transport Material of the Present Invention)

The present invention also relates to a thin film containing the charge transport material expressed by any of General Formulas 1 to 3. The thin film of the present invention can be formed by using the composition of the present invention by vapor deposition, sputtering, or another such dry film formation method, or by transfer, printing, or another such wet film formation method. The thickness of the thin film may be any thickness depending on the application, but it is preferably 0.1 nm to 1 mm, more preferably 0.5 nm to 1 μm, even more preferably 1 nm to 200 nm, and particularly preferably 1 nm to 100 nm.

(Organic Electroluminescent Element)

The organic electroluminescent element of the present invention will now be described in detail.

The organic electroluminescent element of the present invention is an organic electroluminescent element which has on a substrate a pair of electrodes comprising an anode and a cathode and at least one organic layer including a light-emitting, layer between these electrodes, with at least one layer out of the aforementioned at least one organic layer containing a compound expressed by General Formulas 1 to 3.

For the quality of the light-emitting element, it is preferable that at least either the anode or cathode constituting the pair of electrodes be transparent or semitransparent.

Examples of organic layers besides a light-emitting layer include a hole injection layer, a hole transport layer, a blocking layer (a hole blocking layer, an exciton blocking layer, etc.), and an electron transport layer. A plurality of each of these organic layers may be provided, and when a plurality of layers are provided, they may be formed from the same material, or they may be formed from different materials for each layer.

FIG. 1 shows one example of the configuration of the organic electroluminescent element according to the present invention. The organic electroluminescent element 10 in FIG. 1 has on a substrate 2 organic layers including a light-emitting layer 6 between a pair of electrodes (an anode 3 and a cathode 9). For the organic layers, a hole injection layer 4, a hole transport layer 5, the light-emitting layer 6, a hole blocking layer 7, and an electron transport layer 8 are laminated in this order starting from the side of the anode 3.

<Configuration of Organic Layers>

There are no particular restrictions on the layer configuration of the aforementioned organic layers, which can be suitably selected according to the purpose and application of the organic electroluminescent element, but [the organic layers] are preferably formed over the aforementioned transparent electrode(s) or the aforementioned semi-transparent electrode(s). In this case, the organic layers are formed on the front face or one face of the aforementioned transparent electrode(s) or the aforementioned semi-transparent electrode(s).

There are no particular restrictions on the shape, size, thickness, and so forth of the organic layers, which can be suitably selected according to the purpose.

The following are concrete examples of the layer configuration, but the present invention is not limited to these configurations:

anode/hole transport layer/light-emitting layer/electron transport layer/cathode anode/hole transport layer/light-emitting layer/blocking layer/electron transport layer/cathode anode/hole transport layer/light-emitting layer/blocking layer/electron transport layer/electron injection layer/cathode anode/hole injection layer/hole transport layer/light-emitting layer/blocking layer/electron transport layer/cathode anode/hole injection layer/hole transport layer/light-emitting layer/electron transport layer/electron injection layer cathode anode/hole injection layer/hole transport layer/light-emitting layer/blocking layer electron transport layer/electron injection layer/cathode The element configuration, substrate, cathode, and anode of the organic electroluminescent element are discussed in detail in Japanese Laid-Open Patent Application 2008-270736, for example, and what is discussed in this publication can be applied to the present invention.

<Substrate>

The substrate used in the present invention is preferably a substrate that will not scatter or attenuate light emitted from the organic layers. In the case of an organic material, one with excellent heat resistance, dimensional stability, solvent resistance, electrical insulation properties, and workability is preferable.

<Anode>

In general, there are no particular restrictions on the shape, structure, size, and so forth of the anode as long as it functions as an electrode that supplies holes to the organic layers, and one can be suitably selected from publicly known electrode materials depending on the purpose and application of the light-emitting element. As was discussed above, the anode is usually provided as a transparent anode.

<Cathode>

In general, there are no particular restrictions on the shape, structure, size, and so forth of the cathode as long as it functions as an electrode that injects electrons into the organic layers, and one can be suitably selected from publicly known electrode materials depending on the purpose and application of the light-emitting element.

<Organic Layers>

The organic layers of the present invention will be described.

(Shape of Organic Layers)

Each of the organic layers of the organic electroluminescent element of the present invention can be favorably formed by vapor deposition, sputtering, or another such dry film formation method, or by transfer, printing, spin coating, bar coating, or another such solution coating method. It is preferable if at least one of the organic layers is formed by solution coating.

(Light-emitting Layer)

When an electric field is applied, the light-emitting layer accepts holes from the anode, the hole injection layer, or the hole transport layer, accepts electrons from the cathode, the electron injection layer, or the electron transport layer, and has the function of emitting light by providing a site for the rebinding of holes and electrons. The light-emitting layer in the organic electroluminescent element of the present invention preferably contains at least one type of phosphorescent material.

The light-emitting layer in the organic electroluminescent element of the present invention preferably contains the compound expressed by any of General Formulas 1 to 3 above as a host material (described later).

(Light-emitting Material)

With the present invention, a fluorescent material or a phosphorescent material can be used as the light-emitting material in the light-emitting layer.

These fluorescent materials and phosphorescent materials are discussed at length, for example, in paragraph numbers [0100] to [0164] of Japanese Laid-Open Patent Application 2008-270736 and paragraph numbers [0088] to [0090] of Japanese Laid-Open Patent Application 2007-266458, and what is discussed in these publications can be applied to the present invention.

Examples of phosphorescent materials that can be used in the present invention include the phosphorescent compounds or the like described in patent documents such as U.S. Pat. No. 6,303,238 B1, U.S. Pat. No. 6,097,147, WO 00/57676, WO00/70655, WO 01/08230, WO 01/39234 A2, WO 01/41512 A1, WO02/02714 A2, WO02/15645 A1, WO 02/44189 A1, WO 05/19373 A2, Japanese Laid-Open Patent Applications 2001-247859, 2002-302671, 2002-117978, 2003-133074, 2002-235076, 2003-423982, and 2002-170684, EP 1211257, and Japanese Laid-Open Patent Applications 2002-226495, 2002-234894, 2001-247859, 2001-298470, 2002-173674, 2002-203678, 2002-203679, 2004-357791, 2006-256999, 2007-19462, 2007-84635, and 2007-96259. Of these, examples of more preferable light-emitting materials include iridium complexes, platinum complexes, copper complexes, rhenium complexes, tungsten complexes, rhodium complexes, ruthenium complexes, palladium complexes, osmium complexes, europium complexes, terbium complexes, gadolinium complexes, dysprosium complexes, cerium complexes, and other such phosphorescent metal complex compounds. Particularly preferable are iridium complexes, platinum complexes, and rhenium complexes, and of these, iridium complexes, platinum complexes, and rhenium complexes that include at least one coordination from among a metal-carbon bond, a metal-nitrogen bond, a metal-oxygen bond, and a metal-sulfur bond are preferred. From the standpoints of luminous efficiency, drive durability, chromaticity, and so forth, iridium complexes and platinum complexes are especially preferable, with iridium complexes being most preferable.

These phosphorescent metal complex compounds are preferably contained in the light-emitting layer along with a compound expressed by any of General Formulas 1 to 3 above.

For the phosphorescent material contained in the light-emitting layer in the present invention, it is preferable to use an iridium complex expressed by General Formula T-1 below or a platinum complex expressed by General Formula C-1 below.

(Compound Expressed by General Formula T-1)

The compound expressed by General Formula T-1 will be described.

[Nineteenth Chemical Formula]

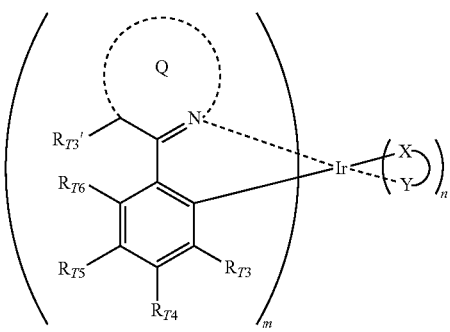

(In General Formula T-1, $R_{T3}'$, $R_{T3}$, $R_{T4}$, $R_{T5}$, and $R_{T6}$ represent each independently a hydrogen atom or a substituent;

any adjacent two of $R_{T3}$, $R_{T4}$, $R_{T5}$, and $R_{T6}$ may bind together to form a condensed four- to seven-member ring, this condensed four- to seven-member ring is a cycloalkyl, an aryl, or a heteroaryl, and this condensed four- to seven-member ring may further have a substituent;

$R_{T3}'$ and $R_{T6}$ may form a ring by being linked by it linking group selected, from among —C($R_T$)$_2$—C($R_T$)$_2$—, —C$R_T$=C$R_T$—, —C($R_T$)$_2$—, —O—, —N$R_T$—, —O—C($R_T$)$_2$—, —N$R_T$—C($R_T$)$_2$—, and —N=C$R_T$—, the $R_T$ [groups] represent each independently a hydrogen atom, an alkyl group, an alkenyl group, an alkynyl group, an aryl group, or a heteroaryl group, and may further have a substituent;

the ring Q is a five- or six-member aromatic heterocycle or condensed aromatic heterocycle including at least one nitrogen; and (X—Y) represents an auxiliary ligand, in represents an integer of 1 to 3, n represents an integer of 0 to 2, and in m+n=3).

The aforementioned Substituent Group A can be given as examples of the substituents expressed by $R_{T3}'$, $R_{T3}$, $R_{T4}$, $R_{T5}$, and $R_{T6}$, each independently. Preferably, these express an alkyl group, alkenyl group, alkynyl group, —CN, perfluoroalkyl group, trifluorovinyl group, —CO$_2$$R_T$, C(O)$R_T$, —N($R_T$)$_2$, —NO$_2$, —O$R_T$, fluorine atom, aryl group, or heteroaryl group, and may further have a substituent T.

The substituents T represent each independently a fluorine atom, —R', —OR', —N(R')$_2$, —SR', —C(O)R', —C(O)OR', —C(O)N(R')$_2$, —CN, —NO$_2$, —SO$_2$, —SOR', —SO$_2$R', or —SO$_3$R', and the R' [groups] represent each independently a hydrogen atom, an alkyl group, a perfluoroalkyl group, an alkenyl group, an alkynyl group, an aryl group, or a heteroaryl group.

The alkyl group may have a substituent and may be either saturated or unsaturated, and examples of groups that may be substituted include the aforementioned substituents T. The alkyl groups expressed by $R_{T3}'$, $R_{T3}$, $R_{T4}$, $R_{T5}$, and $R_{T6}$ are preferably alkyl groups with a total number of carbon atoms of 1 to 8 and more preferably alkyl groups with a total number of carbon atoms of 1 to 6, examples of which include a methyl group, ethyl group, i-propyl group, and t-butyl group.

The cycloalkyl group may have a substituent and may be either saturated or unsaturated, and examples of groups that may be substituted include the aforementioned substituents T. The cycloalkyl groups expressed by $R_{T3}'$, $R_{T3}$, $R_{T4}$, $R_{T5}$, and $R_{T6}$ are preferably cycloalkyl groups with 4 to 7 ring members and more preferably cycloalkyl groups with a total number of carbon atoms[2] of 5 or 6, examples of which include a cyclopentyl group and a cyclohexyl group.

[2] Translator's note: In the Japanese original document, the term for "ring members" and the term for "total number of carbon atom" are used in the same phrase to specify the conditions being preferred, where only one or the other would be expected. Our translation faithfully reflects the Japanese source text.

The alkenyl group expressed by $R_{T3}'$, $R_{T3}$, $R_{T4}$, $R_{T5}$, and $R_{T6}$ preferably has a carbon number of 2 to 30, more preferably a carbon number of 2 to 20, and particularly preferably a carbon number of 2 to 10, examples including, a vinyl, aryl, 1-propenyl, 1-isopropenyl, 1-butenyl, 2-butenyl, and 3-pentenyl.

The alkynyl group expressed by $R_{T3}'$, $R_{T3}$, $R_{T4}$, $R_{T5}$, and $R_{T6}$ preferably has a carbon number of 2 to 30, more preferably a carbon number of 2 to 20, and particularly preferably a carbon number of 2 to 10, examples including an ethynyl, propargyl, 1-propynyl, and 3-pentynyl.

The aryl group expressed by $R_{T3}'$, $R_{T3}$, $R_{T4}$, $R_{T5}$, and $R_{T6}$ is preferably a substituted or unsubstituted aryl group with a carbon number of 6 to 30, examples including a phenyl group, tolyl group, and naphthyl group.

The heteroaryl group expressed by $R_{T3}'$, $R_{T3}$, $R_{T4}$, $R_{T5}$, and $R_{T6}$ is preferably a heteroaryl group with a carbon number of 5 to 8 and more preferably a substituted or unsubstituted heteroaryl group with 5 or 6 members, examples including a pyridyl group, a pyrazinyl group, a pyridazinyl group, a pyrimidinyl group, a triazinyl group, a quinolinyl group, an isoquinolinyl group, a quinazolinyl group, a cinnolinyl group, a phthalazinyl group, a quinoxalinyl group, pyrrolyl group, an indolyl group, a furyl group, a benzofuryl group, a thienyl group, a benzothienyl group, a pyrazolyl group, an imidazolyl group, a benzimidazolyl group, a triazolyl group, an oxazolyl group, a benzoxazolyl group, a thiazolyl group, a benzothiazolyl group, an isothiazolyl group, a benzisothiazolyl group, a thiadiazolyl group, an isoxazolyl group, a benzisoxazolyl group, a pyrrolidinyl group, a piperidinyl group, a piperazinyl group, an imidazolidinyl group, a thiazolinyl group, a sulfolanyl group, a carbazolyl group, a dibenzofuryl group, a dibenzothienyl group, and a pyridoindolyl group. Preferable examples are a pyridyl group, a pyrimidinyl group, an imidazolyl group, and a thienyl group, and more preferable are a pyridyl group and a pyrimidinyl group.

$R_{T3}'$, $R_{T3}$, $R_{T4}$, $R_{T5}$, and $R_{T6}$ are preferably a hydrogen atom, an alkyl group, a cyano group, a trifluoromethyl group, a perfluoroalkyl group, a dialkylamino group, a fluorine atom, an aryl group, or a heteroaryl group, more preferably a hydrogen atom, an alkyl group, a cyano group, a trifluoromethyl group, a fluorine atom, or an aryl group, and even more preferably a hydrogen atom, an alkyl group, or an aryl group. The substituent T is preferably an alkyl group, an alkoxy group, a fluorine atom, a cyano group, or a dialkylamino group and more preferably a hydrogen atom.

Any adjacent two of $R_{T3}$, $R_{T4}$, $R_{T5}$, and $R_{T6}$ may bind together to form a condensed four- to seven-member ring, and a condensed four- to seven-member ring is preferably formed by $R_{T3}$ and $R_{T4}$ binding to each other. This condensed four- to seven-member ring is a cycloalkyl, an aryl, or a heteroaryl, and this condensed four- to seven-member ring may further have a substituent, and preferably may have the substituent T. The definition and preferred ranges for the cycloalkyl, aryl, or heteroaryl thus formed are the same as for the cycloalkyl group, aryl group, and heteroaryl group defined by $R_{T3}'$, $R_{T3}$, $R_{T4}$, $R_{T5}$, and $R_{T6}$.

Examples of the aromatic heterocycle expressed by the ring Q include a pyridine ring, a pyrazine ring, a pyrimidine ring, a pyrazole ring, an imidazole ring, a triazole ring, an oxazole ring, an oxadiazole ring, a thiazole ring, and a thiadiazole ring. A pyridine ring and a pyrazine ring are preferred, with a pyridine ring being more preferred.

Examples of the condensed aromatic heterocycle expressed by the ring Q include a quinoline ring, an isoquinoline ring, and a quinoxaline ring. A quinoline ring and an isoquinoline ring are preferred, with a quinoline ring being more preferred.

m is preferably 1 to 3 and more preferably 2 or 3. Specifically, n is preferably either or 1. The ligand in the complex is preferably constituted by one or two types and more preferably by one type. When a reactive group is introduced into the complex molecule, it is also preferable for the ligand to be composed of two types from the standpoint of ease of synthesis.

The metal complex expressed by General Formula T-1 may be constituted by a combination of a ligand expressed by General Formula T-1-A below in General Formula T-1 or a tautomer thereof and a ligand expressed by (X—Y) or a tautomer thereof or all the ligands of this metal complex may be constituted only by a ligand expressed by General Formula T-1-A below or a tautomer thereof.

[Twentieth Chemical Formula]

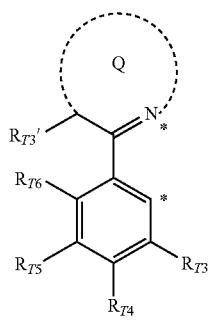

(T-1-A)

(In General Formula T-1-A, $R_{T3}'$, $R_{T3}$, $R_{T4}$, $R_{T5}$, $R_{T6}$, and Q are defined the same as $R_{T3}'$, $R_{T3}$, $R_{T4}$, $R_{T5}$, $R_{T6}$, and Q in General Formula T-1. The asterisk indicates the coordination position to iridium.)

There may further be a ligand known to a person skilled in the art as a so-called ligand (also called a coordination compound), which is used in the formation of metal complexes in known prior art, as a ligand expressed by (X—Y) as needed.

Various ligands are known as ligands used in the formation of metal complexes in known prior art, examples of which include the ligands described in "Photochemistry and Photophysics of Coordination Compounds," by H. Yersin, Springer-Verlag Co. (1987), and the ligands described in "Organometallic Chemistry-Fundamental and Application." by Akio Yamamoto; Shokabo Publishing Co. (1982) (for example, halogen ligands, (preferably a chlorine ligand), nitrogen-containing heteroaryl ligands (such as bipyridyl and phenanthroline), and diketone ligands (such as acetylacetone)). A ligand expressed by (X—Y) is preferably a diketone or a picolinic acid derivative, and from the standpoints of obtaining stability and high luminous efficiency of the complex, the acetylacetonate (acac) shown below is most preferable.

[Twenty-First Chemical Formula]

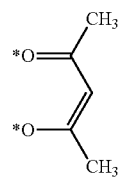

acac

The asterisk indicates the coordination position to iridium.

Concrete examples of ligands expressed by (X—Y) will be given below, but the present invention is not limited to or by these.

[Twenty-Second Chemical Formula]

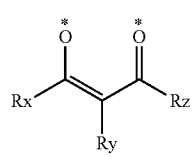

(I-1)

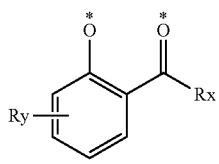

(I-2)

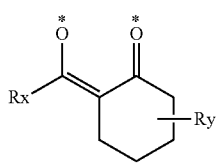

(I-3)

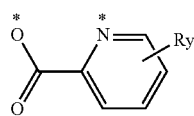

(I-4)

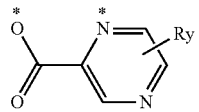

(I-5)

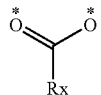

(I-6)

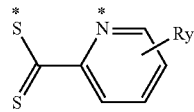

(I-7)

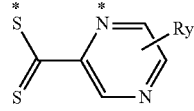

(I-8)

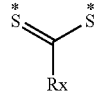

(I-9)

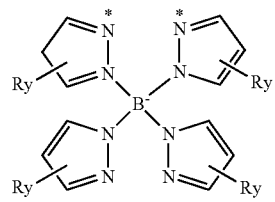

(I-10)

-continued

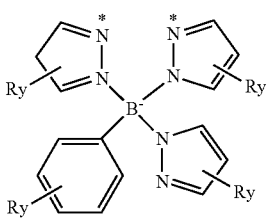 (I-11)

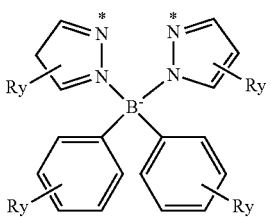 (I-12)

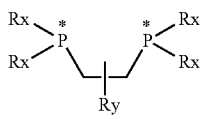 (I-13)

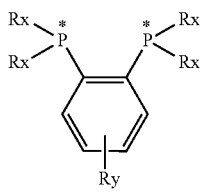 (I-14)

In the examples of ligands expressed by (X—Y) above, the asterisk indicates the coordination position to iridium in General Formula T-1. Rx, Ry, and Rz represent each independently a hydrogen atom or a substituent. Substituents selected from the aforementioned Substituent Group A can be used as this substituent. Preferably, Rx and Rz are each independently an alkyl group, a perfluoroalkyl group, a fluorine atom, or an aryl group, more preferably an alkyl group with a carbon number of 1 to 4, a perfluoroalkyl group with a carbon number of 1 to 4, a fluorine atom, or a phenyl group which may be substituted, and most preferably a methyl group, an ethyl group, a trifluoromethyl group, a fluorine atom, or a phenyl group. Ry is preferably a hydrogen atom, an alkyl group, a perfluoroalkyl group, a fluorine atom, or an aryl group, more preferably a hydrogen atom, an alkyl group with a carbon number of 1 to 4, or a phenyl group which may be substituted, and most preferably a hydrogen atom or a methyl group. It is conceivable that these ligands will not be a site where charges are transported in an element or where electrons are concentrated by excitation, so it is sufficient if Rx, Ry, and Rz are a chemically stable substituent, and there is no influence on the effect of the present invention. For the complex to be easily synthesized, I-1, I-4, and I-5 are preferable, and I-1 is most preferable. A complex having these ligands may be synthesized in the same manner as in known synthesis examples in which a corresponding ligand precursor is used. For example, [such a complex] can be synthesized by the method shown below by using commercially available difluoroacetylacetone, just as in the method described on page 46 of WO 2009-073245, for example.

[Twenty-Third Chemical Formula]

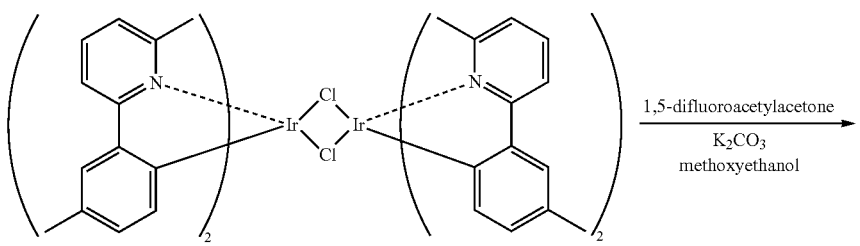

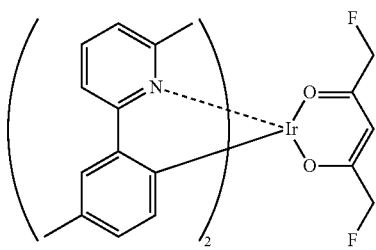

The monoanionic ligand shown in General Formula I-15 can also be used as a ligand.

[Twenty-Fourth Chemical Formula]

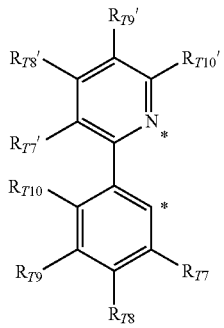

(I-15)

$R_{T7}$ to $R_{T10}$ in General Formula I-15 are defined the same as $R_{T3}$ to $R_{T6}$ in General Formula T-1, and the preferred ranges are also the same. $R_{T7}'$ to $R_{T10}'$ are defined the same as $R_{T3}'$, and the preferred ranges are also the same as that of $R_{T3}'$. The asterisk indicates the coordination position to iridium.

The compound expressed by General Formula T-1 above is preferably a compound expressed by General Formula T-2 below,

[Twenty-Fifth Chemical Formula]

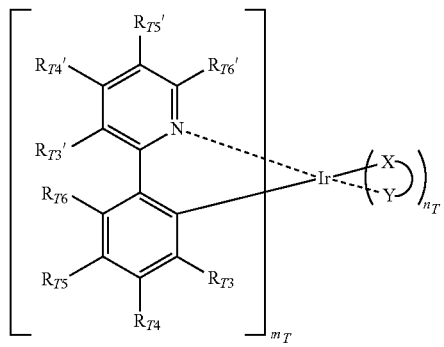

(T-2)

(In General Formula T-2, $R_{T3}'$ to $R_{T6}'$ and $R_{T3}$ to $R_{T6}$ represent each independently a hydrogen atom, an alkyl group, an alkenyl group, an alkynyl group, a perfluoroalkyl group, a trifluorovinyl group, —$CO_2R_T$, —$C(O)R_T$, —$N(R_T)_2$, —$NO_2$, —$OR_T$, a fluorine atom, an aryl group, or a heteroaryl group, and may further have a substituent T.

Any adjacent two of $R_{T3}$, $R_{T4}$, $R_{T5}$, and $R_{T6}$ may bind together to form a condensed four-to seven-member ring, and this condensed four- to seven-member ring may further have a substituent T.

$R_{T3}'$ and $R_T$ may form a ring by being linked by a linking group selected from among —$C(R_T)_2$—$C(R_T)_2$—, —$CR_T$=$CR_T$—, —$C(R_T)_2$—, —O—, —$NR_T$—, —O—C($R_T)_2$—, —$NR_T$—$C(R_T)_2$—, and —N=$CR_T$—.

The $R_T$ [groups] represent each independently a hydrogen atom, an alkyl group, an alkenyl group, an alkynyl group, an aryl group, or a heteroaryl group, and may further have a substituent T.

The substituents T represent each independently a fluorine atom, —R', —OR', —N(R')$_2$, —SR', —C(O)R', —C(O)OR', —C(O)N(R')$_2$, —SO$_2$, —SOR', —SO$_2$R', or —SO$_3$R', and the R' [groups] represent each independently a hydrogen atom, an alkyl group, a perfluoroalkyl group, an alkenyl group, an alkynyl group, an aryl group, or a heteroaryl group.

(X—Y) represents a ligand, $m_T$ is an integer of 1 to 3, $n_T$ is an integer of 0 to 2, and $m_T$+$n_T$ is 3.)

Preferred ranges for $R_{T3}'$, $R_{T3}$ to $R_{T6}$, (X—Y), $m_T$, and $n_T$ in General Formula T-2 are the same as the preferred ranges for $R_{T3}'$, $R_{T3}$ to $R_{T6}$, (X—Y), m, and n in General Formula T-1.

$R_{T4}'$ is preferably a hydrogen atom, an alkyl group, an aryl group, or a fluorine atom and more preferably a hydrogen atom.

It is preferable for $R_{T5}'$ and $R_{T6}'$ to be a hydrogen atom or to be bound to each other to form a condensed four- to seven-member cyclic group, and this condensed four- to seven-member cyclic group is more preferably a cycloalkyl, cycloheteroalkyl, aryl, or heteroaryl and even more preferably an aryl.

The substituent T in $R_{T4}'$ to $R_{T6}'$ is preferably an alkyl group, an alkoxy group, a fluorine atom, as cyano group, an alkylamino group, or a diarylamino group and more preferably an alkyl group.

One of the preferred forms of the compound expressed by General Formula T-2 above is when any adjacent two of $R_{T3}'$, $R_{T4}'$, $R_{T5}'$, $R_{T6}'$, $R_{T3}$, $R_{T4}$, $R_{T5}$, and $R_{T6}$ in General Formula T-2 are not bound to each other to form a condensed ring.

One of the preferred forms of the compound expressed by General Formula T-2 above is when [the compound] is expressed by General Formula T-3 below.

[Twenty-Sixth Chemical Formula]

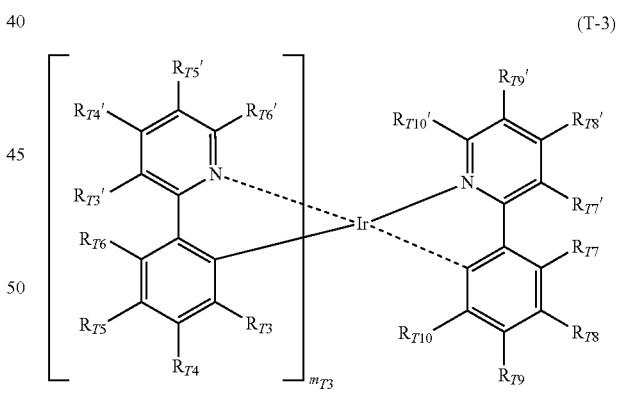

(T-3)

$R_{T3}'$ to $R_{T6}'$ and $R_{T3}$ to $R_{T6}$ in General Formula T-3 are defined the same as $R_{T3}'$ to $R_{T6}'$ and $R_{T3}$ to $R_{T6}$ in General Formula T-2, and the preferred ranges are also the same.

$m_{T3}$ represents 2.

$R_{T7}$ to $R_{T10}$ are defined the same as $R_{T3}$ to $R_{T6}$, and the preferred ranges are also the same. $R_{T7}'$ to $R_{T10}'$ are defined the same as $R_{T3}'$ to $R_{T6}'$, and the preferred ranges are also the same.

Another preferred form of the compound expressed by General Formula T-2 above is a compound expressed by General Formula T-4 below.

[Twenty-Seventh Chemical Formula]

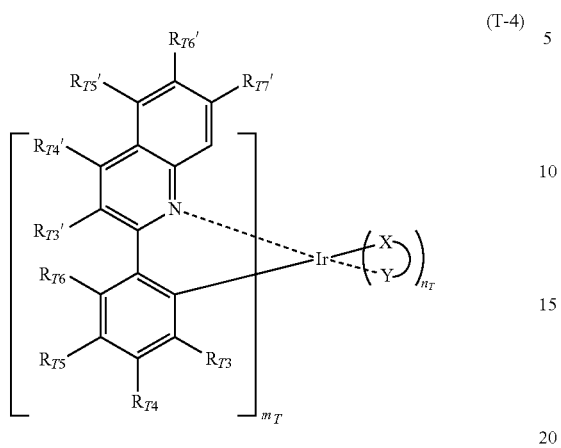

(T-4)

$R_{T3}'$ to $R_{T7}'$, $R_{T3}$ to $R_{T6}$, (X—Y), $m_T$, and $n_T$ in General Formula T-4 are defined the same as $R_{T3}'$ to $R_{T6}'$, $R_{T3}$ to $R_{T6}$, (X—Y), $m_T$, and $m_T$ in General Formula T-2, and the preferred ranges are also the same. It is particularly preferable if from zero to two of $R_{T3}'$ to $R_{T6}'$ and $R_{T3}$ to $R_{T6}$ are an alkyl group or a phenyl group and the rest are all a hydrogen atom, and it is even more preferable if one or two of $R_{T3}'$ to $R_{T6}'$ and $R_{T3}$ to $R_{T6}$ are an alkyl group and the rest are all a hydrogen atom.

Another preferred form of the compound expressed by General Formula T-2 above is a compound expressed by General Formula T-5 below.

[Twenty-Eighth Chemical Formula]

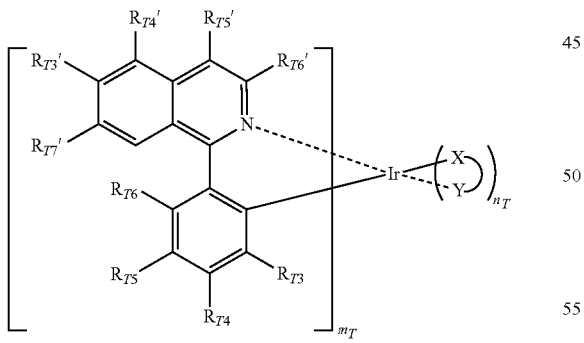

(T-5)

$R_{T3}'$ to $R_{T7}'$, $R_{T3}$ to and $R_{T6}$, (X—Y), $m_T$, and $n_T$ in General Formula T-5 are defined the same as $R_{T3}'$ to $R_{T6}'$, $R_{T3}$ to $R_{T6}$, (X—Y), $m_T$, and $n_T$ in General Formula T-2, and the preferred ranges are also the same.

Preferred concrete examples of the compound expressed by General Formula T-1 are given below, but [compound] is not limited to these.

[Twenty-Ninth Chemical Formula]

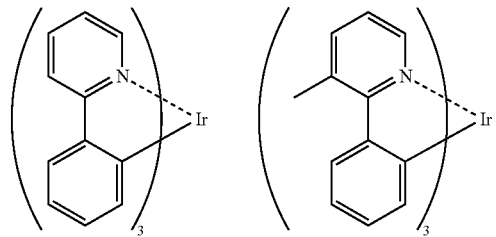

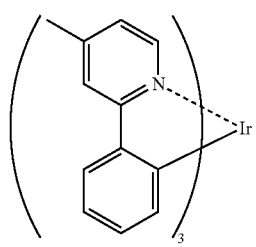

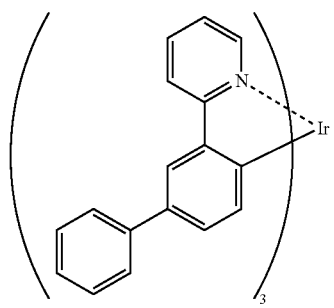

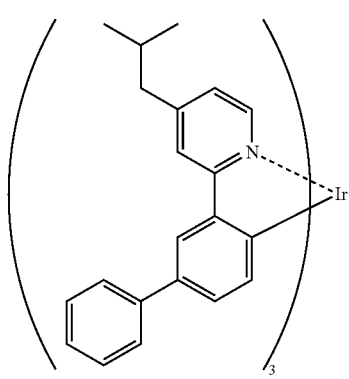

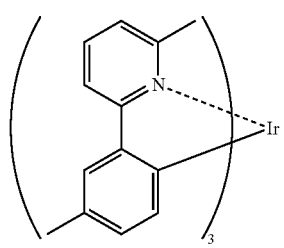

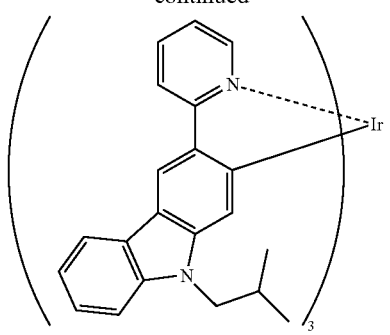
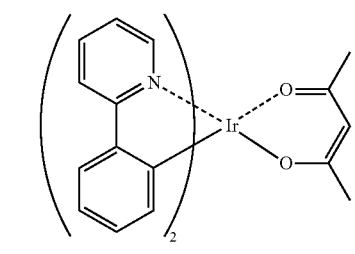
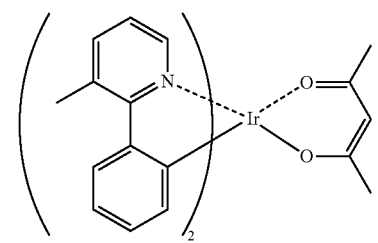
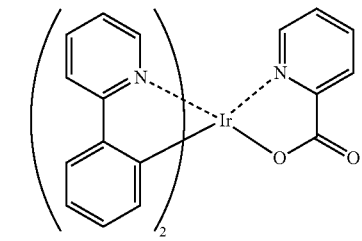
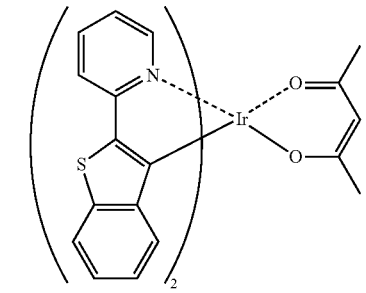
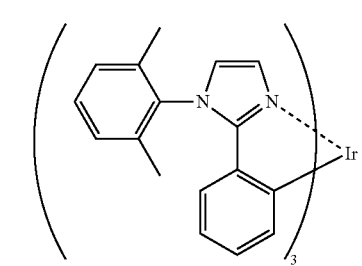
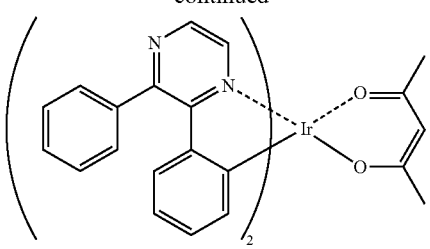
[Thirtieth Chemical Formula]
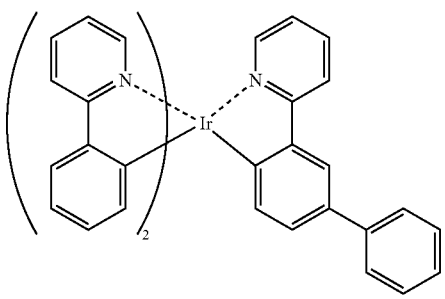
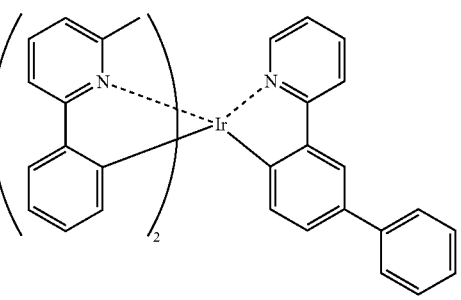
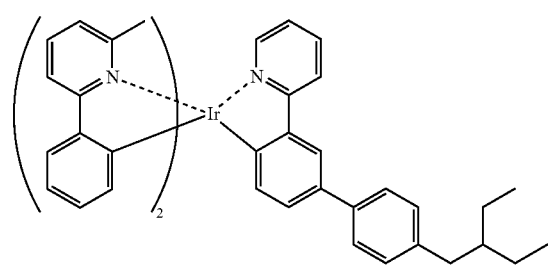
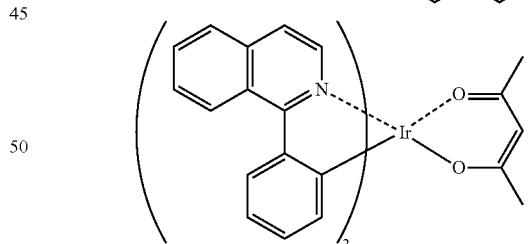
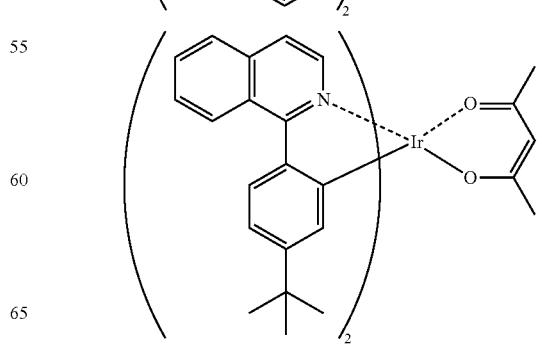

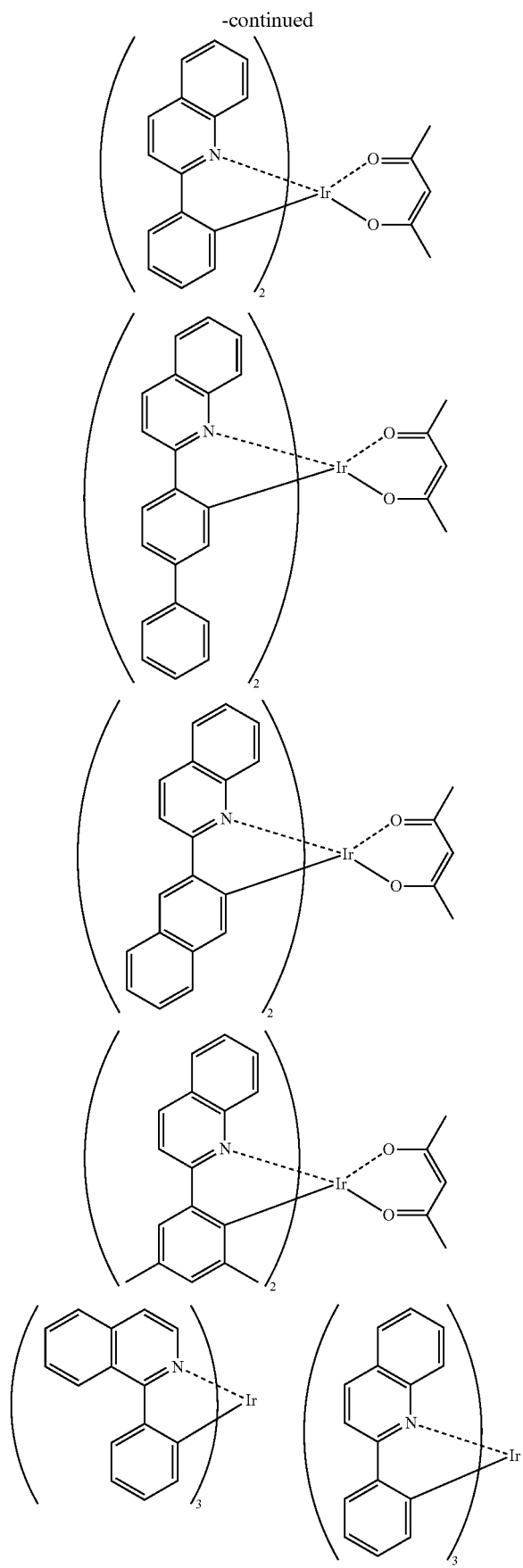

The compounds given as examples of the compound expressed by General Formula T-1 above can be synthesized by the method described in Japanese Laid-Open Patent Application 2009-99783, or by the various methods described in U.S. Pat. No. 7,279,232 and the like. After synthesis, it is preferable for purification by column chromatography, recrystallization, or the like to be performed, followed by sublimation purification. Sublimation purification not only allows organic impurities to be separated, but also allows inorganic salts, residual solvents, and the like to be effectively removed.

The compound expressed by General Formula T-1 is contained in the light-emitting layer, but its application is not limited [to this], and [the compound] may be further contained in any of the organic layers.

The light-emitting material in the light-emitting layer is generally contained in the light-emitting layer in an amount of 0.1 to 50 wt % with respect to the total weight of the compounds which form the light-emitting layer, and from the standpoints of durability and external quantum efficiency, [the material] is preferably contained in an amount of 1 to 50 wt %, and even more preferably contained in an amount of 2 to 40 wt %.

There are no particular restrictions on the thickness of the light-emitting layer, 2 to 500 nm is usually preferable, and from the standpoint of external quantum efficiency, [a thickness of] 3 to 200 nm is more preferable, and 5 to 100 nm is even more preferable.

The light-emitting layer in the element of the present invention may be made up of a mixed layer of a host material and a light-emitting material. The light-emitting material may be a fluorescent material or a phosphorescent material and may include just one kind of dopant or two or more kinds. The host material is preferably a charge transport material. There may be just one kind of host material, or two or more kinds may be used. Examples include a mixture of an electron transporting host material and a hole transporting host material. Furthermore, a material which does not have a charge transporting property and does not emit light may be included in the light-emitting layer.

Moreover, the light-emitting layer may be a single layer or a multilayer of two or more layers. In addition, each light-emitting layer may also emit light of a different color.

In the present invention, the compound expressed by General Formula T-1 is included in the light-emitting layer for the purpose of enhancing luminous efficiency and durability (and particularly durability during high-temperature drive), but its application is not limited [to this], and [the compound] may be contained in any of the organic layers in addition to the light-emitting layer. Besides the light-emitting layer, it is preferable that the layer into which the compound expressed by General Formula T-1 is introduced be one of the hole injection layer, the hole transport layer, the electron transport layer, the electron injection layer, the exciton blocking layer, and the charge blocking layer, or that [the compound] be contained in a plurality [of these layers]

(Composition Containing the Compound Expressed by General Formula 1 and the Compound Expressed by General Formula T-1)

The present invention also relates to a composition containing the compound expressed by General Formula 1 above and the compound expressed by General Formula T-1 above.

The amount in which the compound expressed by General Formula 1 is contained in the composition of the present invention is preferably 50 to 99 wt % and more preferably 70 to 95 wt %.

The amount in which the compound expressed by General Formula T-1 is contained in the composition of the present invention is preferably 1 to 30 wt % and more preferably 5 to 15 wt %.

Other components that may be contained in the composition of the present invention may be either organic or inorganic, and the materials listed as examples of the host material, fluorescent material, and phosphorescent material (discussed later) can be used as organics.

The composition of the present invention can form the organic layer of an organic electroluminescent element by vapor deposition, sputtering, or another such dry film formation method, or by transfer, printing, or the like.

Next, General Formula C-1 will be described.

[Thirty-First Chemical Formula]

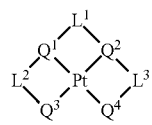

(C-1)

(In General Formula C-1, $Q^1$, $Q^2$, $Q^3$, and $Q^4$ represent each independently a ligand coordinated to platinum. $L^1$, $L^2$, and $L^3$ represent each independently a single bond or a divalent linking group.)

General Formula C-1 will now be described.

$Q^1$, $Q^2$, $Q^3$, and $Q^4$ represent each independently a ligand coordinated to platinum. The bonds between the platinum and $Q^1$, $Q^2$, $Q^3$, and $Q^4$ here may be covalent bonds, ion bonds, coordination bonds, or the like. The atom in $Q^1$, $Q^2$, $Q^3$, and $Q^4$ that is bound to the platinum is preferably a carbon atom, a nitrogen atom, an oxygen atom, a sulfur atom, or a phosphoms atom. Of the atoms in $Q^1$, $Q^2$, $Q^3$, and $Q^4$ that are bound to the platinum, at least one is preferably a carbon atom, more preferably two are carbon atoms, and it is particularly preferable if two are carbon atoms and two are nitrogen atoms.

$Q^1$, $Q^2$, $Q^3$, and $Q^4$ bound to platinum by a carbon atom may be either an anionic ligand or a neutral ligand. Examples of anionic ligands include a vinyl ligand, an aromatic hydrocarbon ring ligand (such as a benzene ligand, a naphthalene ligand, an anthracene ligand, and a phenanthrene ligand), a heterocyclic ligand (such as a furan ligand, a thiophene ligand, a pyridine ligand, a pyrazine ligand, a pyrimidine ligand, a pyridazine ligand, a triazine ligand, a thiazole ligand, an oxazole ligand, a pyrrole ligand, an imidazole ligand, a pyrazole ligand, and a triazole ligand, as well as condensed rings containing these [ligands] (such as a quinoline ligand or a benzothiazole ligand)). Examples of neutral ligands include a carbene ligand.

$Q^1$, $Q^2$, $Q^3$, and $Q^4$ bound to platinum by a nitrogen atom may be either a neutral ligand or an anionic ligand. Examples of neutral ligands include a nitrogen-containing aromatic heterocyclic ligand (such as a pyridine ligand, a pyrazine ligand, a pyrimidine ligand, a pyridazine ligand, a triazine ligand, an imidazole ligand, a pyrazole ligand, a triazole ligand, an oxazole ligand, and a thiazole ligand, as well as condensed rings containing these [ligands] (such as a quinoline ligand or a benzimidazole ligand)), an amine ligand, a nitrile ligand, and an imine ligand Examples of anionic ligands include an amino ligand, an imino ligand, and a nitrogen-containing aromatic heterocyclic ligand such as a pyrrole ligand, an imidazole ligand, and a triazole ligand, as well as condensed rings containing these [ligands] such as an indole ligand or a benzimidazole ligand)).

$Q^1$, $Q^2$, $Q^3$, and $Q^4$ bound to platinum by an oxygen atom may be either a neutral ligand or an anionic ligand. Examples of neutral ligands include an ether ligand, a ketone ligand, an ester ligand, an amide ligand, and an oxygen-containing heterocyclic ligand (such as a furan ligand or an oxazole ligand, as well as condensed rings containing these [ligands] (such as a benzoxazole ligand)). Examples of anionic ligands include an alkoxy ligand, an aryloxy a heteroaryloxy ligand, an acyloxy ligand, and a silyloxy ligand.

$Q^1$, $Q^2$, $Q^3$, and $Q^4$ bound to platinum by a sulfur atom may be either a neutral ligand or an anionic ligand. Examples of neutral ligands include a thioether ligand, a thioketone ligand, a thioester ligand, a thioamide ligand, and a sulfur-containing heterocyclic ligand (such as a thiophene ligand or a thiazole ligand, as well as condensed rings containing these [ligands] (such as a benzothiazole ligand)). Examples of anionic ligands include an alkylmercapto ligand, an arylmercapto ligand, and a heteroarylmercapto ligand.

$Q^1$, $Q^2$, $Q^3$, and $Q^4$ bound to platinum by a phosphorus atom may be either a neutral ligand or an anionic ligand. Examples of neutral ligands include a phosphine ligand, a phosphate ligand, a phosphite ligand, and a phosphorus-containing heterocyclic ligand such as a phosphinine ligand). Examples of anionic ligands include a phosphino ligand, a phosphinyl ligand, and a phosphoryl ligand.

The groups represented by $Q^1$, $Q^2$, $Q^3$, and $Q^4$ may have a substituent, and those listed as the aforementioned Substituent Group A can be used as needed as the substituent. Furthermore, the substituents may be linked to each other (if $Q^3$ and $Q^4$ are linked, the result is a platinum complex of a cyclic tetradentate ligand).

The groups expressed by $Q^1$, $Q^2$, $Q^3$, and $Q^4$ are preferably an aromatic hydrocarbon ring ligand bound to platinum by a carbon atom, an aromatic heterocyclic ligand bound to platinum by a carbon atom, a nitrogen-containing aromatic heterocyclic ligand bound to platinum by a nitrogen atom, an acyloxy ligand, an alkyloxy ligand, an aryloxy ligand, a heteroaryloxy ligand, or a silyloxy ligand, more preferably an aromatic hydrocarbon ring liga bound to platinum by a carbon atom, an aromatic heterocyclic ligand bound to platinum by a carbon atom, a nitrogen-containing aromatic heterocyclic ligand bound to platinum by a nitrogen atom, an acyloxy ligand, or an aryloxy ligand, and even more preferably an aromatic hydrocarbon ring ligand bound to platinum by a carbon atom, an aromatic heterocyclic ligand bound to platinum by a carbon atom, a nitrogen-containing aromatic heterocyclic ligand bound to platinum by a nitrogen atom, or an acyloxy ligand.

$L^1$, $L^2$, and $L^3$ represent a single bond or a divalent linking group. Examples of the divalent linking group expressed by $L^1$, $L^2$, and $L^3$ include alkylene groups (such as methylene, ethylene, and propylene), arylene groups (phenylene and naphthalenediyl), heteroarylene groups (such as pyridinediyl and thiophenediyl), imino groups (—$NR_L$—) (such as a phenylimino group), an oxy group (–O—), a thio group (—S—), phosphinidene groups (—$PR_L$—) (such as a phenylphosphinidene group), and silylene groups (—$SiR_LR_L'$—) (such as a dimethylsilylene group and diphenylsilylene group), as well as combinations of these. Here, examples of $R_L$ and $R_L'$ include alkyl groups and aryl groups. These linking groups may further have a substituent. As the substituent, those listed as the aforementioned Substituent Group A can be used as needed.

From the standpoints of stability of the complex and luminescent quantum yield, $L^1$, $L^2$, and $L^3$ are preferably a single bond, an alkylene group, an arylene group, a heteroarylene group, an imino group, an oxy group, a thin group, or a silylene group, more preferably a single bond, an alkylene group, an arylene group, or an imino group, even more preferably a single bond, an alkylene group, or an arylene group, still more preferably a single bond, a methylene group, or a phenylene group, still more preferably a single bond or a di-substituted methylene group, still more preferably a single bond, a dimethylmethylene group, a diethylmethylene group, a diisobutylmethylene group, a dibenzylmethylene group, an ethylmethylmethylene group, a methylpropylmethylene group, an isobutylmethylmethylene group, a diphenylmethylene group, a methylphenylmethylene group, a cyclohexanediyl group, a cyclopentanediyl group, a fluorenediyl group, or a fluoromethylmethylene group, and particularly preferably a single bond, a dimethylmethylene group, a diphenylmethylene group, or a cyclohexanediyl group.

The platinum complex expressed by General Formula C-1 is more preferably a platinum complex expressed by General Formula C-2 below.

[Thirty-Second Chemical Formula]

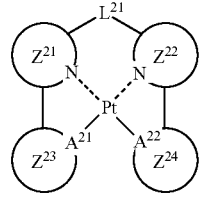

(C-2)

In General Formula C-2, $L^{21}$ represents a single bond or a divalent linking group. $A^{21}$ and $A^{22}$ represent each independently a carbon atom or a nitrogen atom. $Z^{21}$ and $Z^{22}$ represent each independently a nitrogen-containing aromatic heterocycle. $Z^{23}$ and $Z^{24}$ represent each independently a benzene ring or an aromatic heterocycle.

General Formula C-2 will now be described.

$L^{21}$ is defined the same as $L^1$ in General Formula C-1 above, and the preferred ranges are also the same.

$A^{21}$ and $A^{22}$ represent each independently a carbon atom or a nitrogen atom. At least one of $A^{21}$ and $A^{22}$ is preferably a carbon atom. From the standpoint of stability of the complex and the standpoint of luminescent quantum yield of the complex, it is preferable if $A^{21}$ and $A^{22}$ are both a carbon atom.

$Z^{21}$ and $Z^{22}$ represent each independently a nitrogen-containing aromatic heterocycle. Examples of the nitrogen-containing aromatic heterocycle expressed by $Z^{21}$ and $Z^{22}$ a pyridine ring, a pyrimidine ring, a pyrazine ring, a triazine ring, an imidazole ring, a pyrazole ring, an oxazole ring, a thiazole ring, a triazole ring, an oxadiazole ring, and a thiadiazole ring. From the standpoints of stability of the complex, control of emission wavelength, and luminescent quantum yield, the ring expressed by $Z^{21}$ and $Z^{22}$ is preferably a pyridine ring, a pyrazine ring, an imidazole ring, or a pyrazole ring, more preferably a pyridine ring, an imidazole ring, or a pyrazole ring, even more preferably a pyridine ring or a pyrazole ring, and particularly preferably a pyridine ring.

The aforementioned nitrogen-containing aromatic heterocycle expressed by $Z^{21}$ and $Z^{22}$ may have a substituent. [A group from] the aforementioned Substituent Group A can be used as a substituent on a carbon atom, and [a group from] the aforementioned Substituent Group B [sic]³ can be used as a substituent on a nitrogen atom. The substituent on a carbon atom is preferably an alkyl group, a perfluoroalkyl group, an aryl group, an aromatic heterocyclic group, a dialkylamino group, a diarylamino group, an alkoxy group, a cyano group, or a halogen atom. The substituent can be suitably selected for the purpose of controlling the emission wavelength or potential, but if the wavelength is to be shortened, [the substituent is] preferably an electron donating group, a fluorine atom, or an aromatic ring group; for example, an alkyl group, a dialkylamino group, an alkoxy group, a fluorine atom, an aryl group, an aromatic heterocyclic group, or the like is selected. Furthermore, if the wavelength is to be lengthened, [the substituent is] preferably an electron withdrawing group; for example, a cyano group, a perfluoroalkyl group, or the like is selected. The substituent on a nitrogen atom is preferably an alkyl group, an aryl group, or an aromatic heterocyclic group, and from the standpoint of stability of the complex, an alkyl group or an aryl group is preferable. The aforementioned substituents may be linked to each other to form a condensed ring.

Examples of the ring thus formed include a benzene ring, a pyridine ring, a pyrazine ring a pyridazine ring, a pyrimidine ring, an imidazole ring, an oxazole ring, a thiazole ring, a pyrazole ring, a thiophene ring, and a furan ring.

[3] Translator's note: The Japanese source text literally reads "the aforementioned Substituent Group B" here, but no such Substituent Group B has been mentioned thus far.

$Z^{23}$ and $Z^{24}$ represent each independently a benzene ring or an aromatic heterocycle. Examples of the nitrogen-containing aromatic heterocycle expressed by $Z^{23}$ and $Z^{24}$ include a pyridine ring, a pyrimidine ring, a pyrazine ring, a pyridazine ring, a triazine ring, an imidazole ring, a pyrazole ring, an oxazole ring, a thiazole ring, a triazole ring, an oxadiazole ring, a thiadiazole ring, a thiophene ring, and a furan ring. From the standpoints of stability of the complex, control of emission wavelength, and luminescent quantum yield, the ring expressed by $Z^{23}$ and $Z^{24}$ is preferably a benzene ring, a pyridine ring, a pyrazine ring, an imidazole ring, a pyrazole ring, or a thiophene ring, more preferably a benzene ring, a pyridine ring, or a pyrazole ring, and even more preferably a benzene ring or a pyridine ring.

The aforementioned benzene ring or nitrogen-containing aromatic heterocycle expressed by $Z^{23}$ and $Z^{24}$ may have a substituent. [A group from] the aforementioned Substituent Group A can be used as a substituent on a carbon atom, and [a group from] the aforementioned Substituent Group B can be used as a substituent on a nitrogen atom. The substituent on a carbon atom is preferably an alkyl group, a perfluoroalkyl group, an aryl group, an aromatic heterocyclic group, a dialkylamino group, a diarylamino group, an alkoxy group, a cyano group, or a halogen atom. The substituent can be suitably selected for the purpose of controlling the emission wavelength or potential, but if the wavelength is to be lengthened, [the substituent is] preferably an electron donating group or an aromatic, ring group; for example, an alkyl group, a dialkylamino group, an alkoxy group, an aryl group, an aromatic heterocyclic group, or the like is selected. Moreover, if the wavelength, is to be shortened, [the substituent is] preferably an electron withdrawing group; for example, a fluorine atom, a cyano group, a pert perfluoroalkyl group, or the like is selected. A substituent on a nitrogen atom is preferably an alkyl group, an aryl group, or an aromatic heterocyclic group, and from the standpoint of stability of the complex, an alkyl group or an aryl group is preferable. The aforementioned substituents may be linked to each other to form a condensed ring. Examples of the ring thus formed include a benzene ring, a pyridine ring, a pyrazine ring, a pyridazine ring, a pyrimidine ring, an imidazole ring, an oxazole ring, a thiazole ring, a pyrazole ring, a thiophene ring, and a furan ring.

Of the platinum complexes expressed by General Formula C-2, one of the more preferred forms is a platinum complex expressed by General Formula C-3 below.

[Thirty-Third Chemical Formula]

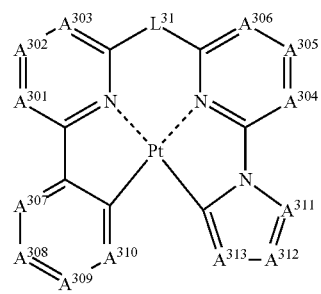

(C-3)

In the General Formula C-3, $A^{301}$ to $A^{313}$ represent each independently C—R or a nitrogen atom. R represents a hydrogen atom or a substituent. $L^{31}$ represents a single bond or a divalent linking group.

General Formula C-3 will now be described.

$L^{31}$ is defined the same as $L^{21}$ in General Formula C-2, and the preferred ranges are also the same.

$A^{301}$ to $A^{306}$ represent each independently C—R or a nitrogen atom. R represents a hydrogen atom or a substituent. Those listed as the aforementioned Substituent Group A can be used as the substituent expressed by R. $A^{301}$ to $A^{306}$ are preferably C—R, and the R [groups] may be linked together to form a ring. If $A^{301}$ to $A^{306}$ are C—R, the R [groups] of $A^{302}$ and $A^{305}$ are preferably a hydrogen atom, an alkyl group, an aryl group, an ammo group, an alkoxy group, an aryloxy group, a fluorine atom, or a cyano group, more preferably a hydrogen atom, an amino group, an alkoxy group, an aryloxy group, or a fluorine atom, and particularly preferably a hydrogen atom or a fluorine atom. The R [groups] of $A^{301}$, $A^{303}$, $A^{304}$, and $A^{306}$ are preferably a hydrogen atom, an alkyl group, an aryl group, an amino group, an alkoxy group, an aryloxy group, a fluorine atom, or a cyano group, more preferably a hydrogen atom, an amino group, an alkoxy group, an aryloxy group, or a fluorine atom, and particularly preferably a hydrogen atom.

$A^{307}$, $A^{308}$, $A^{309}$, and $A^{310}$ represent each independently C—R or a nitrogen atom. R represents a hydrogen atom or a substituent. As the substituent expressed by R, those listed as the aforementioned Substituent Group A can be used. When $A^{307}$, $A^{308}$, $A^{309}$, and $A^{310}$ are C—R, R is preferably a hydrogen atom, an alkyl group, a perfluoroalkyl group, an aryl group, an aromatic heterocyclic group, a dialkylamino group, a diarylamino group, an alkyloxy group, a cyano group, or a halogen atom, more preferably a hydrogen atom, an alkyl group, a perfluoroalkyl group, an aryl group, a dialkylamino group, a cyano group, or a fluorine atom, and even more preferably a hydrogen atom, an alkyl group, a trifluoromethyl group, or a fluorine atom. In addition, if possible, the substituents may be linked together to form a condensed ring structure. When the emission wavelength is shifted to the short wavelength side, $A^{308}$ is preferably a nitrogen atom.

When $A^{307}$ to $A^{310}$ are selected as described above, examples of a six-member ring formed by two carbon atoms and $A^{307}$, $A^{308}$, $A^{309}$, and $A^{310}$ include a pyridine ring, a pyrazine ring, a pyrimidine ring, a pyridazine ring, and a triazine ring, more preferably a pyridine ring, a pyrazine ring, a pyrimidine ring, and a pyridazine ring, and particularly preferably a pyridine ring. Having the aforementioned six-member ring be a pyridine ring, a pyrazine ring, a pyrimidine ring, or a pyridazine ring (with a pyridine ring being particularly preferable) is advantageous in that the acidity of hydrogen atoms located at positions where metal-carbon bonds are formed is increased over that in the case of a benzene ring, so a metal complex is formed more easily.

$A^{311}$, $A^{312}$, and $A^{313}$ represent each independently C—R or a nitrogen atom. R represents a hydrogen atom or a substituent. Those listed as the aforementioned Substituent Group A can be used as the substituent expressed by R. When $A^{311}$, $A^{312}$, and $A^{313}$ are C—R, R is preferably a hydrogen atom, an alkyl group, a perfluoroalkyl group, an aryl group, an aromatic heterocyclic group, a dialkylamino group, a diarylamino group, an alkyloxy group, a cyano group, or a halogen atom, more preferably a hydrogen atom, an alkyl group, a perfluoroalkyl group, an aryl group, a dialkylamino group, a cyano group, or a fluorine atom, and even more preferably a hydrogen atom, an alkyl group, a trifluoromethyl group, or a fluorine atom. Furthermore, if possible, the substituents may be linked together to form a condensed ring structure.

Examples of the five-member ring formed by $A^{311}$, $A^{312}$, and $A^{313}$ along with one nitrogen atom and one carbon atom include a pyrrole ring, a pyrazole ring, an imidazole ring, a furan ring, and a thiophene ring. [Of these], a pyrrole ring, a pyrazole ring, and an imidazole ring are more preferable, and a pyrrole ring and a pyrazole ring are even more preferable. Having the aforementioned five-member ring be a pyrrole ring, a pyrazole ring, or an imidazole ring (even more preferably a pyrrole ring or a pyrazole ring) is advantageous in that stability of the metal complex is improved.

Of the platinum complexes expressed by General Formula C-2, one of the more preferred forms is a platinum complex expressed by General Formula C-4 below,

[Thirty-Fourth Chemical Formula]

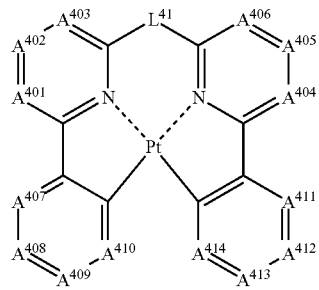

(C-4)

In General Formula C-4, $A^{401}$ to $A^{414}$ represent each independently C—R or a nitrogen atom. R represents a hydrogen atom or a substituent. $L^{41}$ represents a single bond or a divalent linking group.

General Formula C-4 will now be described.

$A^{401}$ to $A^{414}$ represent each independently C—R or a nitrogen atom. R represents a hydrogen atom or a substituent. $A^{401}$ to $A^{406}$ and $L^{41}$ are defined the same as $A^{301}$ to $A^{306}$ and $L^{31}$ in General Formula C-3 above, and the preferred ranges are also the same.

For $A^{407}$ to $A^{414}$, the number of nitrogen atoms in each of $A^{407}$ to $A^{410}$ and $A^{411}$ to $A^{414}$ is preferably 0 to 2 and more preferably 0 or 1. When the emission wavelength is shifted to the short wavelength side, $A^{408}$ and $A^{412}$ preferably a nitrogen atom, and $A^{408}$ and $A^{412}$ more preferably both a nitrogen atom.

When $A^{407}$ to $A^{414}$ represent C—R the R [groups] of $A^{408}$ and $A^{412}$ are preferably a hydrogen atom, an alkyl group, a perfluoroalkyl group, an aryl group, an amino group, an alkoxy group, an aryloxy group, a fluorine atom, or a cyano group, more preferably a hydrogen atom, a perfluoroalkyl group, an alkyl group, an aryl group, a fluorine atom, or a cyano group, and particularly preferably a hydrogen atom, a perfluoroalkyl group, or a cyano group. The R. [groups] expressed by $A^{407}$, $A^{409}$, $A^{411}$, and $A^{413}$ are preferably a hydrogen atom, an alkyl group, a perfluoroalkyl group, an aryl group, an amino group, an alkoxy group, an aryloxy group, a fluorine atom, or a cyano group, more preferably a hydrogen atom, a perfluoroalkyl group, a fluorine atom, or a cyano group, and particularly preferably a hydrogen atom or a fluorine atom. The R [groups] expressed by $A^{410}$ and $A^{414}$ are preferably a hydrogen atom or a fluorine atom and more preferably a hydrogen atom. When any one of $A^{407}$ to $A^{409}$ and $A^{411}$ to $A^{413}$ represents C—R, the R [groups] may be linked together to form a ring.

Of the platinum complexes expressed by General Formula C-1, another more preferred form is a platinum complex expressed by General Formula C-5 below.

[Thirty-Fifth Chemical Formula]

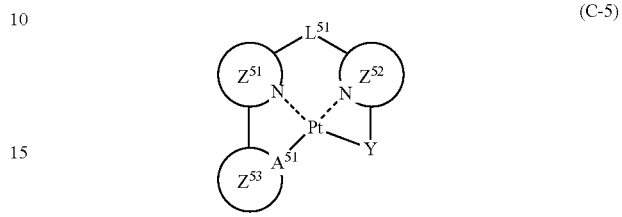

(C-5)

In General Formula C-5, $L^{51}$ represents a single bond or a divalent linking group. The $A^{51}$ [groups] represent each independently a carbon atom or a nitrogen atom. $Z^{51}$ and $Z^{52}$ represent each independently a nitrogen-containing aromatic heterocycle. The $Z^{53}$ [groups] represent each independently a benzene ring or an aromatic heterocycle. Y is an anionic acyclic ligand bound to platinum.

General Formula C-5 will now be described.

$L^{51}$ is defined the same as $L^1$ in General Formula C-1 above, and the preferred ranges are also the same.

$A^{51}$ represents a carbon atom or a nitrogen atom. From the standpoint of stability of the complex and the standpoint of luminescent quantum yield, $A^{51}$ is preferably a carbon atom.

$Z^{51}$ and $Z^{52}$ are respectively defined the same as $Z^{21}$ and $Z^{22}$ in General Formula C-2 above, and the preferred ranges are also the same. $Z^{53}$ is defined the same as $Z^{23}$ in General Formula C-2 above, and the preferred ranges are also the same.

Y is an anionic acyclic ligand bound to platinum. An acyclic ligand is one in which the atom bound to platinum does not form a ring in a ligand state. The atom in Y that is bound to platinum is preferably a carbon atom, a nitrogen atom, an oxygen atom, or a sulfur atom, more preferably a nitrogen atom or an oxygen atom, and most preferably an oxygen atom. A vinyl ligand is an example of Y that is bound to platinum by a carbon atom. Examples of Y bound to platinum by a nitrogen atom include an amino ligand and an imino ligand. Examples of Y bound to platinum by an oxygen atom include an alkoxy ligand, an aryloxy ligand, a heteroaryloxy ligand, an acyloxy ligand, a silyloxy ligand, a carboxyl ligand, a phosphate ligand, and a sulfonate ligand. Examples of Y bound to platinum by a sulfur atom include an alkylmercapto ligand, an arylmercapto ligand, a heteroarylmercapto ligand, and a thiocarboxylate ligand.

The ligand expressed by Y may have a substituent. Those listed as the aforementioned Substituent Group A can be suitably used as the substituent. In addition, the substituents may linked together.

The ligand expressed by Y is preferably a ligand bound to platinum by an oxygen atom, more preferably an acyloxy ligand, an alkyloxy ligand, an aryloxy ligand, a heteroaryloxy ligand, or a silyloxy ligand, and even more preferably an acyloxy ligand.

Of the platinum complexes expressed by General Formula C-5, one of the more preferred forms is a platinum complex expressed by General Formula C-6 below.

[Thirty-Sixth Chemical Formula]

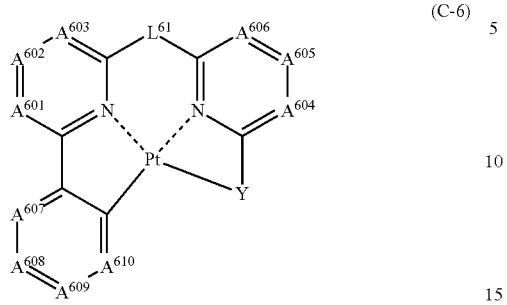

(C-6)

In General Formula C-6, $A^{601}$ to $A^{610}$ represent each independently C—R or a nitrogen atom. R represents a hydrogen atom or a substituent. $L^{61}$ represents a single bond or a divalent linking group. Y is an anionic acyclic ligand bound to platinum.

General Formula C-6 will now be described.

$L^{61}$ is defined the same as $L^{51}$ in General Formula C-5 above, and the preferred ranges are also the same. $A^{601}$ to $A^{610}$ are defined the same as $A^{301}$ to $A^{310}$ in General Formula C-3, and the preferred ranges are also the same. Y is defined the same as that in General Formula C-5, and the preferred ranges are also the same.

Concrete examples of the platinum complex expressed by General Formula C-1 include the compounds described in paragraph numbers [0143] to [0152], [0157], [0158], and [0162] to [0168] in Japanese Laid-Open Patent Application 2005-310733, the compounds described in paragraph numbers [0065] to [0083] in Japanese Laid-Open Patent Application 2006-256999, the compounds described in paragraph numbers [0065] to [0090] in Japanese Laid-Open Patent Application 2006-93542, the compounds described in paragraph numbers [0063] to [0071] in Japanese Laid-Open Patent Application 2007-73891, the compounds described in paragraph numbers [0079] to [0083] in Japanese Laid-Open Patent Application 2007-324309, the compounds described in paragraph numbers [0065] to [0090] in Japanese Laid-Open Patent Application 2006-93542; the compounds described in paragraph numbers [0055] to [0071] in Japanese Laid-Open Patent Application 2007-96255, and [the compounds described in] [0043] to [0046] in Japanese Laid-Open Patent Application 2006-313796. More concretely, examples include the platinum complexes listed below, but the present invention is not limited to or by these.

[Thirty-Seventh Chemical Formula]

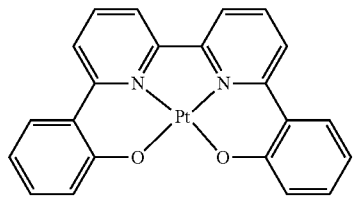

Pt-1

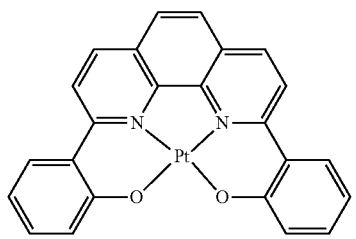

Pt-2

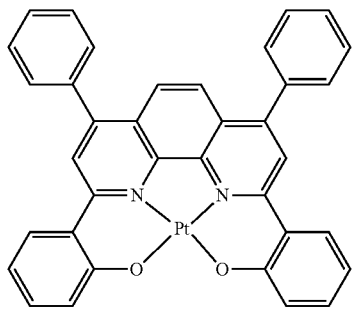

Pt-3

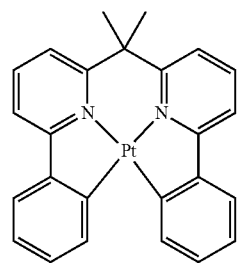

Pt-4

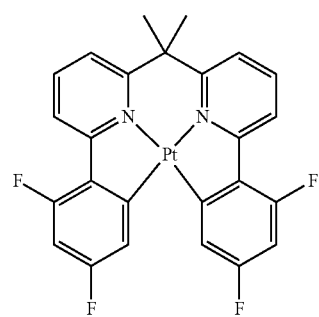

Pt-5

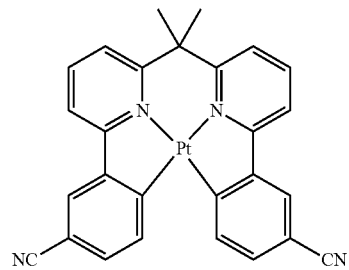

Pt-6

Pt-7
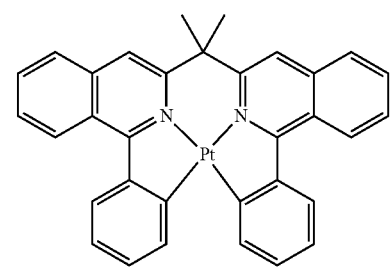
Pt-8
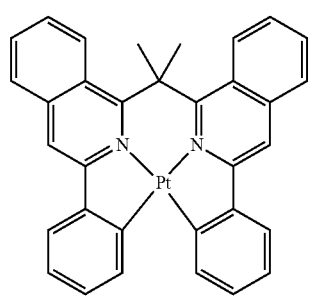
Pt-9
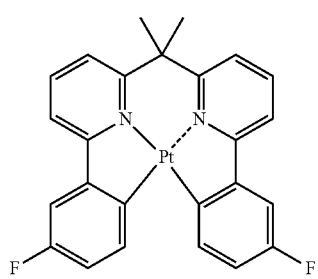
Pt-10
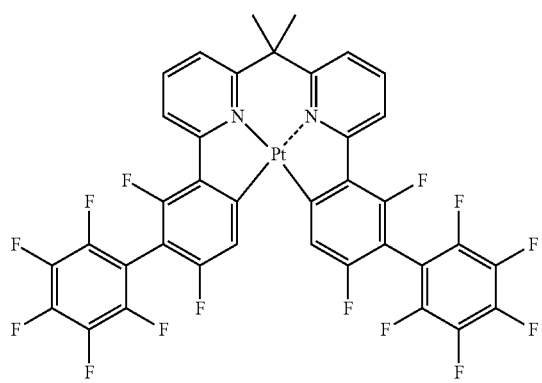
Pt-11
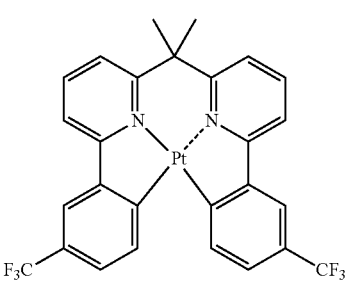
Pt-12
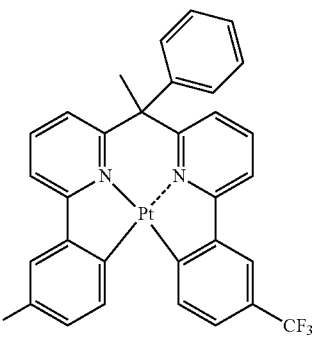
Pt-13
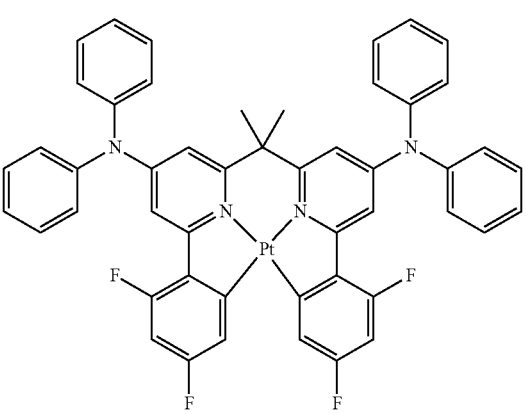
Pt-14
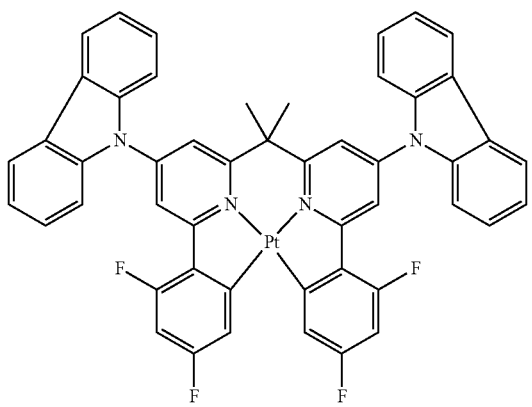
Pt-15
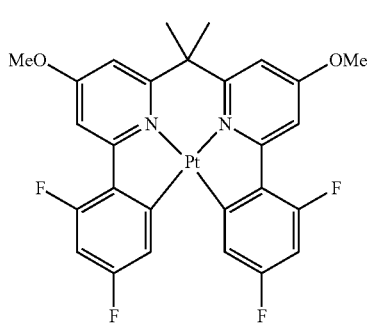

Pt-16
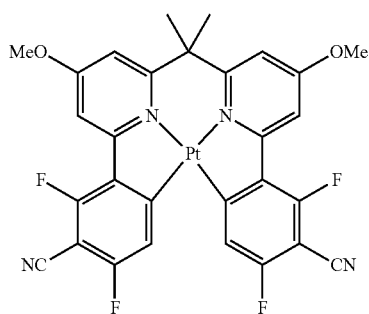
Pt-17
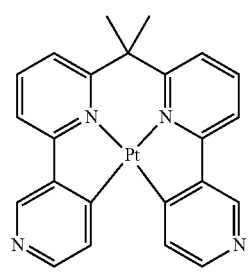
Pt-18
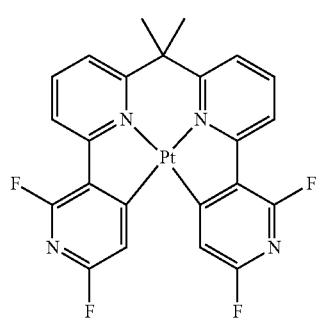
Pt-19
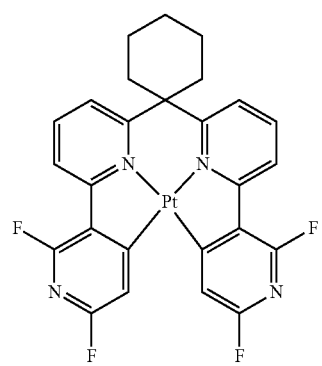
Pt-20
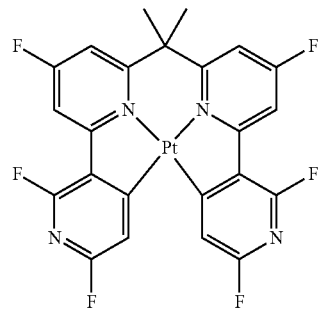
Pt-21
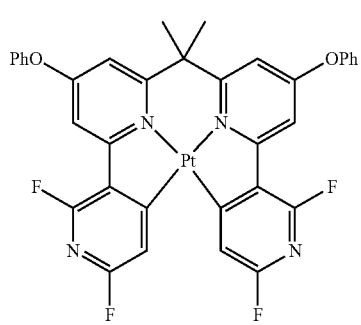
[Thirty-Eighth Chemical Formula]
Pt-22
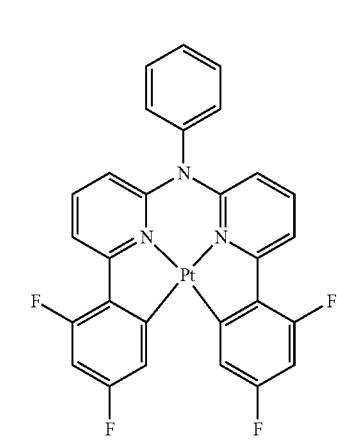
Pt-23
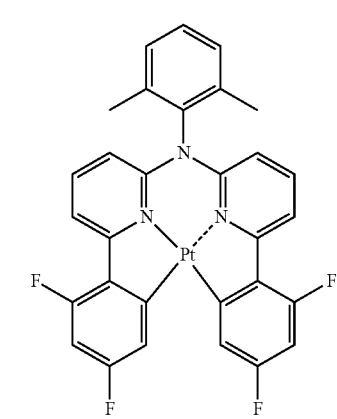
Pt-24
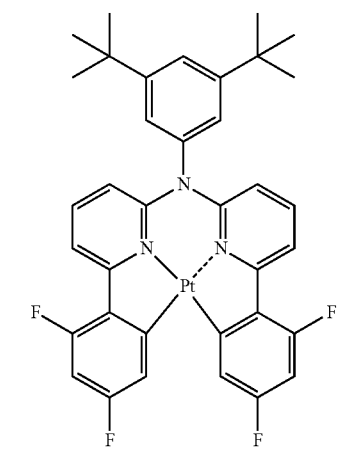

-continued
Pt-25
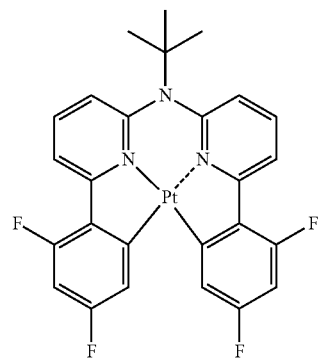
Pt-26
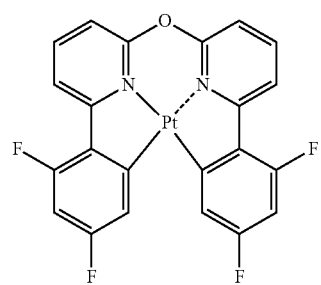
Pt-27
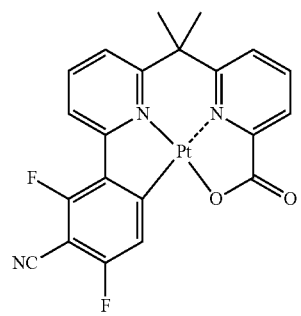
Pt-28
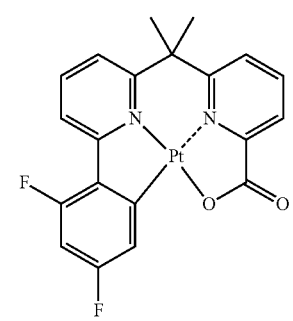
Pt-29
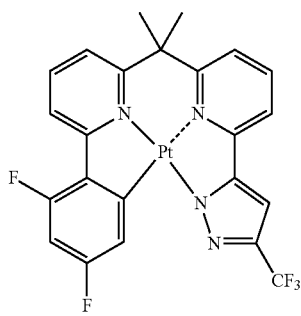
-continued
Pt-30
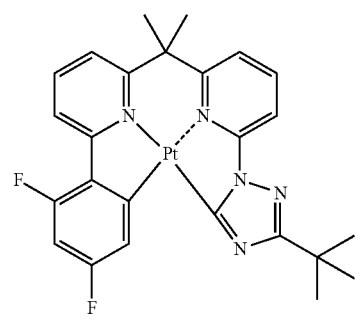
Pt-31
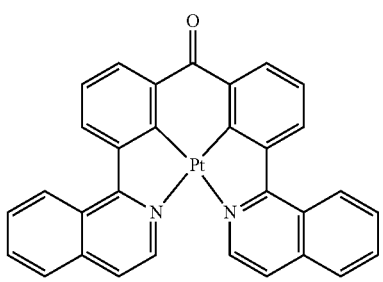
Pt-32
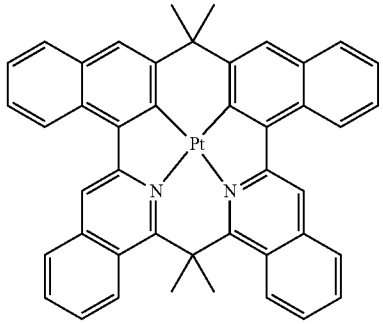
Pt-33
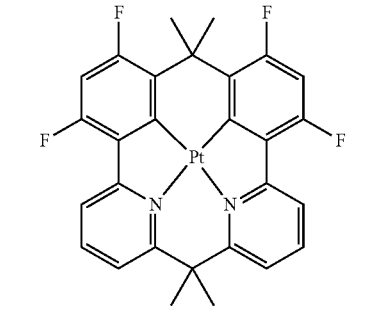
Pt-34
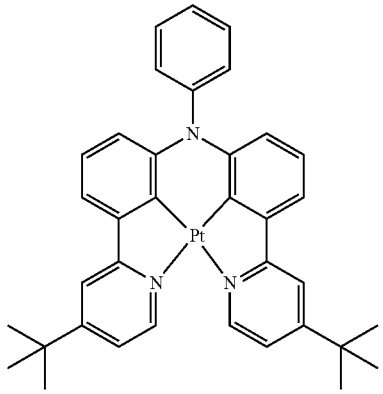

Pt-35
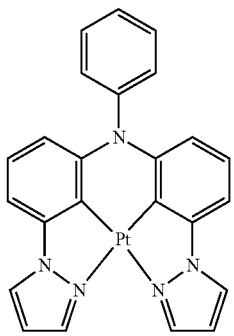
Pt-36
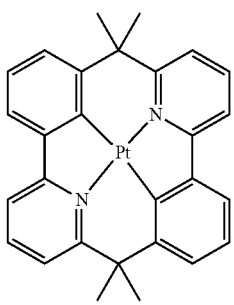
Pt-37
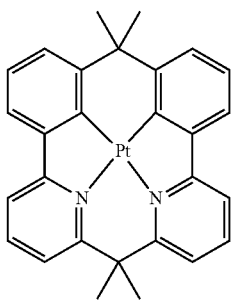
Pt-38
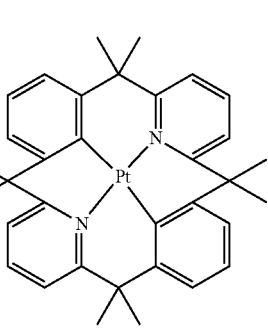
Pt-39
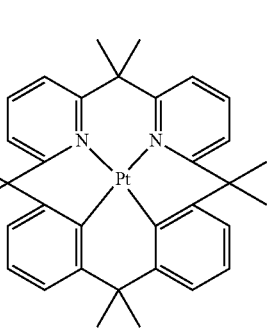
Pt-40
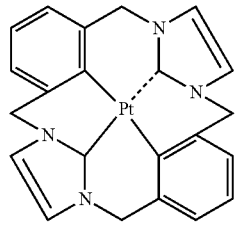
Pt-41
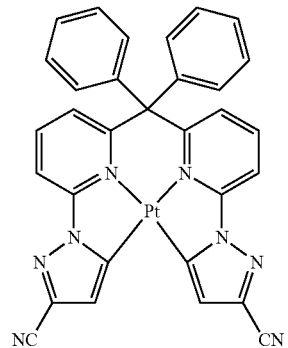
Pt-42
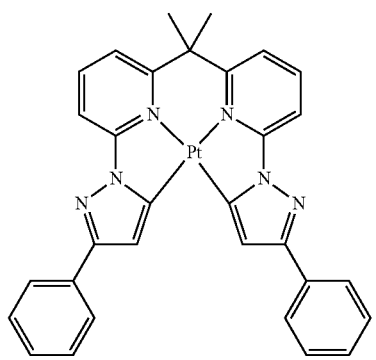
Pt-43
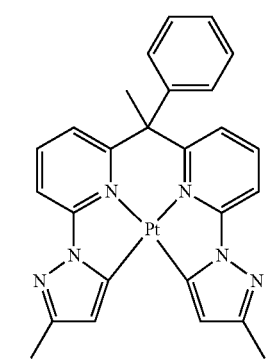
Pt-44
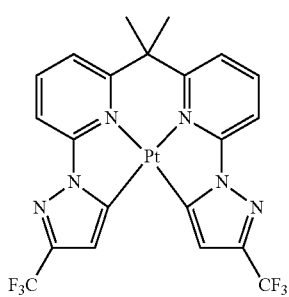

Pt-45
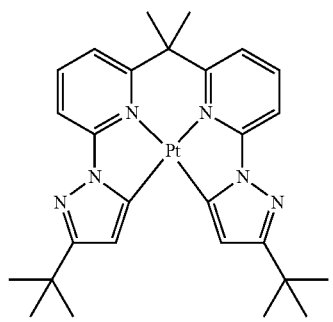
[Thirty-Ninth Chemical Formula]
Pt-46
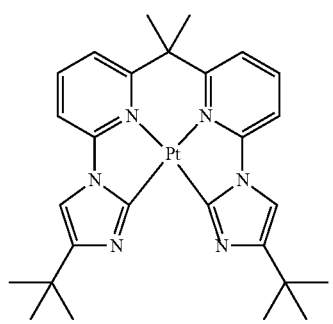
Pt-47
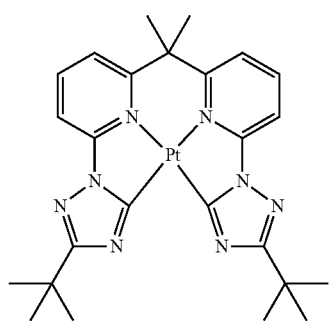
Pt-48
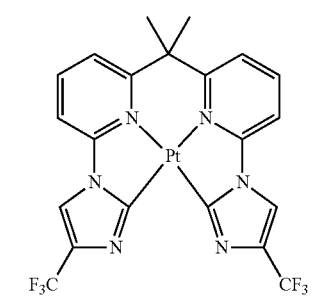
Pt-49
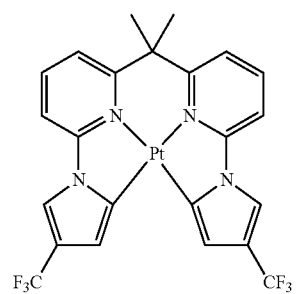
Pt-50
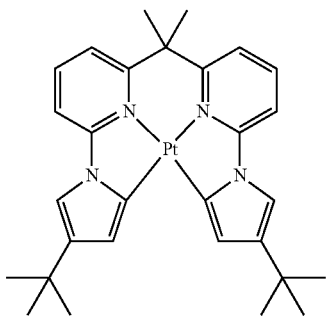
Pt-51
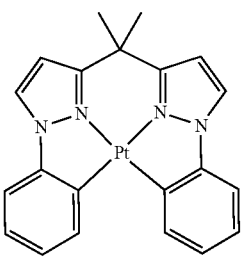
Pt-52
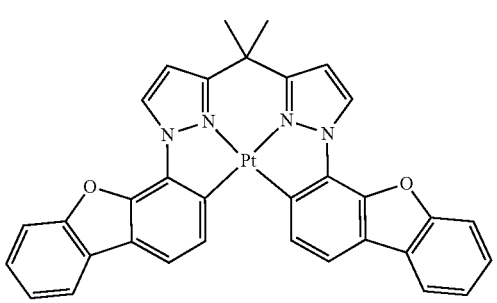
Pt-53
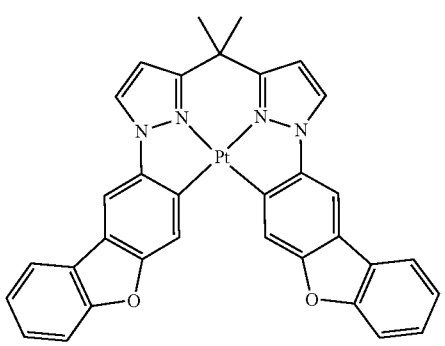
Pt-54
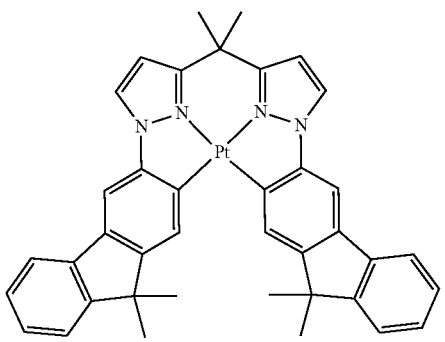

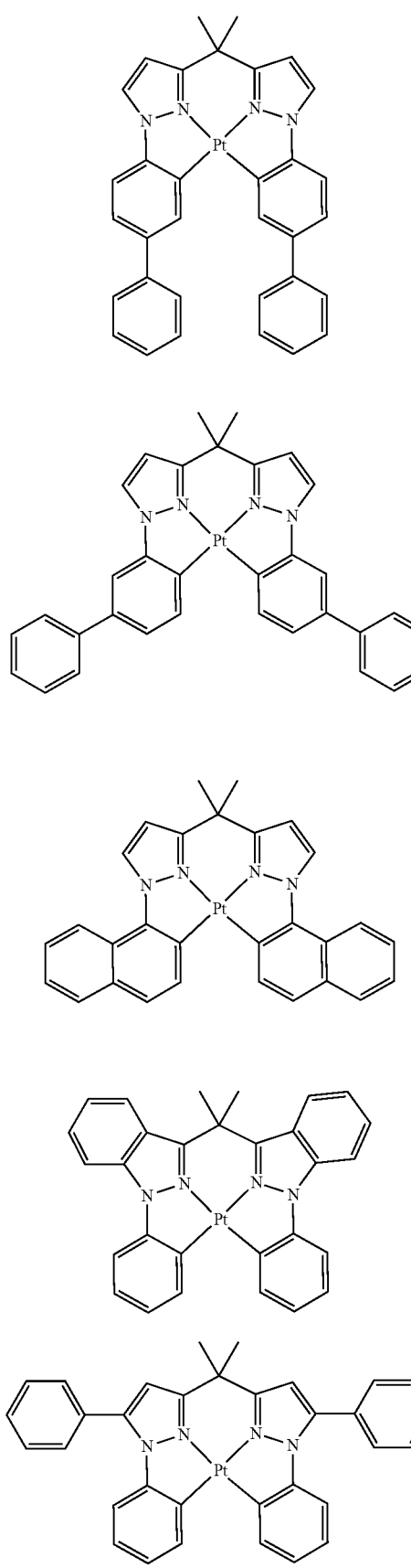
Pt-55
Pt-56
Pt-57
Pt-58
Pt-59
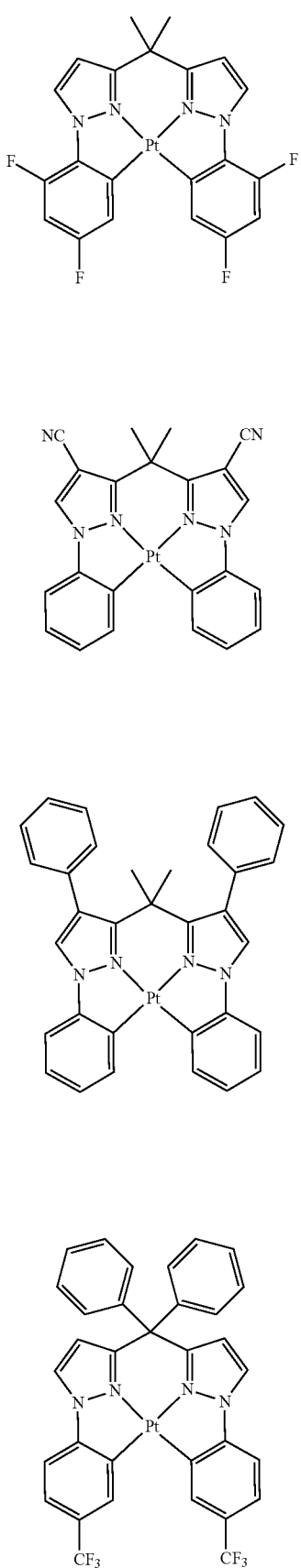
Pt-60
Pt-61
Pt-62
Pt-63

Pt-64
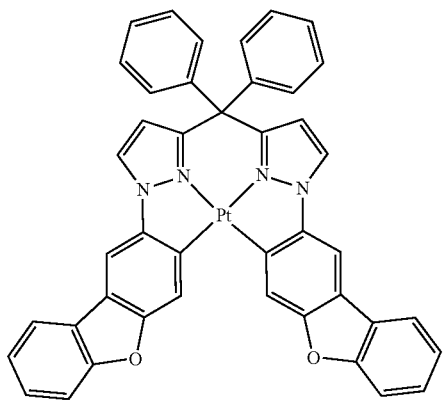

Pt-65
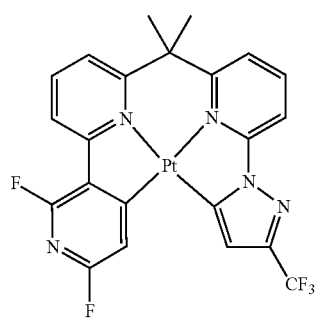

Pt-66
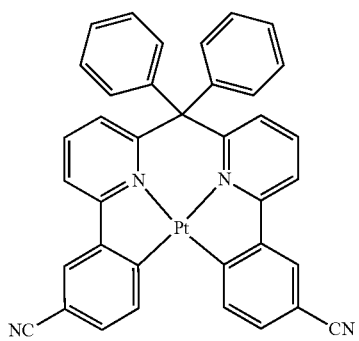

Pt-67
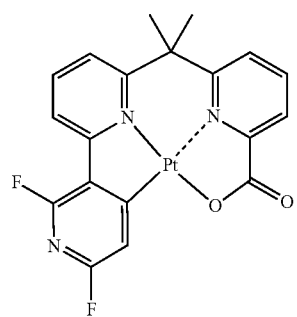

The platinum complex compound expressed by General Formula C-1 can be synthesized by various methods, such as the method described on page 789, line 53 of the left-hand column to line 7 of the right-hand column, the method described on page 790, lines 18 to 38 of the left-hand column, or the method described on page 790, lines 19 to 30 of the right-hand column, *Journal of Organic Chemistry* 53, 786, (1988), G. R. Newkome et al., or by a combination of these [methods], as well as by the method described on page 2752, lines 26 to 35 in *Chemische Berichte* 113, 2749 (1980), H. Lexy et al.

For example, [the platinum complex compound] can be obtained by treating a ligand or a dissociate thereof and a metal compound in the presence or absence of a solvent (such as a halogen-based solvent, an alcohol-based solvent, an ether-based solvent, an ester-based solvent, a ketone-based solvent, a nitrile-based solvent, an amide-based solvent, a sulfone-based solvent, a sulfoxide-based solvent, or water) and in the presence or absence of a base (various inorganic or organic bases, such as sodium methoxide, t-butoxy potassium, triethylamine and potassium carbonate) at room temperature or below or wider heating (in addition to normal heating, a method involving heating by microwaves is also effective).

The amount in which the compound expressed by General Formula C-1 is contained in the light-emitting layer of the present invention is preferably 1 to 30 wt %, more preferably 3 to 25 wt %, and even more preferably 5 to 20 wt % in the light-emitting layer.

(Host Material)

The host material is a compound that mainly handles the injection and transport of charges in the light-emitting layer, and is also a compound that substantially does not emit light itself [The phrase "substantially does not emit light" here means that the amount of light emitted from this compound that substantially does not emit light is preferably no more than 5% of the total amount of light emitted by the entire element, more preferably no more than 3%, and even more preferably no more than 1%.

The compound expressed by any of General Formulas 1 to 3 of the present invention can be used as the host material.

The following compounds are examples of other host materials that can be used in the present invention:

These examples include pyrrole, indole, carbazole, azaindole, azacarbazole, triazole, oxazole, oxadiazole, pyrazole, imidazole, thiophene, polyarylalkane, pyrazoline, pyrazolone, phenylenediamine, arylamine, amino-substituted chalcone, styrylanthracene, fluorenone hydrazone, stilbene, silazane, aromatic tertiary amine compounds, styrylamine compounds, porphyrin compounds, polysilane compounds, poly(N-vinylcarbazole), aniline copolymers, conductive macromolecular oligomers such as thiophene oligomers and polythiophene, organosilanes, carbon films, pyridine, pyrimidine, triazine, imidazole, pyrazole, triazole, oxazole, oxadiazole, fluorenone, anthraquinodimethane, anthrone, diphenylquinone, thiopyran dioxide, carbodiimide fluorenylidenemethane, distyryl pyrazine, fluorine-substituted aromatic compounds, heterocyclic tetracarboxylic anhydrides such as naphthalene perylene, phthalocyanine, and a variety of metal complexes represented by metal complexes of a 8-quinolinol derivative, metal phthalocyanine, and metal complexes having benzoxazole or benzothiazole as a ligand, and derivatives of these (which may have a substituent or a condensed ring).

The host material that can be used together in the present invention may be a hole transporting, host material or an electron transporting host material, but a hole transporting host material can be used [sic].

With the present invention, when a material other than that of the present invention is used for the aforementioned light-emitting layer, the aforementioned host material is preferably a compound expressed by General Formula H-1 below. In this case, the compound of the present invention is preferably used in a hole blocking layer.

With the present invention, when the light-emitting layer contains a compound expressed by General Formula H-1, the compound expressed by General Formula H-1 is preferably contained in the light-emitting layer in an amount of 30 to 100 wt %, [more] preferably 40 to 100 wt %, and particularly preferably 50 to 100 wt %. Furthermore, if the compound expressed by General Formula H-1 is used for a plurality of organic layers, it is preferably contained in the aforementioned range in each of these layers.

Just one type of the compound expressed by General Formula H-1 may be contained in any of the organic layers, or a plurality of compounds expressed by General Formula H-1 may be combined and contained in any proportion.

(Compound Expressed by General Formula H-1)

[Fortieth Chemical Formula]

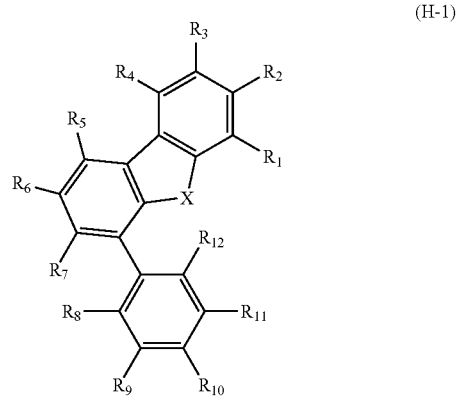

(H-1)

(In the formula, $R_1$ to $R_{12}$, represent each independently a hydrogen atom or a substituent. There are no particular restrictions on the substituent, but [those in] Substituent Group A are examples [thereof]. However, the compounds expressed by General Formula 1 are excluded. X represents a sulfur atom or an oxygen atom.)

Concrete examples of organic EL element materials comprising the compound expressed by General Formula H-1 of the present invention are given below, but these example compounds are not intended to be exhaustive.

[Forty-First Chemical Formula]

compound I-1

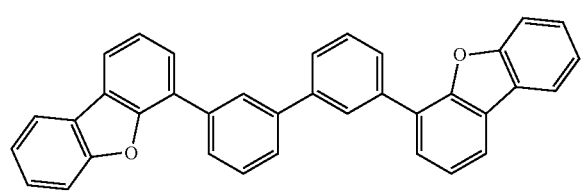

compound I-2

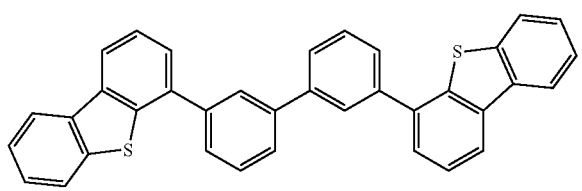

compound I-3

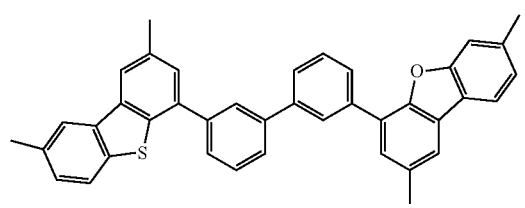

compound I-4

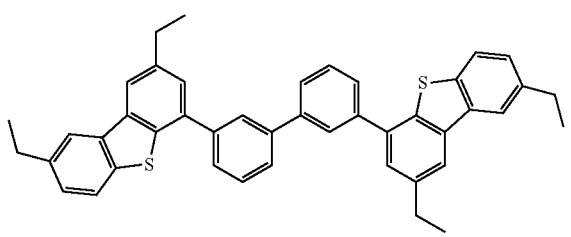

compound I-5

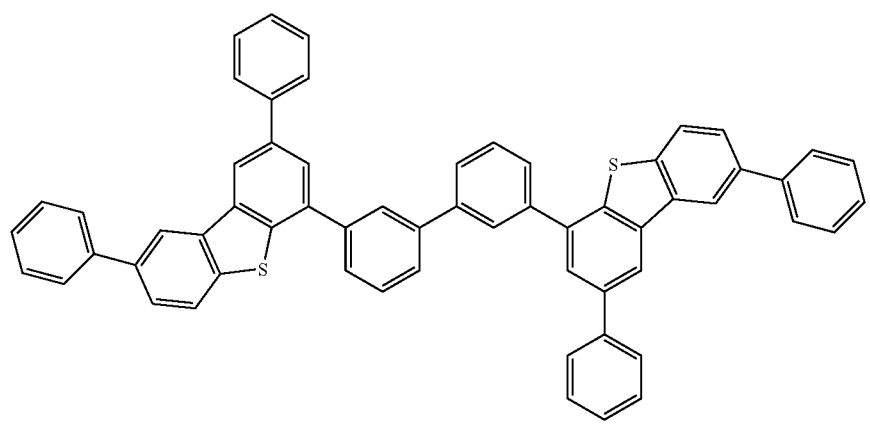

-continued compound I-6

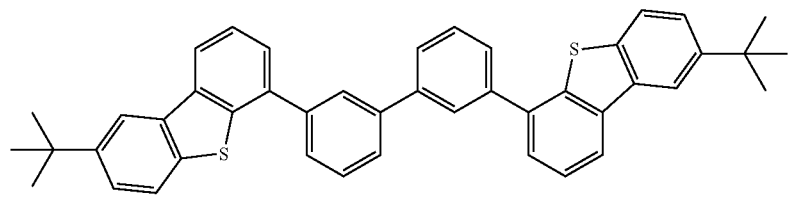

compound I-7

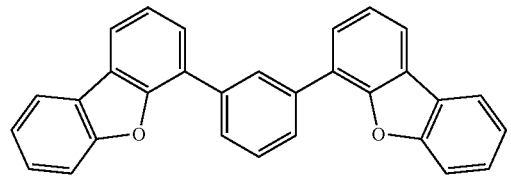

compound I-8

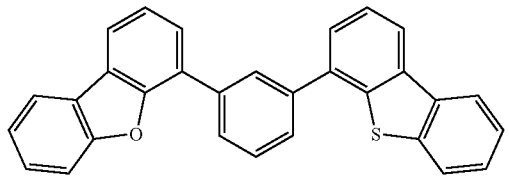

compound I-9

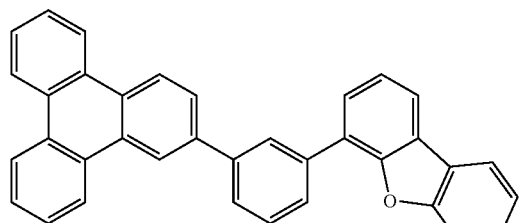

compound I-10

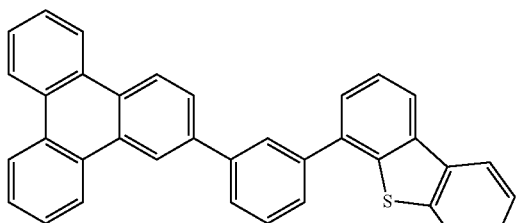

compound I-11

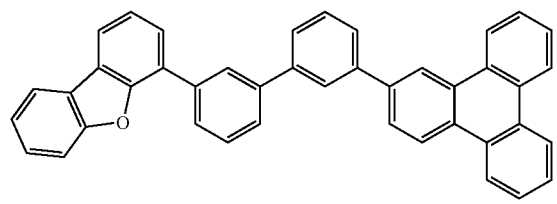

compound I-12

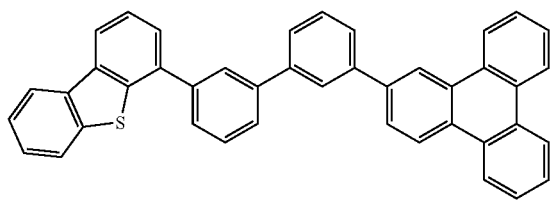

In the light-emitting layer, from the standpoints of color purity, luminous efficiency, and drive durability, it is preferable for the lowest excited triplet energy ($T_1$ energy) of the aforementioned host material to be higher than the $T_1$ energy of the aforementioned phosphorescent material. The $T_1$ of the host material is preferably higher than the $T_1$ of the phosphorescent material by 0.1 eV or more, more preferably higher by 0.2 eV or more, and even more preferably higher by 0.3 eV or more.

If the $T_1$ of the host material is lower than the $T_1$ of the phosphorescent material, emission of light is quenched, so the host material needs to have a higher $T_1$ than the phosphorescent material. Moreover, even when the $T_1$ of the host material is higher than that of the phosphorescent material, if the difference in the $T_1$ [values] between the two is small, reverse energy movement from the phosphorescent material to the host material will occur in places, and this can lead to lower efficiency or a decrease in durability. Accordingly, the host material needs to have a sufficiently high $T_1$ as well as good chemical stability and carrier injection and transport properties.

In addition, there are no particular restrictions on the amount in which the host compound is contained in the present invention, but from the standpoints of luminous efficiency and drive voltage, it is preferably at least 15 wt % and no more than 95 wt % with respect to the weight of all the compounds forming the light-emitting layer. If the light-emitting layer includes a plurality of kinds of host compound including a compound expressed by any of General Formulas 1 to 3, then the compound expressed by any of General Formulas 1 to 3 is preferably contained in the total host compound in an amount of at least 50 wt % and no more than 99 wt %.

(Compound Expressed by General Formula M-1)

In the organic electroluminescent element of the present invention, it is preferable that the aforementioned pair of electrodes include an anode and that at least one organic layer be included between the aforementioned light-emitting layer and this anode, and it is [also] preferable that at least one type of compound expressed by General Formula M-1 below be contained in this organic layer.

More preferably, the compound expressed by General Formula M-1 is contained in an organic layer that is between the light-emitting layer and the anode and adjacent to the light-emitting layer, but its application is in no way limited, and [this compound] may be further contained in any of the organic layers. The layer into which the compound expressed by General Formula M-1 according to the present invention is introduced can be any of the light-emitting layer, the hole injection layer, the hole transport layer, the electron transport layer, the electron injection layer, the exciton blocking layer, and the charge blocking layer, or [the compound] can be contained in a plurality [of these layers].

The organic layer that contains the compound expressed by General Formula M-1 and that is between the light-emitting layer and the anode and adjacent to the light-emitting layer is more preferably a hole transport layer.

[Forty-Second Chemical Formula]

In General Formula M-1, $Ar_1$ and $Ar_2$ represent each independently an alkyl, an aryl, a heteroaryl, an arylamino, an alkylamino, a morpholino, a thiomorpholino, or a five- or six-member heterocycloalkyl or cycloaklyl containing one or more hetero atoms selected from among N, O, and S, and may further have a substituent Z. Furthermore, $Ar_1$ and $Ar_2$ may be bound together by a single bond, an alkylene, or an alkenylene (regardless of whether or not there is a condensed ring) to form a condensed five- to nine-member ring.

$Ar_3$ represents a p-valent alkyl, aryl, heteroaryl, or arylamino, and may further have a substituent Z.

The Z [groups] represent each independently a halogen atom, —R", —OR", —N(R")$_2$, —SR", —C(O)R", —C(O)OR", —C(O)N(R")$_2$, —CN, —NO$_2$, —SO$_2$, —SOR", —SO$_2$R", or —SO$_3$R". The R" [groups] represent each independently a hydrogen atom, an alkyl group, a perhaloalkyl group, an alkenyl group, an alkynyl group, an aryl group, or a heteroaryl group.

p is an integer from 1 to 4, and when p is greater than or equal to 2, $Ar_1$ and $Ar_2$ may be the same as or different from each other.

When the compound expressed by General Formula M-1 is used in as hole transport layer, the compound expressed by General Formula M-1 is preferably contained in an amount of 50 to 100 wt %, more preferably 80 to 100 wt %, and particularly preferably 95 to 100 wt %.

Moreover, when the compound expressed by General Formula M-1 is used in a plurality of organic layers, it is preferably contained within the aforementioned ranges in each of the layers.

Just one kind of the compound expressed by General Formula M-1 may be contained in any of the organic layers, or a plurality of compounds expressed by General Formula M-1 may be combined and contained in the desired proportions.

The thickness of the hole transport layer that includes the compound expressed by General Formula M-1 is preferably 1 to 500 nm, more preferably 3 to 200 nm, and even more preferably 5 to 100 tun. In addition, this hole transport layer is preferably provided so as to contact the light-emitting layer.

This hole transport layer may have a single-layer structure composed of one or more types of the aforementioned material, or a multilayer structure composed of a plurality of layers having the same composition or different compositions.

The lowest triplet excitation ($T_1$)) energy of the compound expressed by General Formula M-1 in a film state is preferably at least 2.52 eV (58 kcal/mol) and no more than 3.47 eV (80 kcal/mol), more preferably at least 2.60 eV (60 kcal/mol) and no more than 3.25 eV (75 kcal/mol), and even more preferably at least 2.69 eV (62 kcal/mol) and no more than 3.04 eV (70 kcal/mol).

The hydrogen atoms constituting General Formula M-1 also include isotopes of hydrogen (such as deuterium atoms). In this case, all the hydrogen atoms in the compound may be replaced by hydrogen isotopes, or may be a mixture a part of which is a compound containing hydrogen isotopes.

The compound expressed by General Formula M-1 can be synthesized by combining a variety of publicly known synthesis methods. The most typical example, for a carbazole compound, is to conduct Aza-Cope rearrangement of a condensate of arythydrazine and a cyclohexane derivative, and then perform synthesis by dehydrogenation aromatization (L. F. Tieze and Th. Eicher, translated by Takano and Ogasawara, Seimitsu Yuki Gosei, p. 339 (Nankodo)). [Other] examples are the methods described in Tetrahedron Letters, Vol. 39, p. 617, (1998), ibid., Vol. 39, p. 2367 (1998), ibid., Vol. 40, p. 6393 (1999), etc., which relate to a coupling reaction of the resulting carbazole compound and a halogenated aryl compound using a palladium catalyst. There are no particular restrictions on the reaction temperature or reaction time, and the conditions given in the above publications can be applied.

The compound expressed by General Formula M-1 of the present invention preferably forms a thin film by a vacuum vapor deposition process, but a wet process such as solution coating can also be used favorably. From the standpoints of solubility and suitability to vapor deposition, the molecular weight of the compound is preferably no more than 2000, more preferably no more than 1200, and particularly preferably no more than 800. Furthermore, from the standpoint of suitability to vapor deposition, if the molecular weight is too low, the vapor pressure will drop, and there will be no change from the vapor phase to the solid phase, making it difficult to form an organic layer, so at least 250 is preferable, and at least 300 is particularly preferable.

Concrete examples of the compound expressed by General Formula M-1 are given below, but the present invention is not limited to or by these.

[Forty-Third Chemical Formula]

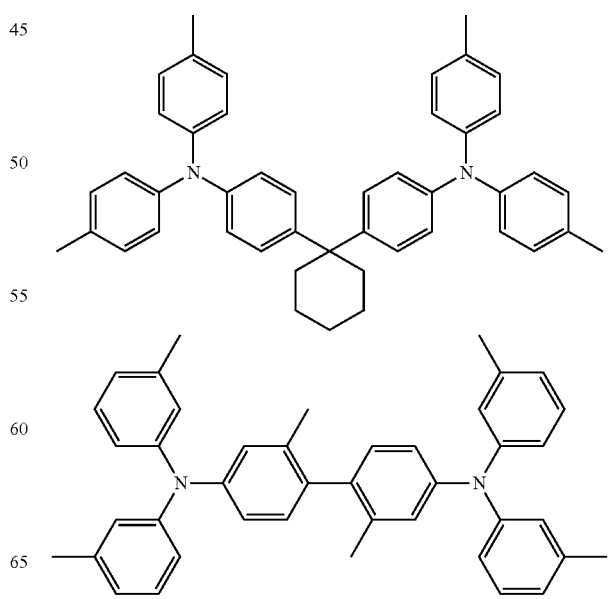

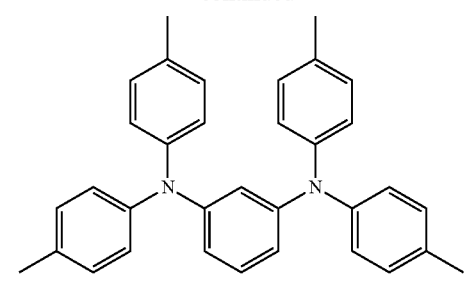
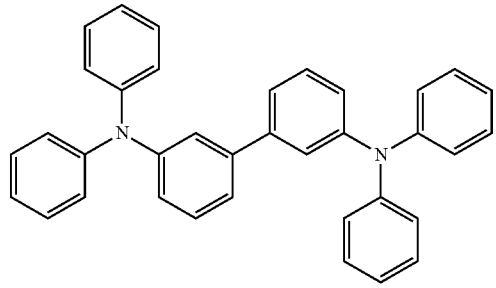
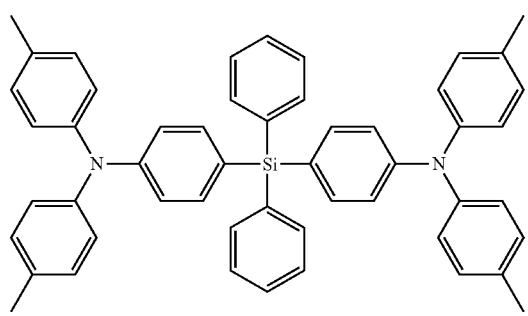
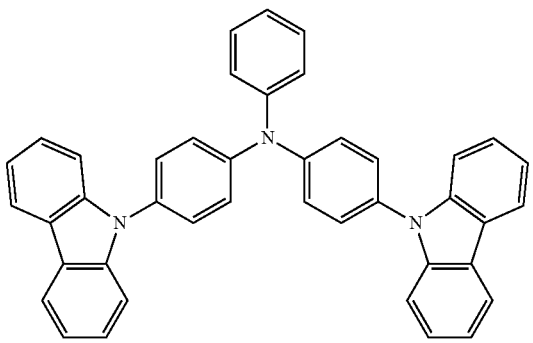
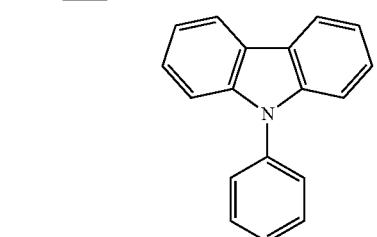
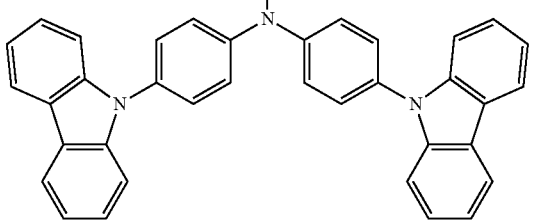
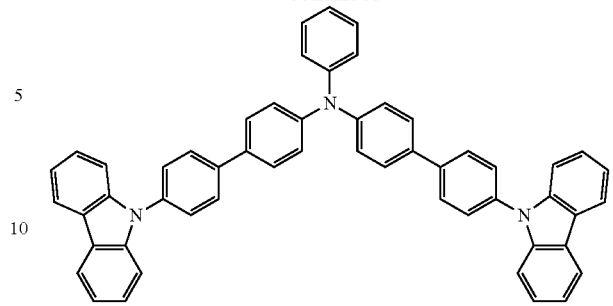
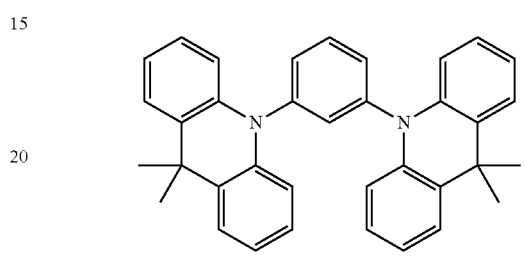
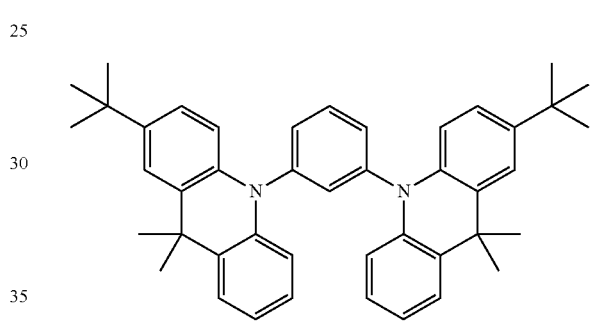
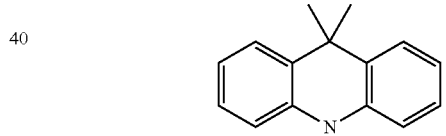
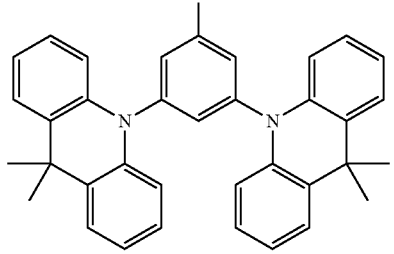
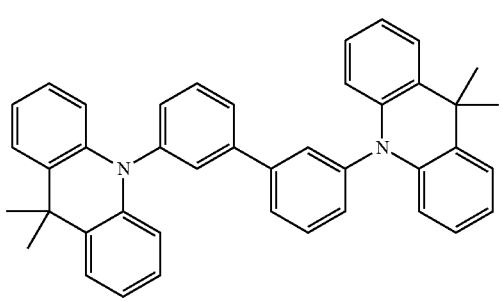

83
-continued
[Forty-Fourth Chemical Formula]
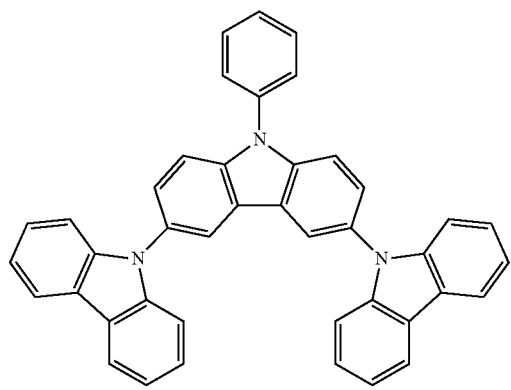
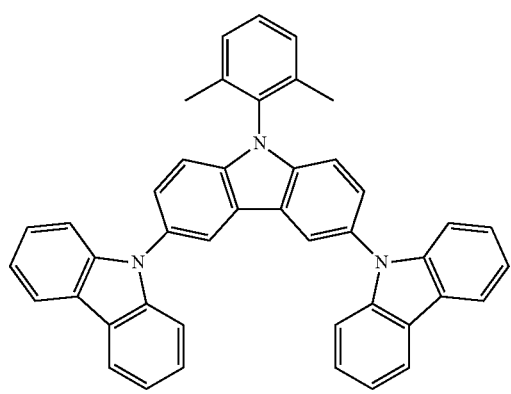
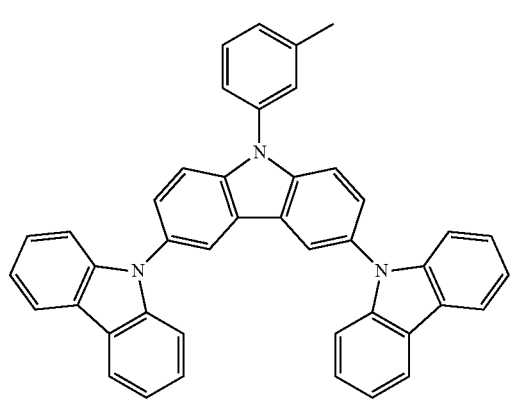
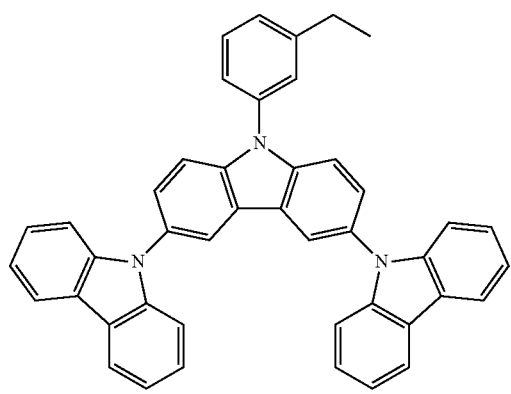
84
-continued
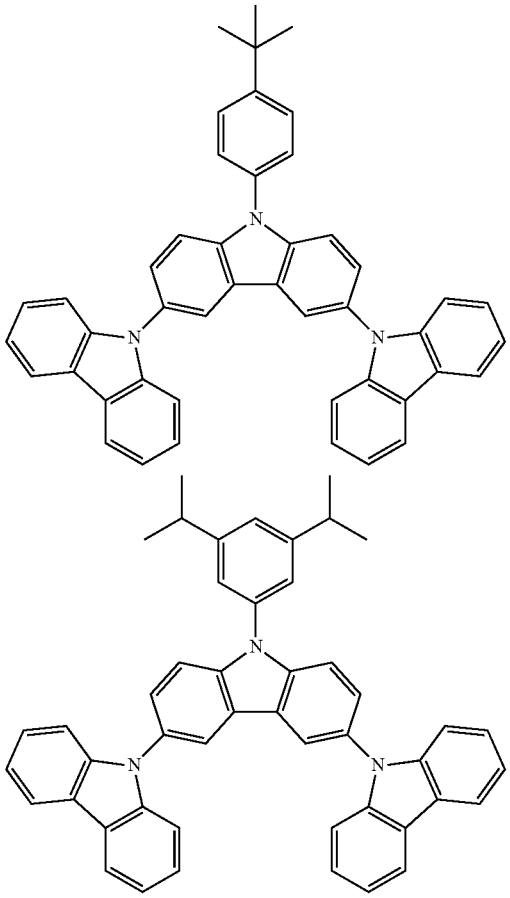
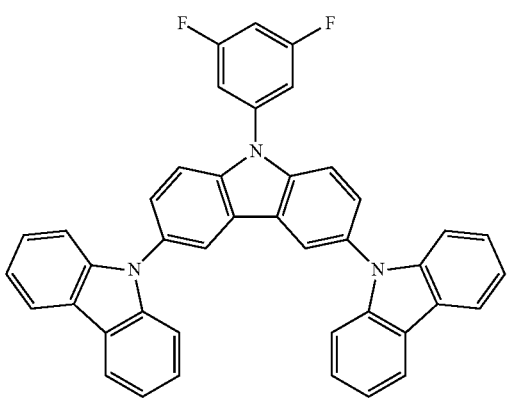
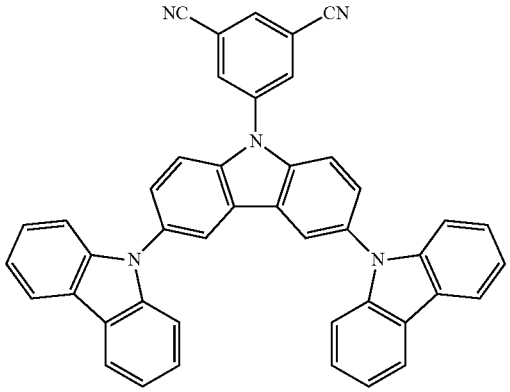

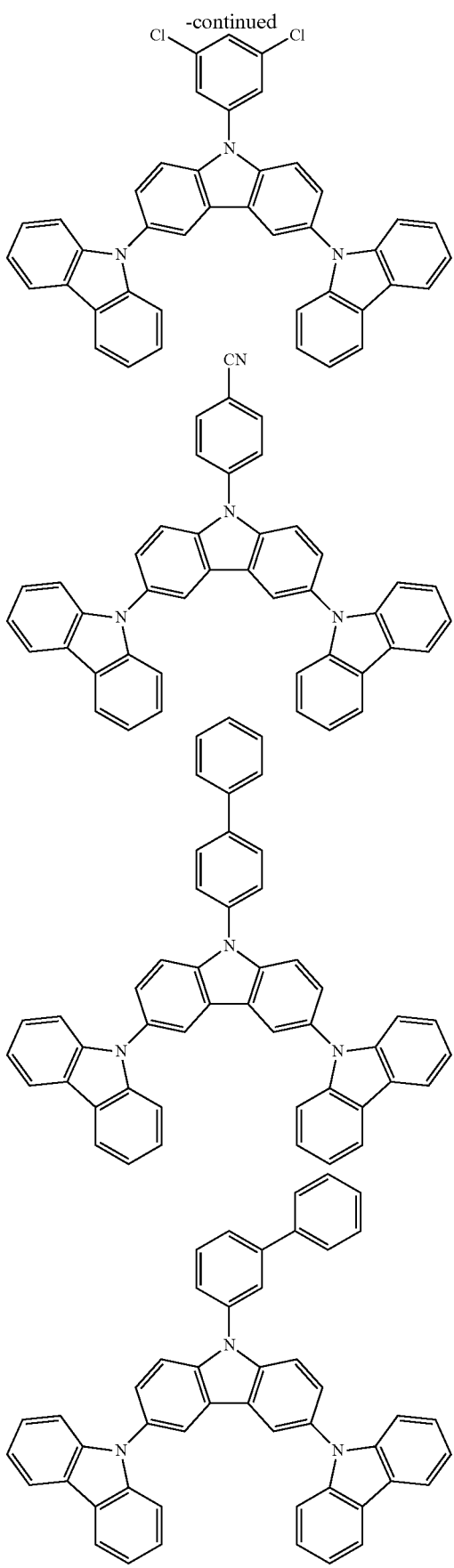
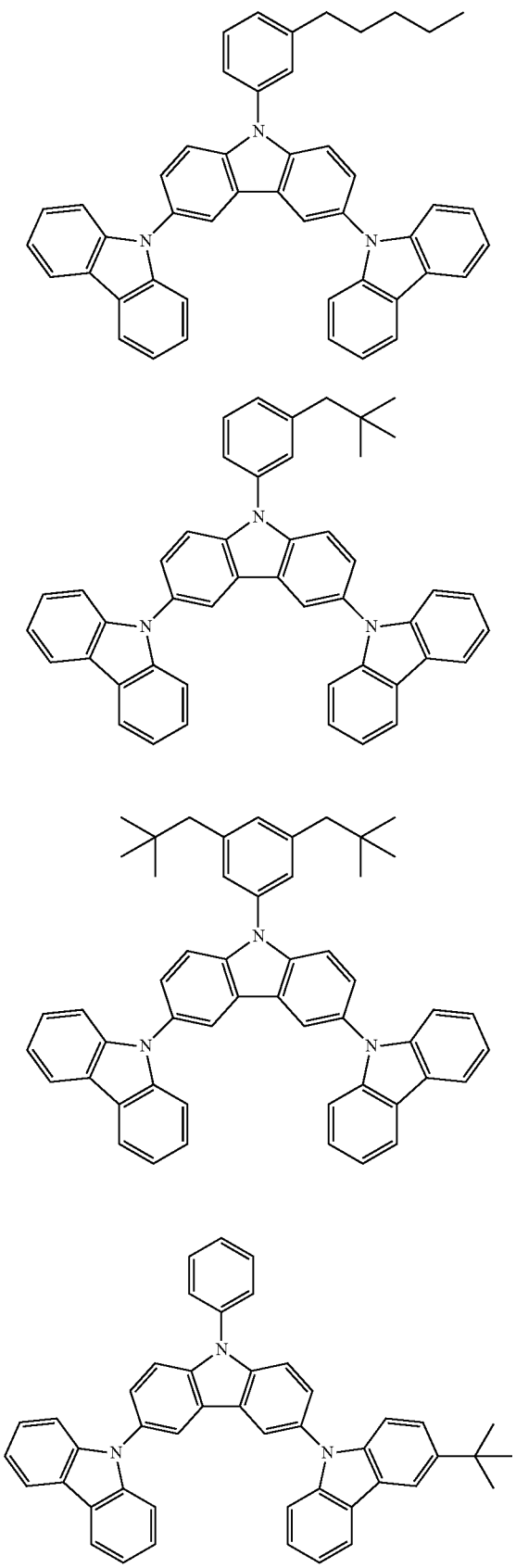
[Forty-Fifth Chemical Formula]

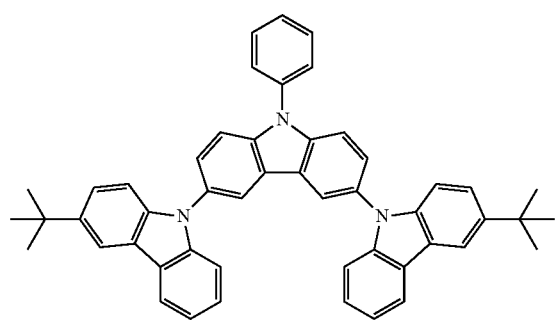
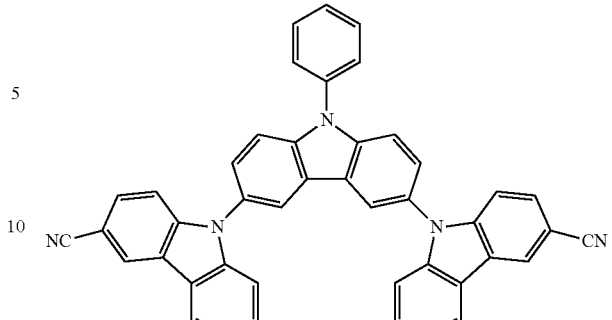
[Forty-Sixth Chemical Formula]

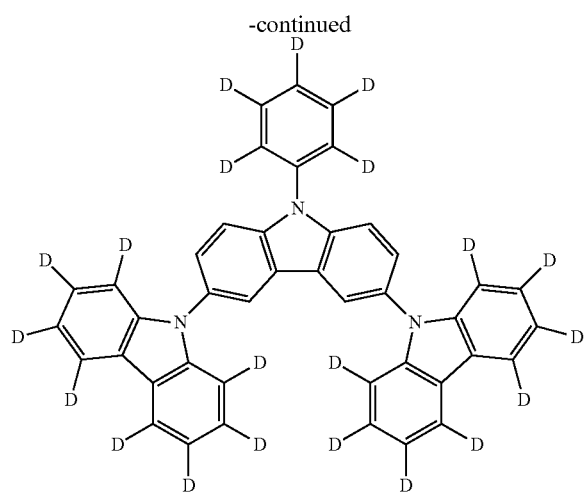
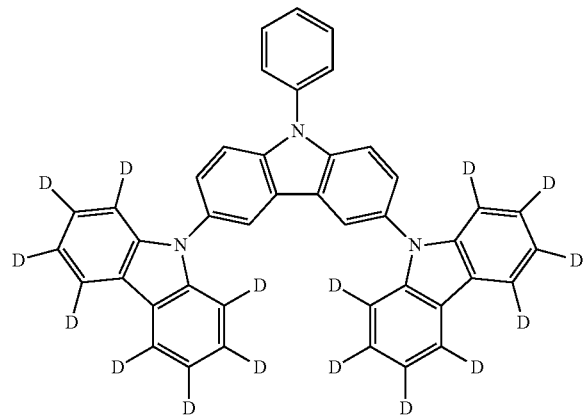
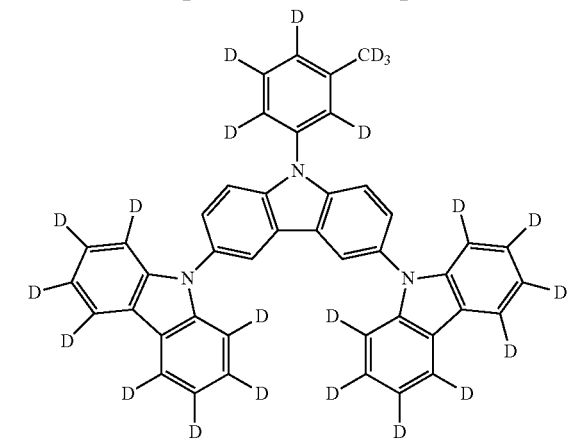
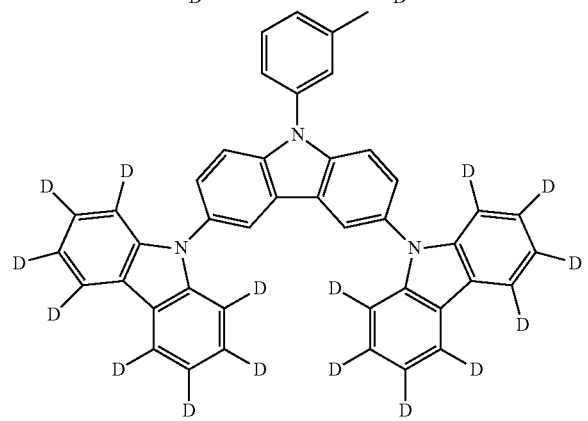

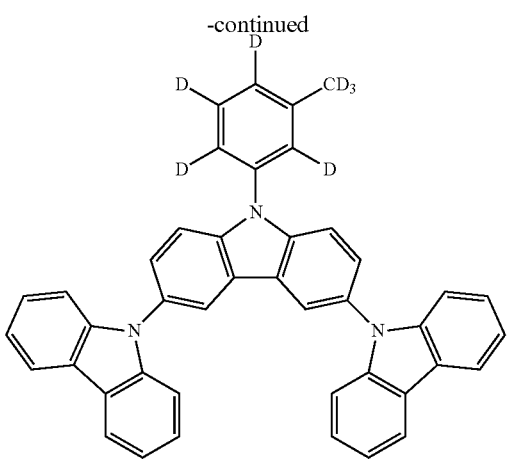
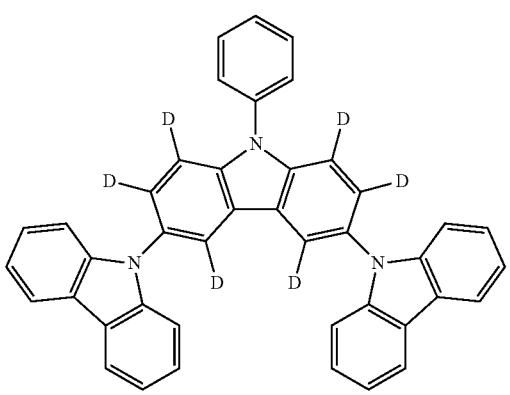

[Forty-Seventh Chemical Formula]

(Aromatic Hydrocarbon Compound)

In the organic electroluminescent element of the present invention, preferably, the aforementioned pair of electrodes include a cathode, and at least one organic layer is included between the aforementioned light-emitting layer and this cathode, with this organic layer preferably containing an aromatic hydrocarbon compound.

The aromatic hydrocarbon compound is more preferably contained, in the organic layer that is between the light-emitting layer and the cathode and adjacent to the light-emitting layer, but its application is in no way limited, and [this compound] may be further contained in any of the organic layers. The layer into which the aromatic hydrocarbon compound according to the present invention is introduced can be the light-emitting layer, the hole injection layer, the hole transport layer, the electron transport layer, the electron injection layer, the exciton blocking layer, or the charge blocking layer, or it can be contained in a plurality [of layers].

The organic layer that contains the aromatic hydrocarbon compound and that is between the light-emitting layer and the cathode and adjacent to the light-emitting layer is preferably the charge blocking layer or the electron transport layer and more preferably the electron transport layer.

From the standpoint of ease of synthesis, the aromatic hydrocarbon compound is preferably composed solely of carbon atoms and hydrogen atoms.

If the aromatic hydrocarbon compound is contained, in a layer other than the light-emitting layer, it is preferably contained in an amount of 70 to 100 wt % and more preferably 85 to 100' wt %. If the aromatic hydrocarbon compound is contained in the light-emitting layer, it is preferably contained in an amount of 0.1 to 99 wt %, more preferably 1 to 95 wt %, and even more preferably 10 to 95 wt %, with respect to the total weight of the light-emitting layer.

It is preferable to use a hydrocarbon compound that is composed solely of carbon atoms and hydrogen atoms, that has a molecular weight of between 400 and 1200, and that has a condensed polycyclic skeleton with a total carbon number of 13 to 22. A condensed polycyclic skeleton with a total carbon number of 13 to 22 is preferably fluorene, anthracene, phenanthrene, tetracene, chrysene, pentacene, pyrene, perylene, or triphenylene. From the standpoint of T1, fluorene, triphenylene, and phenanthrene are more preferable, and from the standpoints of compound stability and ease of charge injection and transport, triphenylene is even more preferable, with the compound expressed by General Formula Tp-1 being particularly favorable.

The hydrocarbon compound expressed by General Formula Tp-1 preferably has a molecular weight of between 400 and 1200, more preferably between 400 and 1000, and even more preferably between 400 and 800. If the molecular weight is at least 400, a good amorphous thin film can be formed, and it is preferable for the molecular weight to be no more than 1200 in terms of solubility in a solvent and proper sublimation and vapor deposition.

There are no restrictions on the application of the hydrocarbon compound expressed by General Formula Tp-1, and it may be contained not only in an organic layer that is adjacent to the light-emitting layer, but also in any of the other organic layers.

[Forty-Eighth Chemical Formula]

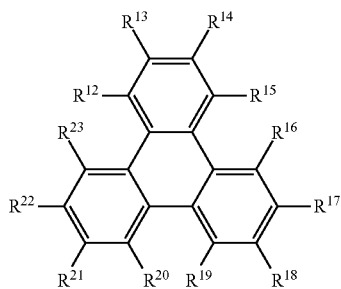

(Tp-1)

(In General Formula Tp-1. $R^{12}$ to $R^{23}$ represent each independently a hydrogen atom or an alkyl group, or a phenyl group, fluorenyl group, naphthyl group, or triphenylenyl group that may be substituted with an alkyl group, phenyl group, fluorenyl group, naphthyl group, or triphenylenyl group. However, $R^{12}$ to $R^{23}$ cannot all be hydrogen atoms.)

The alkyl group expressed by $R^{12}$ to $R^{23}$ may be substituted or unsubstituted, and examples include a methyl group, an ethyl group, an isopropyl group, an n-butyl group, a tert-butyl group, an n-octyl group, an n-decyl group, an n-hexadecyl group, a cyclopropyl group, cyclopentyl group, and a cyclohexyl group. Preferable [examples] are a methyl group, an ethyl group, an isopropyl group, a tert-butyl group, and a cyclohexyl group, with a methyl group, an ethyl group, and a tert-butyl group being even more preferable.

$R^{12}$ to $R^{23}$ are preferably a $C_1$ to $C_4$ alkyl group, and even more preferably a phenyl group, fluorenyl group, naphthyl group, or triphenylenyl group that may be substituted with a $C_1$ to $C_4$ alkyl group, phenyl group, fluorenyl group, naphthyl group, or triphenylenyl group (these may be further substituted with an alkyl group, phenyl group, fluorenyl group, naphthyl group, or triphenylenyl group).

Particularly favorable is a benzene ring that may be substituted with a phenyl group, fluorenyl group, naphthyl group, or triphenylenyl group (these may be further substituted with an alkyl group, phenyl group, fluorenyl group, naphthyl group, or triphenylenyl group).

The total number of aryl rings in General Formula Tp-1 is preferably 2 to 8 and more preferably 3 to 5. Within this range, a good amorphous thin film can be formed, and there will be good solubility in a solvent and proper sublimation and vapor deposition.

$R^{12}$ to $R^{23}$ preferably each independently have a total carbon number of 20 to 50 and more preferably a total carbon number of 20 to 36. Within this range, a good amorphous thin film can be formed, and there will be good solubility in a solvent and proper sublimation and vapor deposition.

In one aspect of the present invention, the hydrocarbon compound expressed by General Formula Tp-1 above is preferably a hydrocarbon compound expressed by General Formula (Tp-2) below.

[Forty-Ninth Chemical Formula]

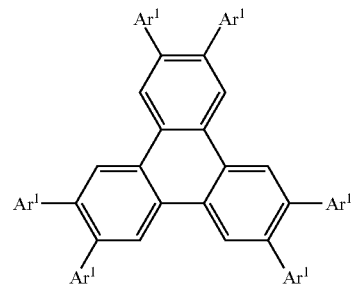

(Tp-2)

(In General Formula Tp-2, the plurality of $Ar^1$ [groups] are the same and represent a phenyl group, fluorenyl group, naphthyl group, or triphenylenyl group that may be substituted with an alkyl group, phenyl group, fluorenyl group, naphthyl group, or triphenylenyl group.)

[Examples of] the alkyl group and the phenyl group, fluorenyl group, naphthyl group, or triphenylenyl group that may be substituted with an alkyl group, phenyl group, fluorenyl group, naphthyl group, or triphenylenyl group expressed by $Ar^1$ are the same as those listed for $R^{12}$ to $R^{23}$, and preferred examples are also the same.

In another aspect of the present invention, the hydrocarbon compound expressed by General Formula Tp-1 above is preferably a hydrocarbon compound expressed by General Formula Tp-3 below.

[Fiftieth Chemical Formula]

General Formula Tp-3

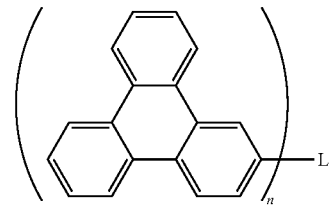

(In General Formula Tp-3, L represents an n-valent linking group composed of a phenyl group, fluorenyl group, naphthyl group, or triphenylenyl group that may be substituted with an alkyl group, phenyl group, fluorenyl group, naphthyl group, or triphenylenyl group, or a combination of these. n represents an integer from 1 to 6.)

[Examples of] the alkyl group, phenyl group, fluorenyl group, naphthyl group, or triphenylenyl group that forms the n-valent linking group expressed by L are the same as those given for $R^{12}$ to $R^{23}$.

L is preferably an n-valent linking group composed of a benzene ring or fluorene ring that may be substituted with an alkyl group or a benzene ring, or a combination of these.

Concrete, preferred examples of L are given below, but L is not limited to these. Note that a triphenylene ring is bound at the asterisk in the concrete examples.

[Fifty-First Chemical Formula]

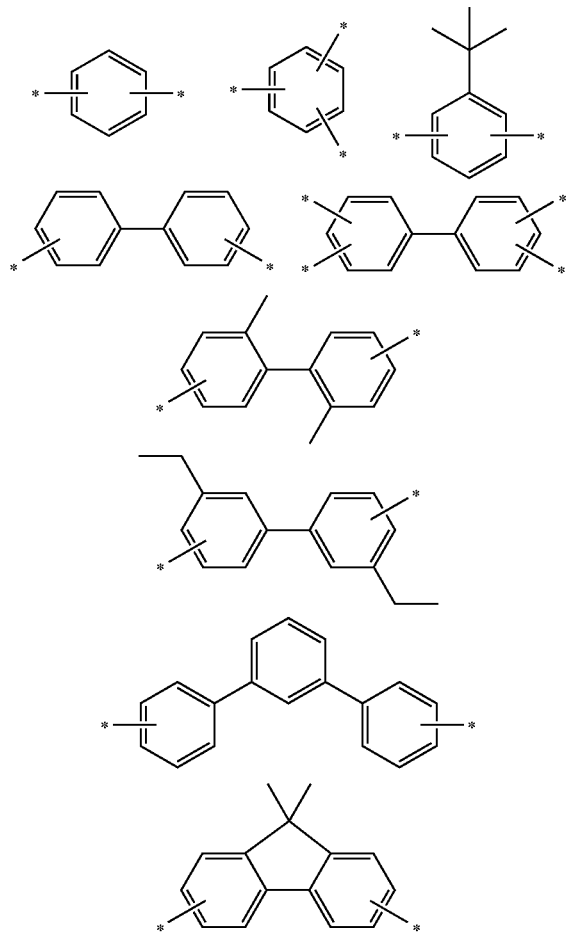

n is preferably from 1 to 5 and more preferably from 1 to 4.

In another aspect of the present invention, the hydrocarbon compound expressed by General Formula Tp-1 above is preferably a hydrocarbon compound expressed by General Formula Tp-4 below.

[Fifty-Second Chemcial Formula]

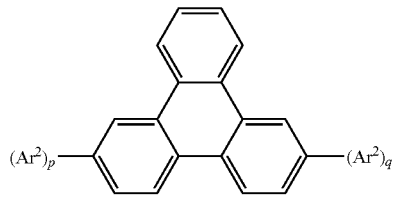

(Tp-4)

(In General Formula Tp-4, if there are a plurality of $Ar^2$ [groups], they are the same, and $Ar^2$ [groups each] represent a group substituted with an alkyl group, phenyl group, naphthyl group, or triphenylenyl group, or composed of a combination of these. p and q represent each independently 0 or 1, but p and q cannot both be it at the same time. When p and q represent 0, $Ar^2$ represents a hydrogen atom.)

$Ar^2$ is preferably a group composed of a combination of a $C_1$ to $C_4$ alkyl group, phenyl group, naphthyl group, and triphenylenyl group and more preferably a group composed of a combination of a methyl group, t-butyl group, phenyl group, and triphenylenyl group.

$Ar^2$ is particularly preferably a benzene ring that has been substituted at the meta position with a $C_1$ to $C_4$ alkyl group, phenyl group, naphthyl group, or triphenylenyl group, or a group composed of a combination of these.

When the hydrocarbon compound according to the present invention is used for the host material of the light-emitting layer of an organic electroluminescent element or a charge transport material of a layer adjacent to the light-emitting layer, if the energy gap in a thin film state (when the light-emitting material is a phosphorescent material, the lowest excitation triplet ($T_1$) energy in a thin film state) is greater than that of the light-emitting material, this is advantageous in preventing the emission of light from being quenched, and in increasing efficiency. On the other hand, from the standpoint of the chemical stability of the compound, it is preferable for the energy gap and the $T_1$ energy not to be too great. The $T_1$ energy in a thin film state of a hydrocarbon compound expressed by General Formula Tp-1 is preferably at least 52 kcal/mol and no more than 80 kcal/mol, more preferably at least 55 kcal/mol and no more than 68 kcal/mol, and even more preferably at least 58 kcal/mol and no more than 63 kcal/mol. In particular, when a phosphorescent material is used as the light-emitting material, the $T_1$ energy is preferably within the aforementioned range.

The $T_1$ energy can be found by the same method as that described for General Formula 1 above.

From the standpoint of stable operation of the organic electroluminescent element with respect to heat emission in element drive or during high-temperature drive, the glass transition temperature (TO of the hydrocarbon compound according to the present invention is preferably at least 80° C. and no more than 400° C. more preferably at least 100° C. and no more than 400° C., and even more preferably at least 120° C. and no more than 400° C.

Concrete examples of the hydrocarbon compound according to the present invention are given below, but the present invention is not limited to or by these.

[Fifty-Third Chemical Formula]
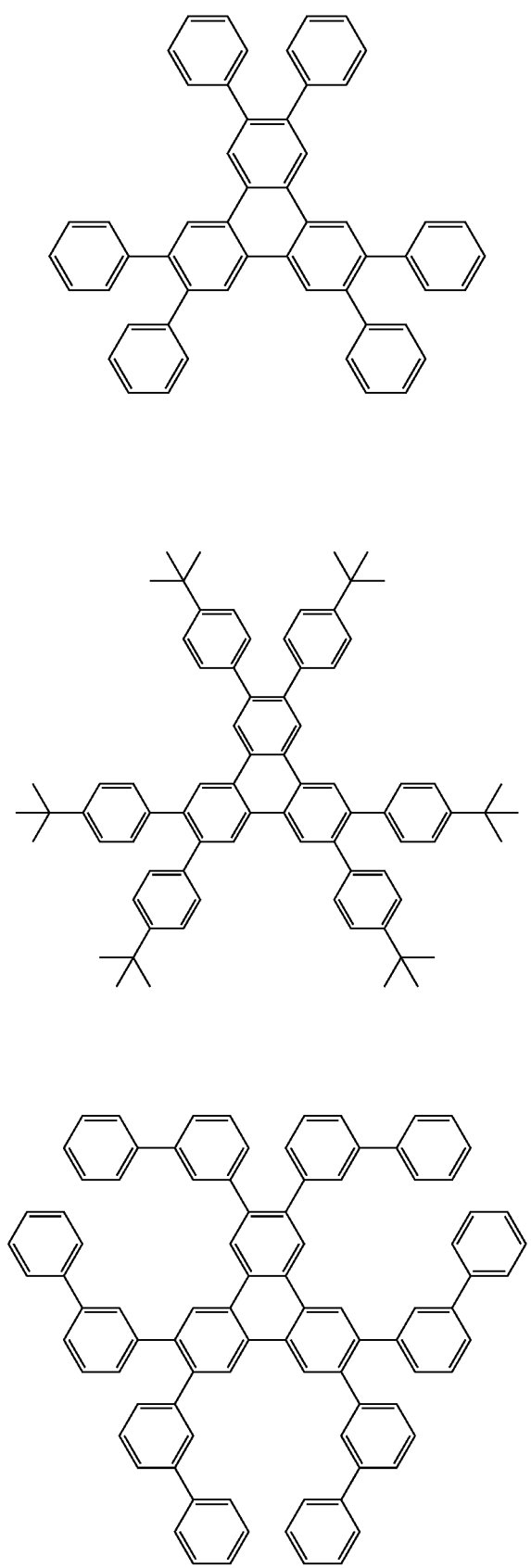
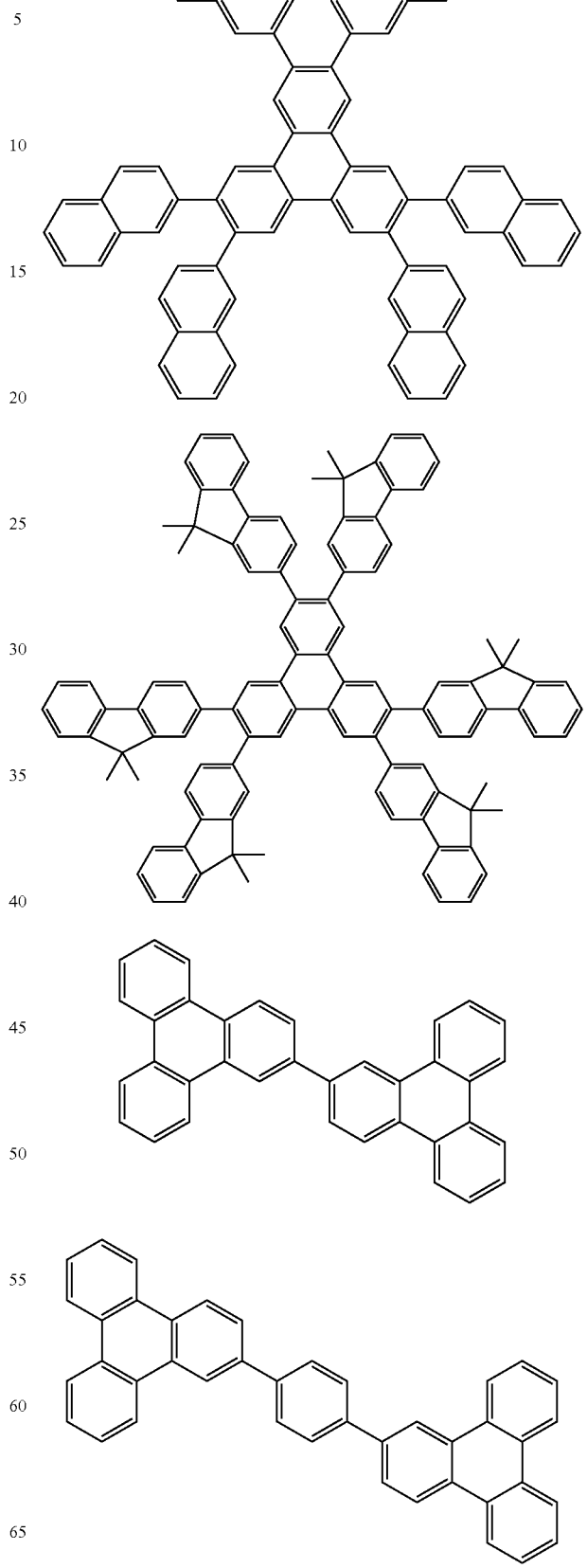

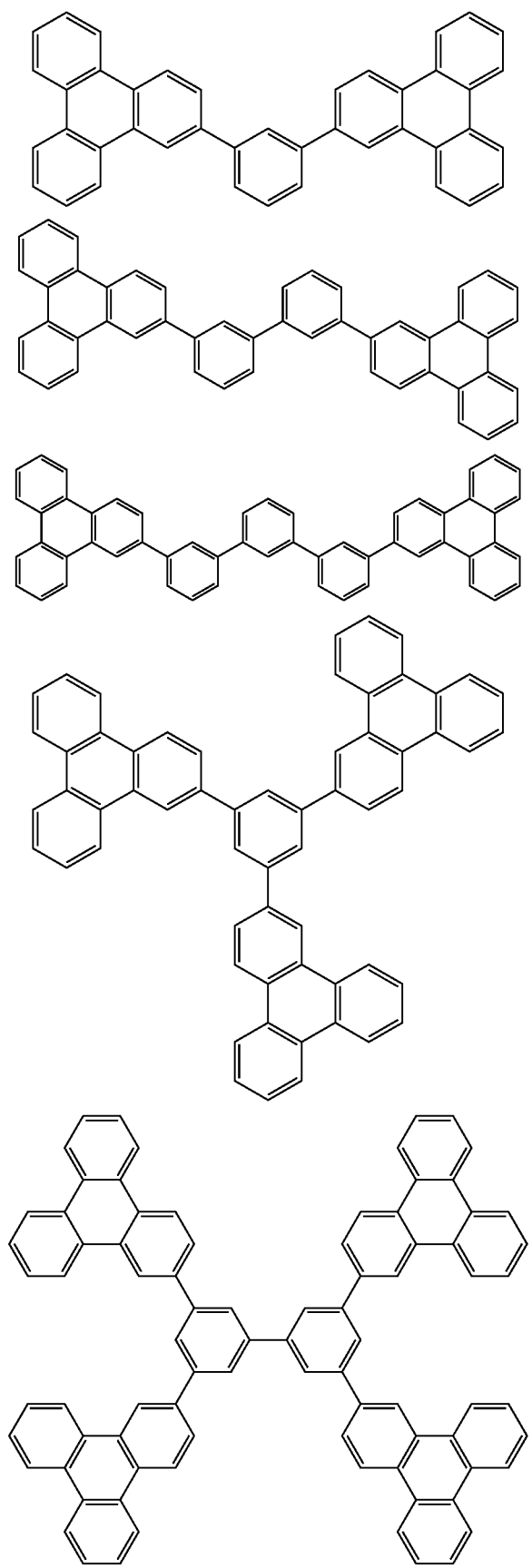
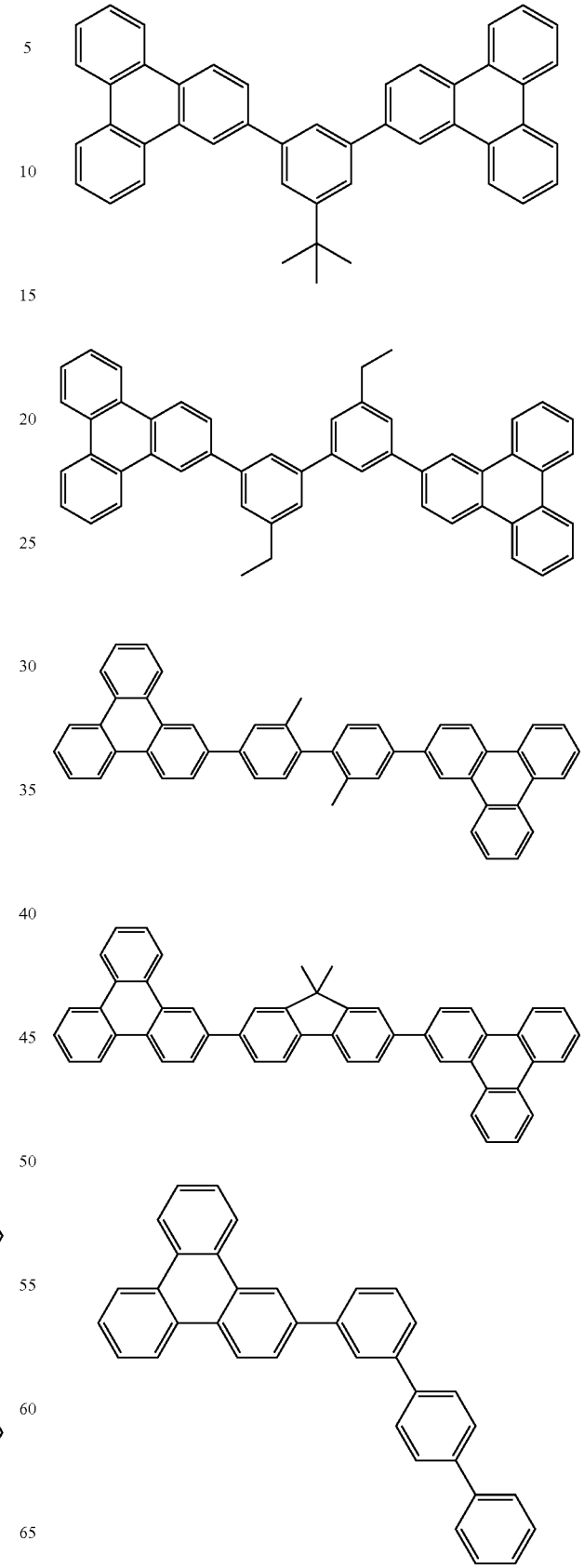
[Fifty-Fourth Chemical Formula]

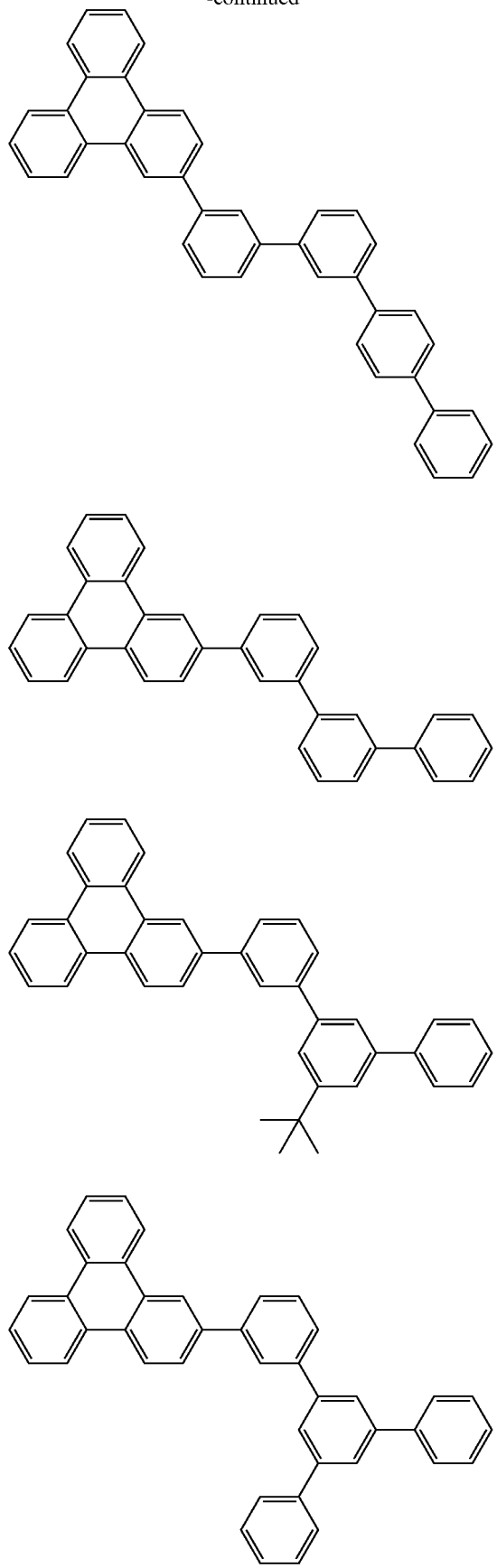

The compounds listed above as examples of the hydrocarbon compound according to the present invention can be synthesized by the methods described in a pamphlet of WO 05/013388, a pamphlet of WO 06/130598, a pamphlet of WO 09/021,107, US 2009/0009065, a pamphlet of WO 09/008,311, and a pamphlet of WO 04/018587.

After synthesis, it is preferable for purification by column chromatography, recrystallization, or the like to be performed, followed by sublimation purification. Sublimation purification not only allows organic impurities to be separated, bat also allows inorganic salts, residual solvents, and the like to be effectively removed.

(Compound Expressed by General Formula O-1)

The light-emitting element of the present invention preferably includes at least one organic layer between the light-emitting layer and the cathode, and from the standpoints of element efficiency and drive voltage, this organic layer preferably contains at least one type of compound expressed by General Formula O-1 below. General Formula O-1 will be described below,

[Fifty-Fifth Chemical Formula]

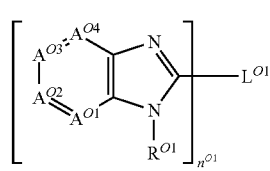

(O-1)

(In General Formula O-1, $R^{O1}$ represents an alkyl group, an aryl group, or a heteroaryl group. $A^{O1}$ to $A^{O4}$ represent each independently C—$R^A$ or a nitrogen atom. $R^A$ represents a hydrogen atom, an alkyl group, an aryl group, or a heteroaryl group, and the plurality of $R^A$ [groups] may be the same or different, represents a divalent to hexavalent linking group composed of an aryl ring or a heteroaryl ring. $n^{O1}$ represents an integer from 2 to 6.)

$R^{O1}$ represents an alkyl group (preferably $C_1$ to $C_8$), an aryl group (preferably $C_6$ to $C_{30}$), or a heteroaryl group (preferably $C_4$ to $C_{12}$), and these may have the aforementioned substituent Z'. $R^{O1}$ is preferably an aryl group or a heteroaryl group and more preferably an aryl group. Substituents that are preferable when the aryl group of $R^{O1}$ has a substituent include an alkyl group, an aryl group, and a cyano group, with an alkyl group or aryl group being more preferable, and an aryl group being even more preferable. If the aryl group of $R^{O1}$ has a plurality of substituents, the plurality of substituents may be bound to each other to form a five- or six-member ring. The aryl group of $R^{O1}$ is preferably a phenyl group that may have the substituent more preferably a phenyl group that may be substituted with an alkyl group or an aryl group, and even more preferably an unsubstituted phenyl group or a 2-phenylphenyl group.

$A^{O1}$ to $A^{O4}$ represent each independently C—$R^A$ or a nitrogen atom. Zero to two of $A^{O1}$ to $A^{O4}$ are preferably a nitrogen atom, and more preferably zero or one is a nitrogen atom. Preferably all of $A^{O1}$ to $A^{O4}$ are C—$R^A$, or $A^{O1}$ is a nitrogen atom and $A^{O2}$ to $A^{O2}$ are C—$R^A$, more preferably $A^{O1}$ is a nitrogen atom and $A^{O2}$ to $A^{O4}$ are C—$R^A$, and even more preferably $A^{O1}$ is a nitrogen atom, $A^{O2}$ to $A^{O4}$ are C—$R^A$, and all of the $R^A$ [groups] are hydrogen atoms.

$R^A$ represents a hydrogen atom, an alkyl group (preferably $C_1$ to $C_8$), an aryl group (preferably $C_6$ to $C_{30}$), or a heteroaryl group (preferably $C_4$ to $C_8$), and these may have the aforementioned substituent Z. Furthermore, the plurality of $R^A$ [groups] may be the same or different.

$R^A$ is preferably a hydrogen atom or an alkyl group and more preferably a hydrogen atom.

$L^{O1}$ represents a divalent to hexavalent linking group composed of an aryl ring (preferably $C_6$ to $C_{30}$) or a heteroaryl ring (preferably $C_4$ to $C_{12}$). $L^{O1}$ is preferably an arylene group, a heteroarylene group, an aryltolyl group, or a heteroaryltolyl group, more preferably a phenylene group, a biphenylene group, or a benzenetriyl group, and even more preferably a biphenylene group or a benzenetriyl group. $L^{O1}$ may have the aforementioned substituent Z', and if there is a substituent, the substituent is preferably an alkyl group, an aryl group, or a cyano group. Concrete examples of $L^{O1}$ are listed below.

[Fifty-Sixth Chemical Formula]

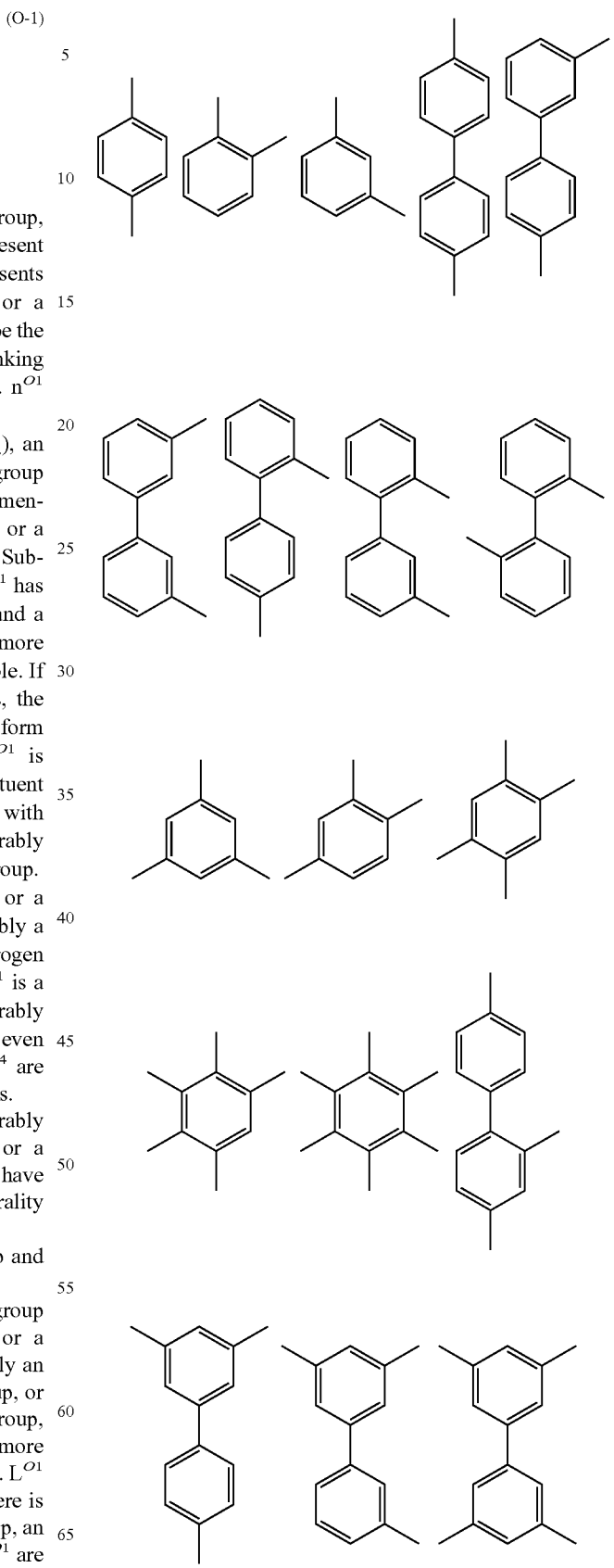

-continued

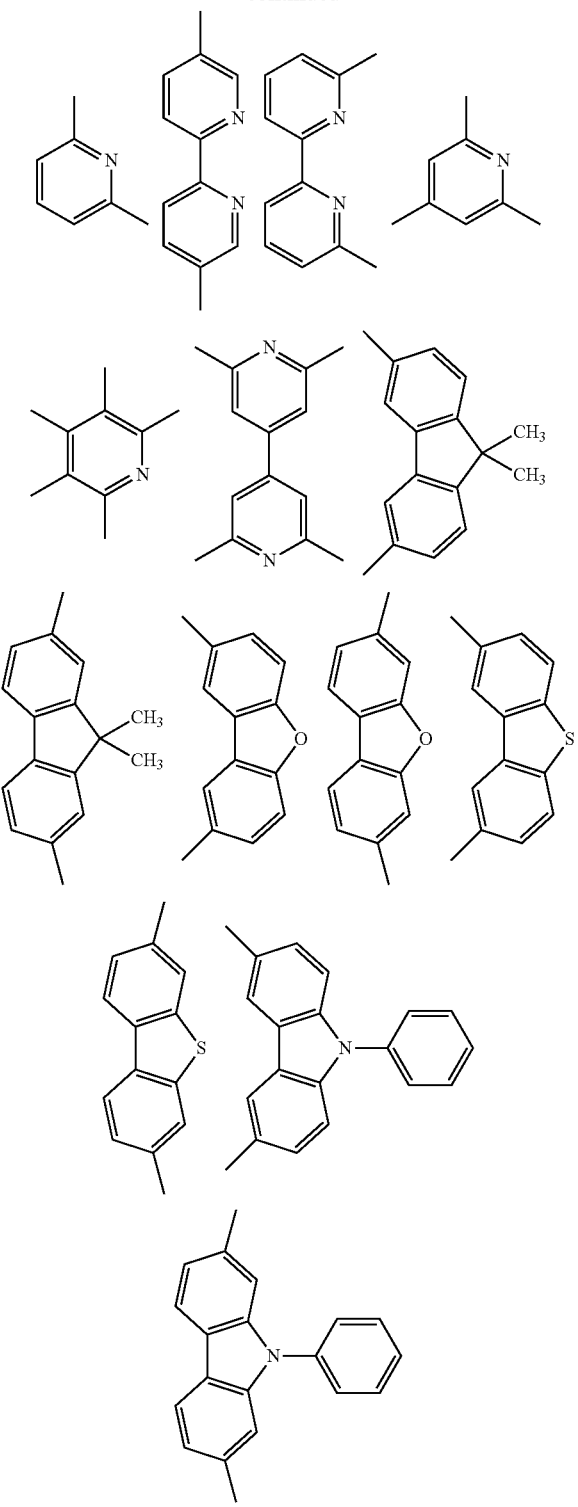

$n^{O1}$ represents an integer from 2 to 6, preferably an integer from 2 to 4, and more preferably 2 or 3. From the standpoint of element efficiency, $n^{O1}$ is most preferably 3, and from the standpoint of durability of the element, 2 is most preferable.

The compound expressed by General Formula O-1 is more preferably a compound expressed by General Formula O-2 below.

[Fifity-Seventh Chemical Formula]

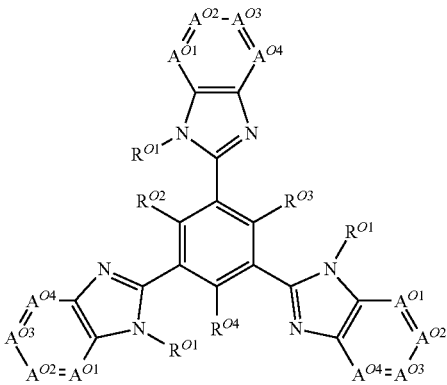

(O-2)

(In General Formula O-2, $R^{O4}$ represents an alkyl group, an aryl group, or a heteroaryl group $R^{O2}$ to $R^{O4}$ represent each independently a hydrogen atom, an alkyl group, an aryl group, or a heteroaryl group. $A^{O1}$ to $A^{O4}$ represent each independently C—$R^A$ or a nitrogen atom. $R^A$ represents a hydrogen atom, an alkyl group, an aryl group, or a heteroaryl group, and the plurality of $R^A$ [groups] may be the same or different.)

$R^{O1}$ and $A^{O1}$ to $A^{O4}$ are defined the same as $R^{O1}$ and $A^{O1}$ to $A^{O4}$ in General Formula O-1 above, and the preferred ranges thereof are also the same.

$R^{O2}$ to $R^{O4}$ represent each independently a hydrogen atom, an alkyl group (preferably $C_1$ to $C_8$), an aryl group (preferably $C_6$ to $C_{30}$), or a heteroaryl group (preferably $C_4$ to $C_{12}$), and these may have the aforementioned substituent Z'. $R^{O2}$ to $R^{O4}$ are preferably a hydrogen atom, an alkyl group, or an aryl group, more preferably a hydrogen atom or an aryl group, and most preferably a hydrogen atom.

From the standpoints of stability during high-temperature storage and stable operation with respect to heat emission during, high-temperature drive and during drive [sic], the glass transition temperature (Tg) of the compound expressed by General Formula O-1 above is preferably between 100° C. and 300° C., more preferably between 120° C. and 300° C., even more preferably between 120° C. and 300° C. [sic], and even still more preferably between 140° C. and 300° C.

Concrete examples of the compound expressed by General Formula O-1 are given below, but the present invention is not limited to or by these.

[Fifty-Eighth Chemical Formula]

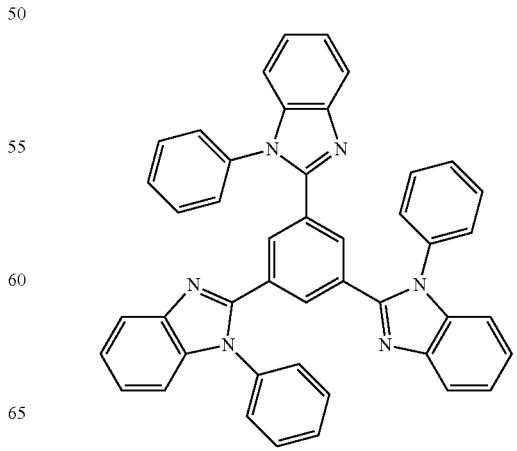

OM-1

OM-2
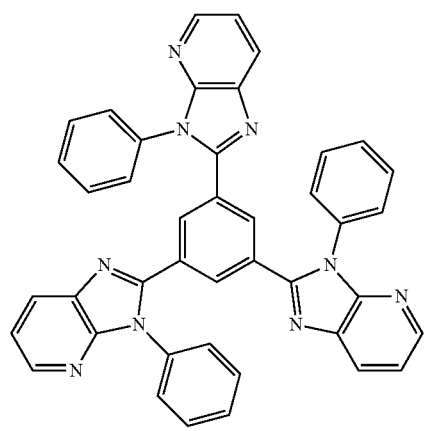
OM-3
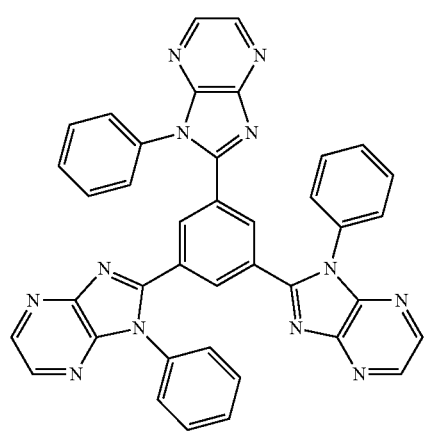
OM-4
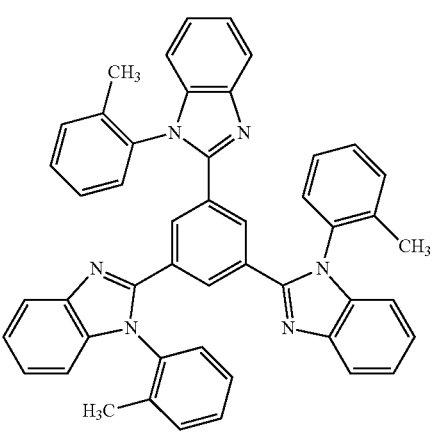
OM-5
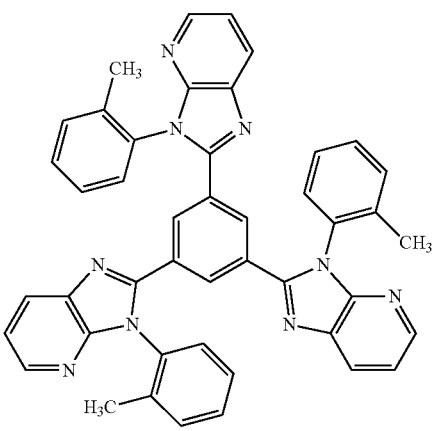
OM-6
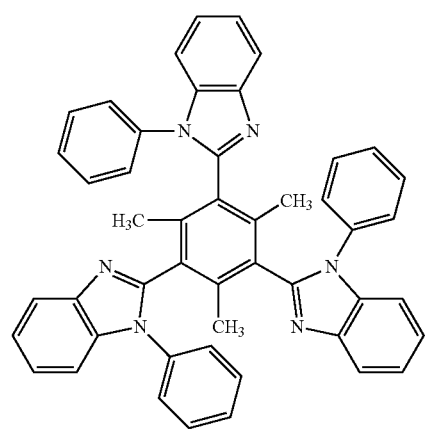
OM-7
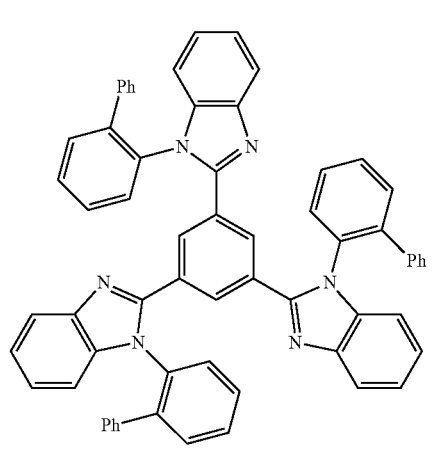

OM-8
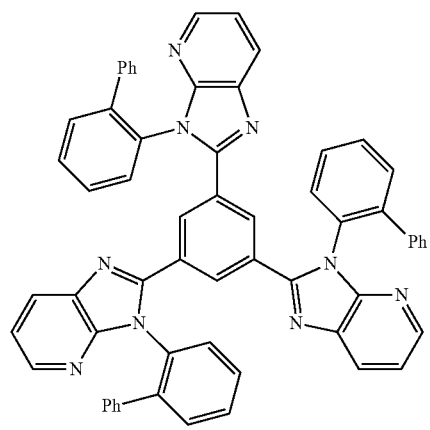
OM-9
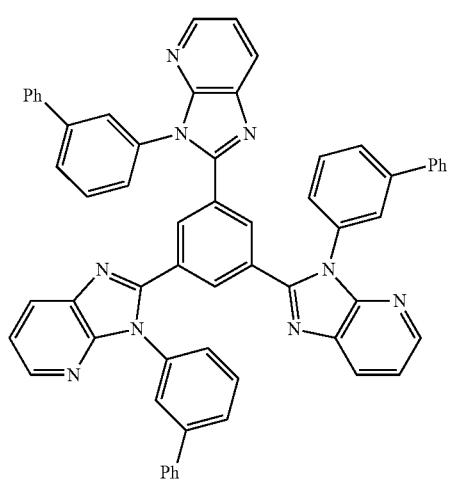
[Fifty-Ninth Chemical Formula]
OM-10
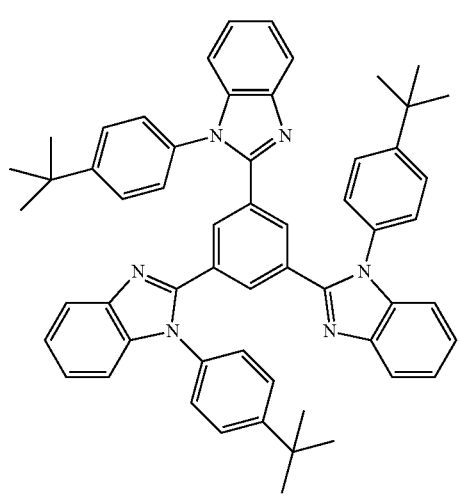
OM-11
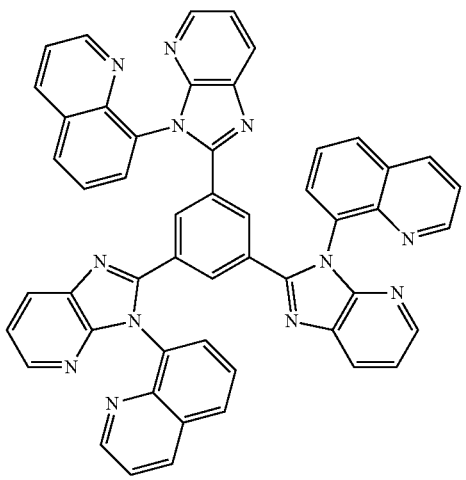
OM-12
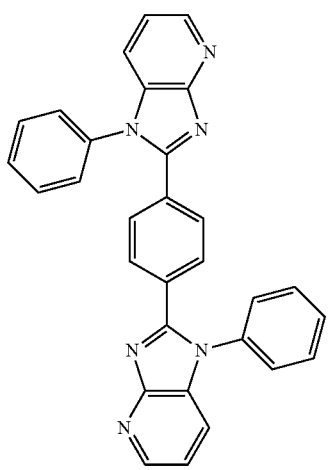
OM-13
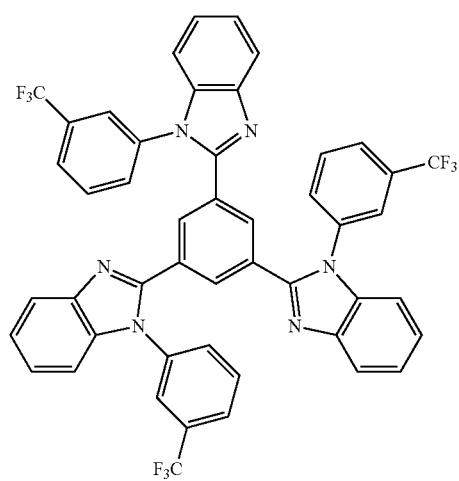

OM-14

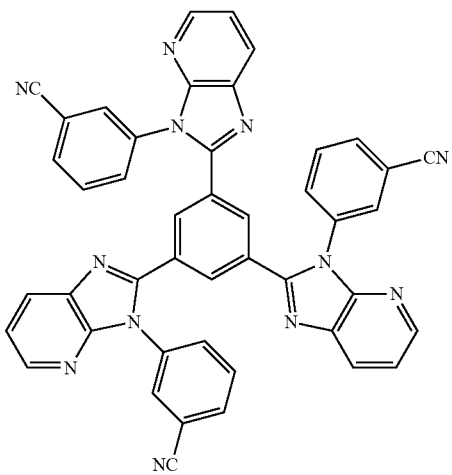

OM-15

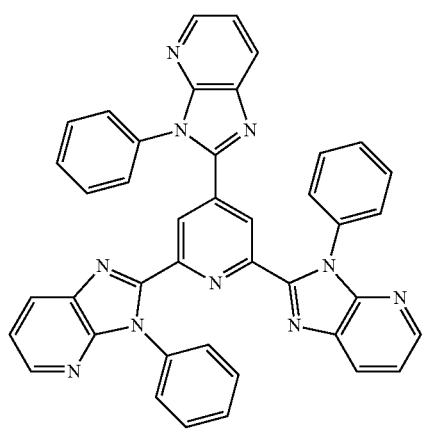

OM-16

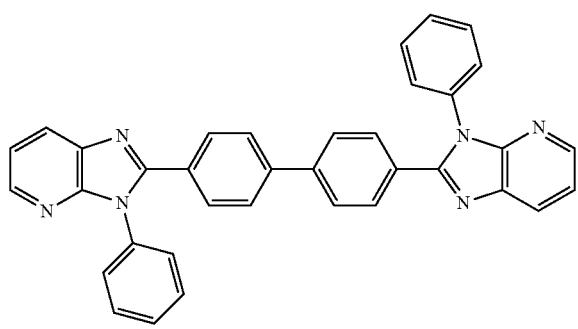

The compound expressed by General Formula O-1 above can be synthesized by the method described in Japanese Laid-Open Patent Application 2001-335776. After synthesis, it is preferable for purification by column chromatography, recrystallization, reprecipitation, or the like to be performed, followed by sublimation purification. Sublimation purification not only allows organic impurities to be separated, but also allows inorganic salts, residual solvents, moisture, and the like to be effectively removed.

In the light-emitting element of the present invention, the compound expressed by General Formula O-1 is contained in an organic layer between the light-emitting layer and the cathode, but is preferably contained in the layer adjacent to the light-emitting layer on the cathode side.

(Charge Transport Layer)

[The term] "charge transport layer" refers to a layer in which charge movement occurs when voltage is applied to the organic electroluminescent element.

Concrete examples include a hole injection layer, a hole transport layer, an electron blocking layer, a light-emitting layer, a hole blocking layer, an electron transport layer, or an electron injection layer. The hole injection layer, the hole transport layer, the electron blocking layer, or the light-emitting layer is preferable. If the charge transport layer formed by coating is the hole injection layer, the hole transport layer, the electron blocking layer, or the light-emitting layer, a low-cost and high-efficiency organic electroluminescent element can be manufactured. Moreover, the charge transport layer is more preferably the hole injection layer, the hole transport layer, or the electron blocking layer.

(Hole Injection Layer and Hole Transport Layer)

The hole injection layer and the hole transport layer are layers having the function of accepting holes from the anode or the anode side and transporting them to the cathode side.

Regarding the hole injection layer and the hole transport layer, what is stated in paragraph [0165] in Japanese Laid-Open Patent Application 2008-270736 can be applied to the present invention.

The hole injection layer preferably contains an electron accepting dopant. The effects of having the hole injection layer contain an electron accepting dopant are that hole injection is enhanced, drive voltage decreases, efficiency is higher, and so forth. The electron accepting dopant may be either an organic material or inorganic material as long as it is a material capable of pulling electrons from the doped material and generating radical cations, but examples include tetracyanoquinodimethane (TCNQ), tetrafluorotetracyanoquinodimethane ($F_4$-TCNQ), and molybdenum oxide.

The electron accepting dopant in the hole injection layer is preferably contained in at amount of 0.01 to 50 wt %, more preferably 0.1 to 40 wt %, and even more preferably 0.2 to 30 wt %, with respect to the total weight of the compound forming the hole injection layer.

(Electron Injection Layer and Electron Transport Layer)

The electron injection layer and the electron transport layer are layers having the function of accepting electrons from the cathode or the cathode side and transporting them to the anode side. The electron injection material and electron transport material used for these layers may be compounds with either a low or a high molecular weight.

The compounds expressed by any of General Formulas 1 to 3 of the present invention can be used as electron transport materials. For other materials, [the electron injection layer and the electron transport layer] are preferably layers containing a pyridine derivative, a quinoline derivative, a pyrimidine derivative, a pyrazine derivative, a phthalazine derivative, a phenanthroline derivative, a triazine derivative, a triazole derivative, an oxazole derivative, an oxadiazole derivative, an imidazole derivative, a fluorenone derivative, an anthraquinodimethane derivative, an anthrone derivative, a diphenylquinone derivative, a thiopyran dioxide derivative, a carbodiimide derivative, a fluorenylidenemethane derivative, a distyrylpyrazine derivative, an aromatic tetracarboxylic acid anhydride of naphthalene, perylene, etc., a phthalocyanine derivative, various metal complexes typified by a metal complex of an 8-quinolinol derivative (such as tris(8-hydroxyquinolinato)aluminum (abbreviated as Alq)) and a metal complex containing metal phthalocyanine benzoxazole, or benzothiazole as a ligand, an organic silane derivative typified by silole, and the like.

From the standpoint of lowering the drive voltage, the thickness of the electron injection layer and electron transport layer is preferably no more than 500 nm for each.

The thickness of the electron transport layer is preferably 1 to 500 nm, more preferably 5 to 200 nm, and even more preferably 10 to 100 nm, in addition, the thickness of the electron injection layer is preferably 0.1 to 200 nm, more preferably 0.2 to 100 nm, and even more preferably 0.5 to 50 nm.

The electron injection layer and the electron transport layer may have a single-layer structure composed of one or more types of the aforementioned materials, or a multilayer structure composed of a plurality of layers of the same composition or different compositions. From the standpoints of drive voltage, luminous efficiency, and durability, a multilayer structure composed of a plurality of layers of different compositions is preferable.

The electron injection layer preferably contains an electron donating dopant. The effects of having the electron injection layer contain an electron donating dopant are that electron injection is enhanced; drive voltage decreases, efficiency is higher, and so forth. The electron donating dopant may be either an organic material or inorganic, material as long as it is a material capable of giving electrons to the doped material and generating radical anions, but examples include tetrathiafulvalene (TTF), tetrathianaphthacene (TTT) [sic][4], bis-[1,3-diethyl-2-methyl-1,2-dihydrobenzimidazolyl] and other such dihydroimidazole compounds, lithium, and cesium.

[4] Translator's note: The abbreviation of "tetrathianaphthacene" should be "TTN," and "TTT" is "tetrathiatetracene," so this abbreviation "TTT" here seems to be an error in the original for "TTN."

The electron donating dopant in the electron injection layer is preferably contained in an amount of 0.01 to 50 wt %, more preferably 0.1 to 40 wt %, and even more preferably 0.5 to 30 wt %, with respect to the total weight of the compound forming the electron injection layer.

(Intermediate Layer)

The organic electroluminescent element of the present invention has the aforementioned electron transport layer between the aforementioned light-emitting layer and the aforementioned cathode, and an intermediate layer can be provided between this electron transport layer and the aforementioned light-emitting layer. By providing the intermediate layer, it is possible to lower the drive voltage, to improve efficiency of the element, and to increase durability.

The intermediate layer preferably contains a compound expressed by any of General Formulas 1 to 3 above. A hole blocking layer (described later) is an example of an intermediate layer.

(Hole Blocking Layer)

The hole blocking layer is a layer having the function of preventing the holes transported from the anode side to the light-emitting layer from escaping to the cathode side. In the present invention, a hole blocking layer can be provided as an organic layer that is adjacent to the light-emitting layer on the cathode side.

Examples of organic compounds that constitute a hole blocking layer include aluminum(III) bis(2-methyl-8-quinolinato) 4-phenylphenolate (abbreviated as BAlq) and other such aluminum complexes, triazole derivatives, and phenanthroline derivatives such as 2,9-dimethyl-4,7-diphenyl-1,10-phenanthroline (abbreviated as BCP).

The thickness of the hole blocking layer is preferably 1 to 500 nm, more preferably 5 to 200 nm, and even more preferably 10 to 100 nm.

The hole blocking layer may have a single-layer structure composed of one (IT more types of the aforementioned materials, or may have a multilayer structure composed of a plurality of layers of the same composition or different compositions.

(Electron Blocking Layer)

The electron blocking layer is a layer having the function of preventing the electrons transported from the cathode side to the light-emitting layer from escaping to the anode side. In the present invention, an electron blocking layer can be provided as an organic layer that is adjacent to the light-emitting layer on the anode side.

As examples of organic, compounds that constitute an electron blocking layer, those listed above as examples of hole transport materials can be used.

The thickness of the electron blocking layer is preferably 1 to 500 nm, more preferably 5 to 200 nm, and even more preferably 10 to 100 nm.

The electron blocking layer may have a single-layer structure composed of one or more types of the aforementioned materials, or may have a multilayer structure composed of a plurality of layers of the same composition or different compositions.

(Protective Layer)

In the present invention, the entire organic EL element may be protected by a protective layer.

Regarding the protective layer, what is stated in paragraphs [0169] and [0170] in Japanese Laid-Open Patent Application 2008-270736 can be applied to the present invention.

(Sealing Container)

The element of the present invention may be entirely sealed by using a sealing container.

Regarding the sealing container, what is stated in paragraph [0171] in Japanese Laid-Open Patent Application 2008-270736 can be applied to the present invention.

(Drive)

The organic electroluminescent element of the present invention can emit light by applying direct current (may include an alternating current component as needed) voltage (usually 2 to 15 volts) or DC current between the anode and the cathode.

For the method for driving the organic electroluminescent element of the present invention, the drive methods described in the Specifications or the like of Japanese Laid-Open Patent Applications H2-148687, 116-301355, H5-29080, H7-134558, H8-234685, and H8-241047, Japanese Patent 2,784,615, and U.S. Pat. Nos. 5,828,429 and 6,023,308 can be applied.

The external quantum efficiency of the organic electroluminescent element of the present invention is preferably at least 7%, more preferably at least 10%, and even more preferably at least 12%. The numerical value of external quantum efficiency that can be used is the maximum value for external quantum efficiency when the element is driven at 20° C., or the value for external quantum efficiency near 300 to 400 $cd/m^2$ when the element is driven at 20° C.

The internal quantum efficiency of the organic, electroluminescent element of the present invention is preferably at least 30%, more preferably at least 50%, and even more preferably at least 70%. The internal quantum efficiency of the element is calculated by dividing the external quantum efficiency by the light extraction efficiency. The light extraction efficiency is approximately 20% with an ordinary organic EL element, but the light extraction efficiency can be raised to over 20% by modifying the shape of the substrate, the shape of the electrodes, the thickness of the organic layers, the thickness of the inorganic layers, the refractive index of the organic layers, the refractive index of the inorganic layers, and so forth.

(Application of the Element of the Present Invention)

The element of the present invention can be utilized favorably in display elements, displays, backlights, electronic photography, illumination light sources, recording light sources, exposure light sources, reading light sources, road signs, trade signs, interior decorating, optical communications, and so forth, [This element] can be used to particular advantage in devices that are driven in areas of high light emission brightness, such as in lighting devices and display devices.

(Light-emitting Device)

Next, the light-emitting device of the present invention will be described with reference to FIG. 2.

The light-emitting device of the present invention makes use of the aforementioned organic electroluminescent element.

Figure 2:
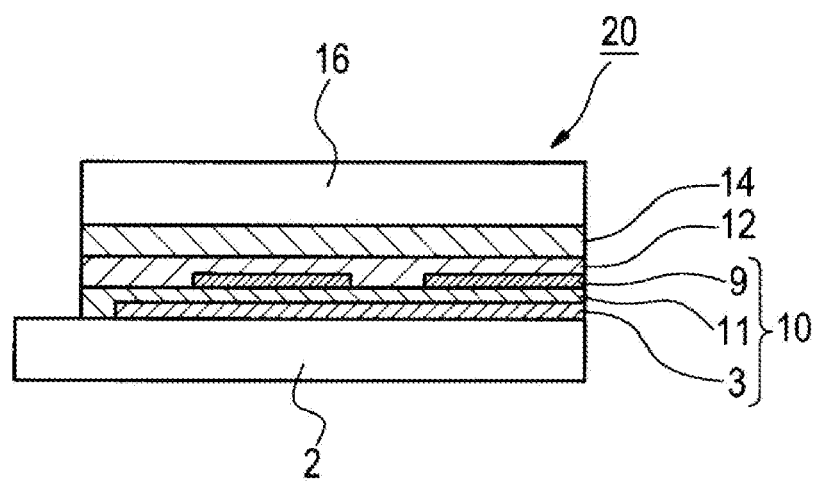
FIG. 2 is a schematic diagram illustrating one example of the light-emitting device according to the present invention.

FIG. 2 is a sectional view schematically showing one example of the light-emitting device of the present invention. The light-emitting device 20 in FIG. 2 is made up of a substrate (supporting substrate) 2, an organic electroluminescent element 10, a sealing container 16, and the like.

The organic, electroluminescent element 10 is configured such that an anode (first electrode) 3, an organic layer 11, and a cathode (second electrode) 9 are laminated in that order on the substrate 2. Furthermore, a protective layer 12 is laminated on the cathode 9, and in addition, the sealing container 16 is provided on the protective layer 12 via an adhesive layer 14. Note that parts of the electrodes 3 and 9, partitions, insulating layers, and so forth are not depicted.

Here, an epoxy resin or other such photosetting adhesive or thermosetting adhesive can be used as the adhesive layer 14. For example, a thermosetting adhesive sheet can also be used.

There are no particular restrictions on the applications of the light-emitting device of the present invention, but examples other than lighting devices include television sets, personal computers, portable telephones, electronic paper, and other such display devices.

(Lighting Devices)

Next, the lighting device of the present invention will be described with reference to FIG. 3.

Figure 3:
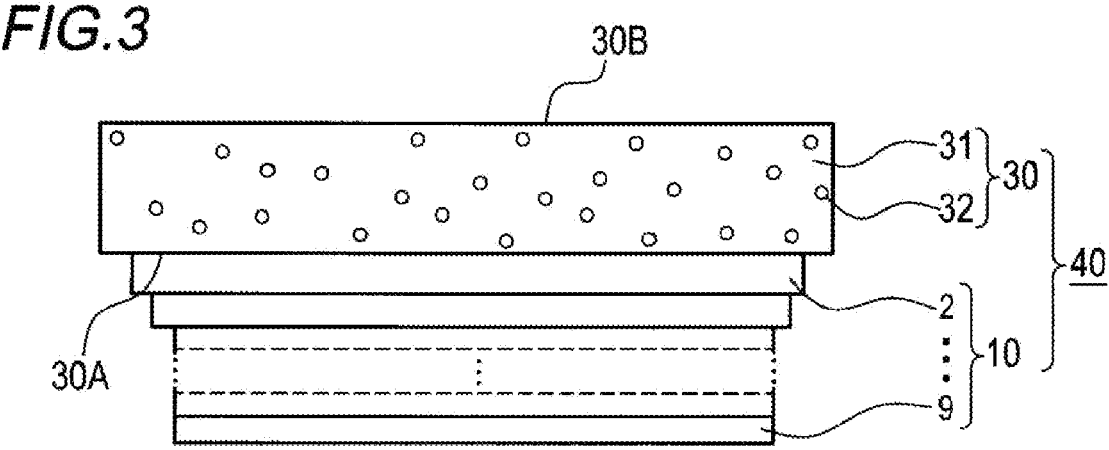
FIG. 3 is a schematic diagram illustrating one example of the lighting device according to the present invention.

FIG. 3 is a sectional view schematically showing one example of the lighting device of the present invention. As is shown in FIG. 3, the lighting device 40 of the present invention comprises the aforementioned organic electroluminescent element 10 and a light scattering member 30. More concretely, the lighting device 40 is configured such that the substrate 2 of the organic electroluminescent element 10 is in contact with the light scattering member 30.

There are no particular restrictions on the light scattering member 30 as long as it is capable of scattering light, but in FIG. 3, it is a member in which microparticles 32 are dispersed in a transparent substrate 31. A glass substrate can be used favorably as the transparent substrate 31, for example. Transparent resin microparticles can be used favorably as the microparticles 32. The glass substrate and the transparent resin microparticles can both be from prior art. This type of lighting device 40 is devised such that when light emitted from the organic electroluminescent element 10 is incident on a light incidence face 30A of the light scattering member 30, the incident light is scattered by the light scattering member 30, and the scattered light exits a light emission face 30B as illuminating light.

WORKING EXAMPLES

The present invention will now be described in further detail based on working examples, but the present invention is not limited to or by these.

1. Synthesis Examples

Synthesis Example 1

Synthesis of Compound 1-2

[Sixtieth Chemical Formula]

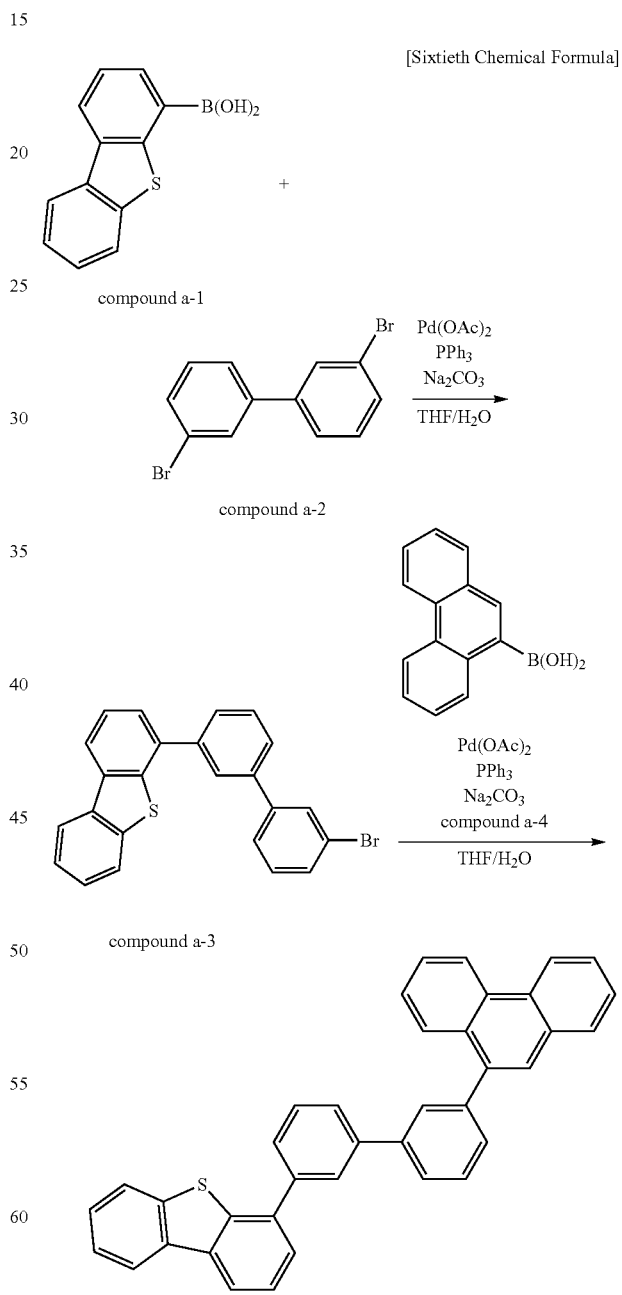

55.8 g of sodium Uril carbonate, 300 mL of THF, and 300 mL of distilled water were put into a 1-L three-mouth flask, which was deaerated under reduced pressure, and nitrogen replacement was performed. 6.9 g of triphenylphosphine, 41 g of 3,3'-dibromobiphenyl (compound a-2), 1.48 g of palladium acetate, and 30 g of compound a-1 (made by Wako Pure Chemical Industries, Ltd.) were added in that order under stirring and were reacted for 5 hours at an external temperature of 80° C. [The system] was returned to room temperature, 100 mL of toluene was added, and the aqueous phase was removed. The organic phase was condensed under reduced pressure and purified by silica gel column chromatography using an eluant of ethyl acetate/hexane (1/9 volumetric ratio), which gave 5 g of compound a-3.

Figure 4:
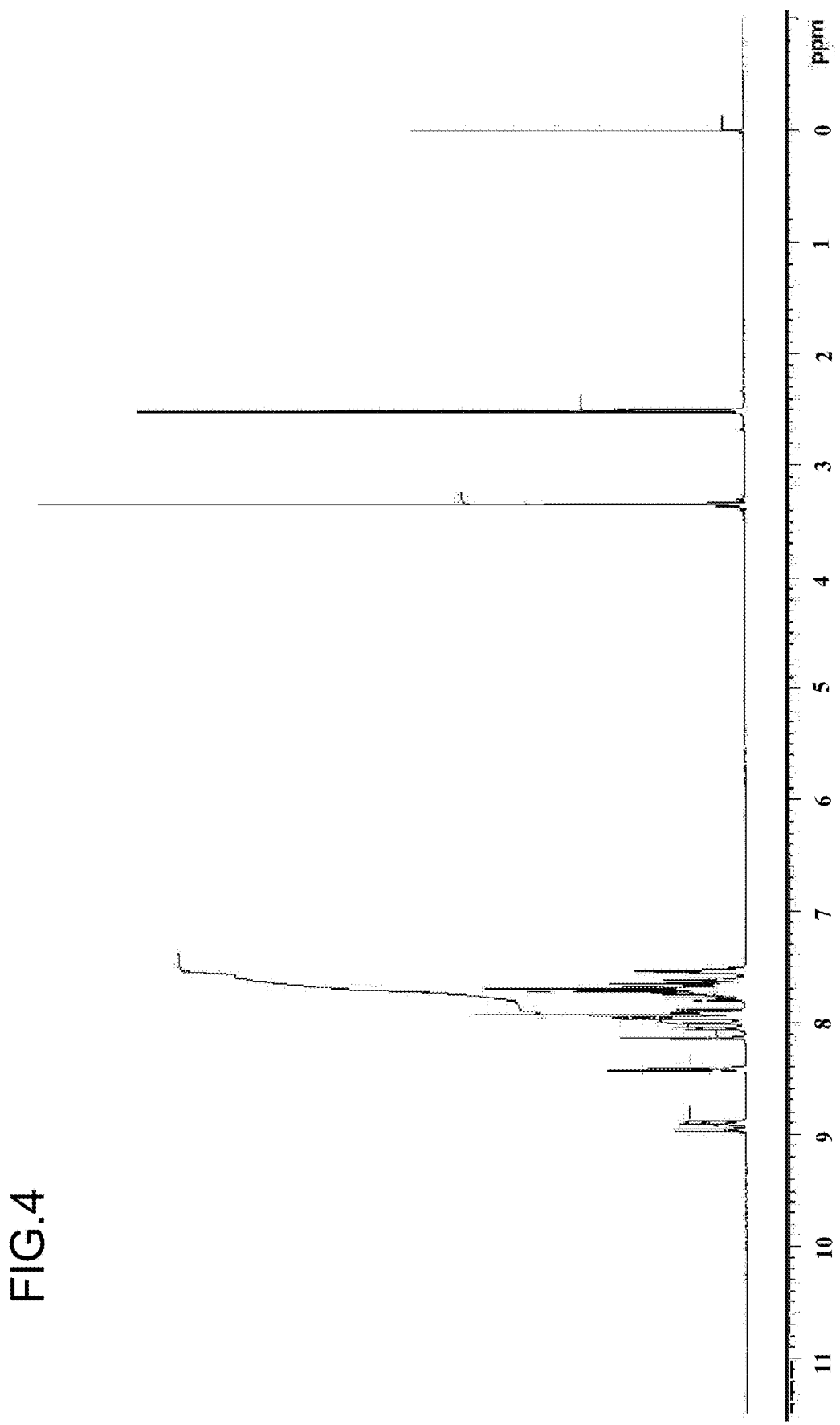
FIG. 4 is a graph of the $^1$H-NMR spectrum of compound 1-2 that is synthesized according to Synthesis Example 1.

2 g of compound a-3, 2 g of sodium carbonate, 20 mL of THF, and 20 mL of distilled water were put in a 2.00-mL three-mouth flask, which was deaerated under reduced pressure, and nitrogen replacement was performed. 0.25 g of triphenylphosphine, 54 mg of palladium acetate, and 1.2 g of compound a-4 (made by Wako Pure Chemical Industries, Ltd.) were added in that order under stirring and were reacted for 5 hours at an external temperature of 80° C. [The system] was returned to room temperature, 20 mL of toluene was added, and the aqueous phase was removed. The organic phase was condensed under reduced pressure and purified by silica gel column chromatography using an eluant of toluene/hexane (1/1 volumetric ratio). The purified white solid was dispersed in 50 mL of hexane, heated under stirring, and heated under reflux for 30 minutes, after which the precipitate was subjected to suction filtration before cooling down. This procedure was performed twice, which gave 1.9 g of white solid. Sublimation purification was then performed which gave 1 g of compound 1-2. The resulting compound 1-2 was identified by $^1$H-NMR. The $^1$H-NMR data are shown in FIG. 4.

Synthesis Examples 2 to 8

Synthesis of Compound 1-1, Compounds 1-4 to 1-8, and Compound 1-58

The compounds 1-1, 14 to 1-8, and 1-58 were synthesized by the following scheme: The reaction conditions and purification procedure were the same as in Synthesis Example 1. Compounds 1-1 and 1-5 were synthesized under the same reaction and purification conditions as compounds 1-2 and 1-6, using compounds in which the dibenzothiophene structure of the compounds used in synthesizing compounds 1-2 and 1-6, respectively, was substituted for a dibenzofuran structure.

[Sixty-First Chemical Formula]

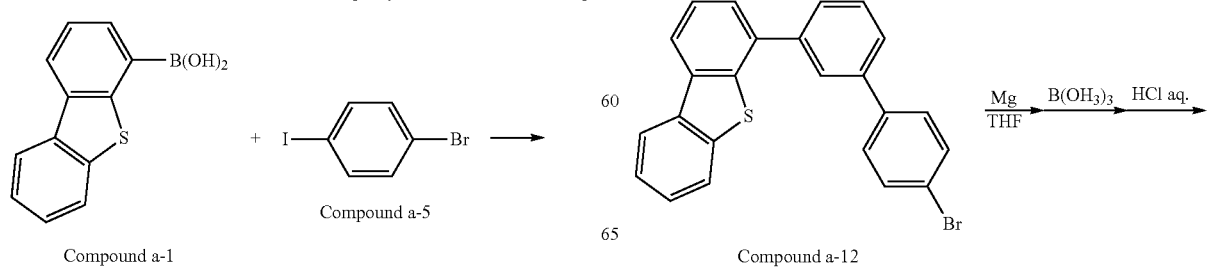

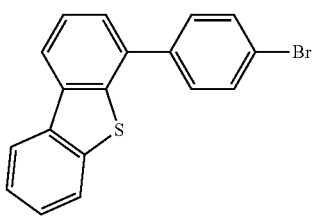

Compound a-6

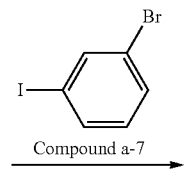

Compound a-7

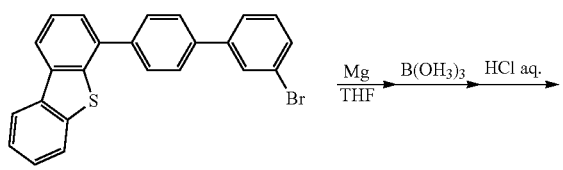

Compound a-11

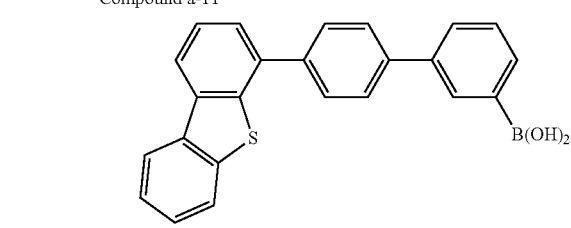

Compound a-13

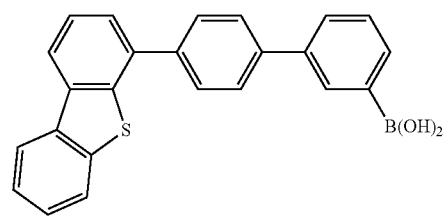

Compound a-1

Compound a-7

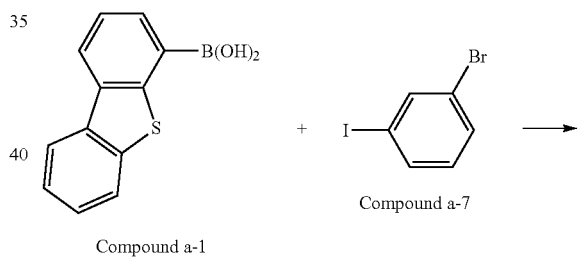

Compound a-8

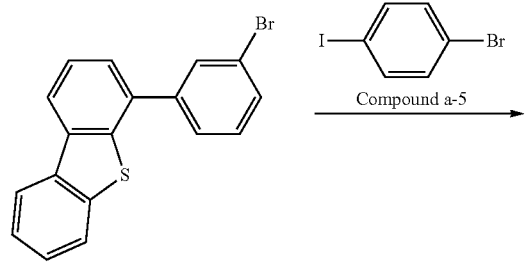

Compound a-12

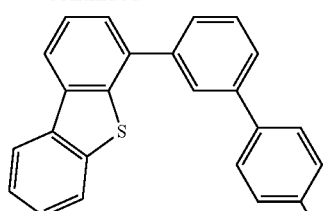
Compound a-14
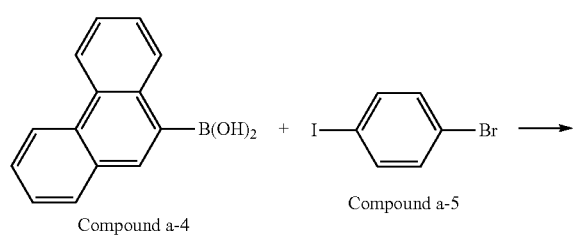
Compound a-4 + Compound a-5 →
Compound a-9
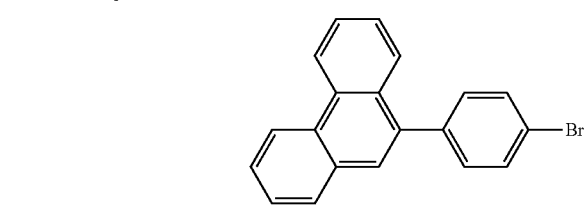
Compound a-4 + Compound a-5 →
Compound a-10
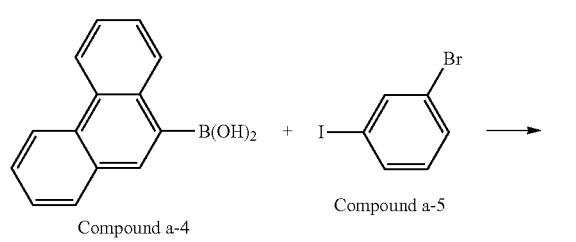
Compound a-13 +
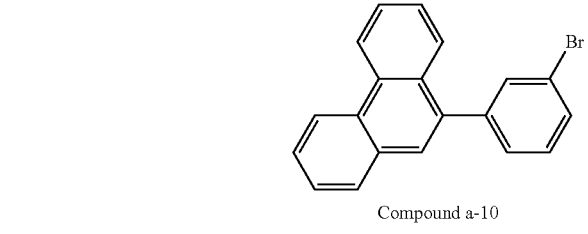
Compound a-9
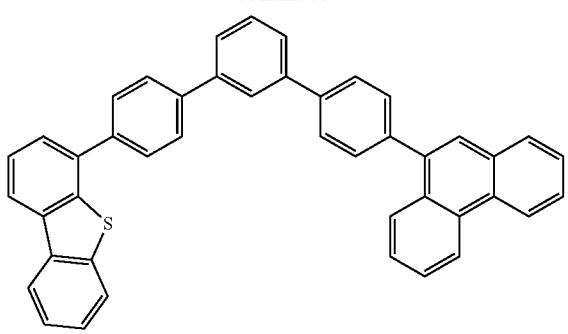
Compound 1-4
[Sixty-Second Chemical Formula]
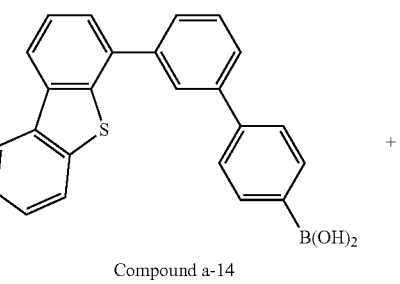
Compound a-14
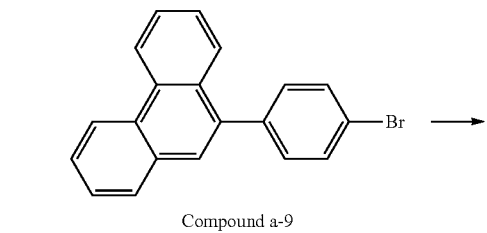
Compound a-9 →
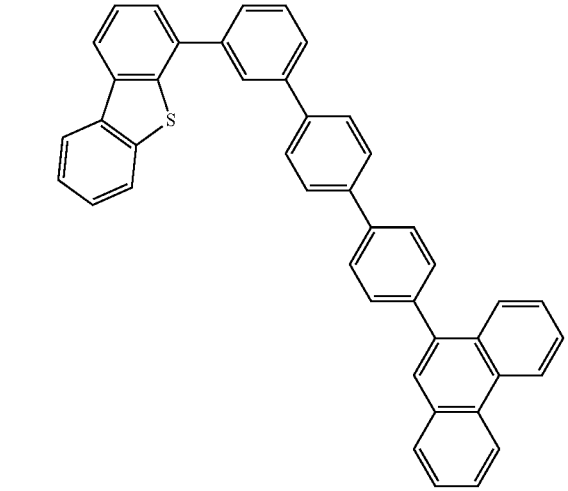
Compound a-6
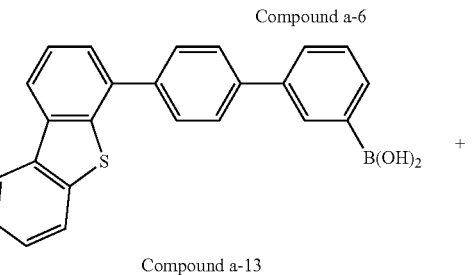
Compound a-13 +

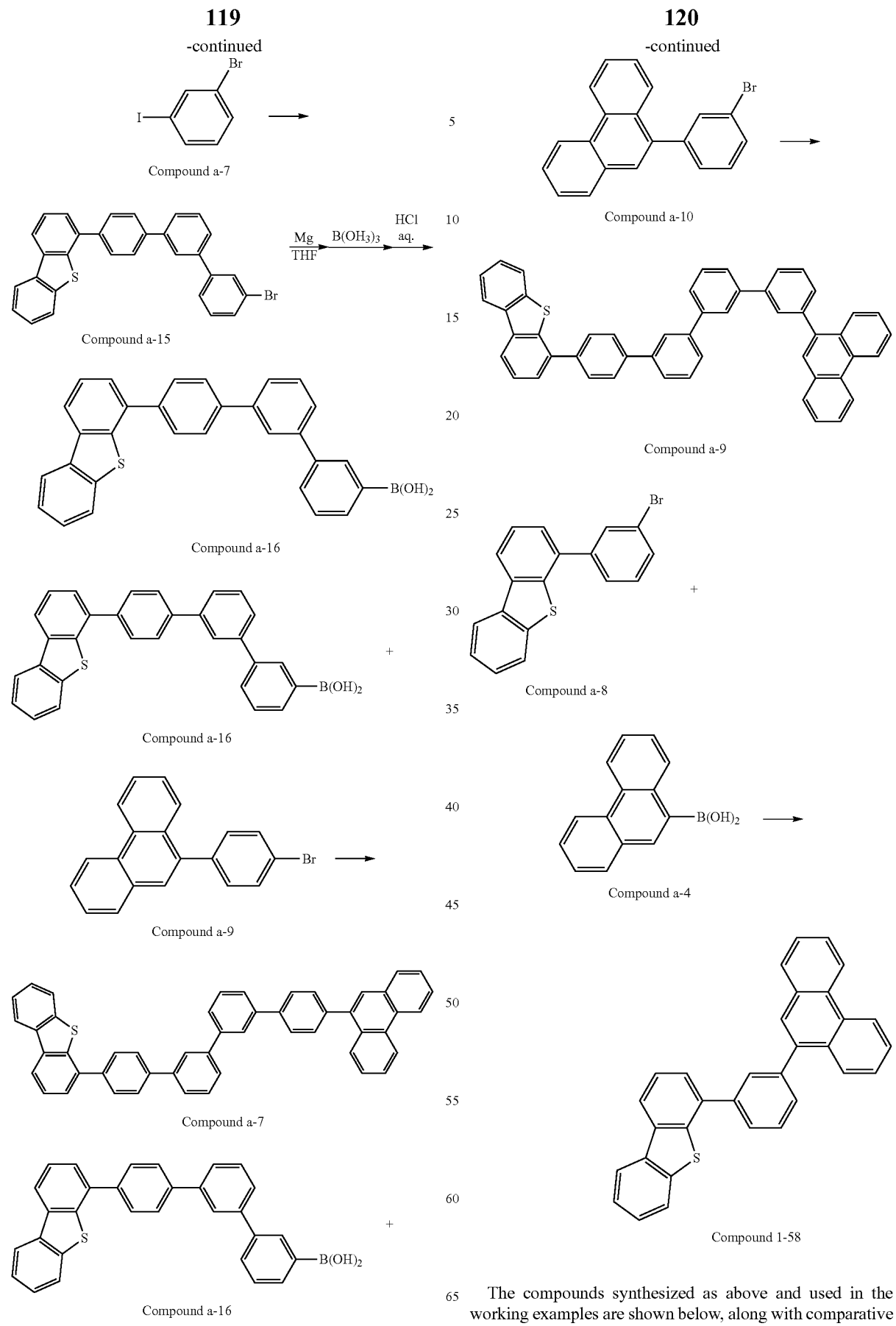
The compounds synthesized as above and used in the working examples are shown below, along with comparative compounds also used in the working examples.

[Sixty-Third Chemical Formula]

compound 1-1

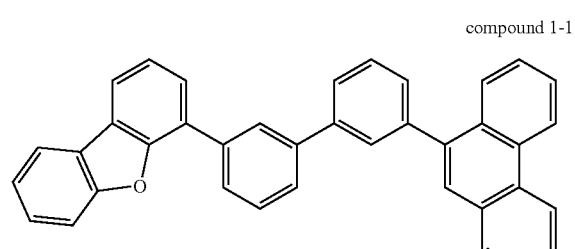

compound 1-2

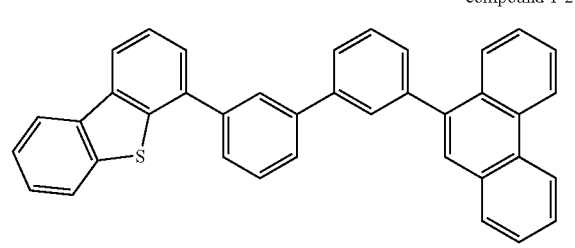

compound 1-4

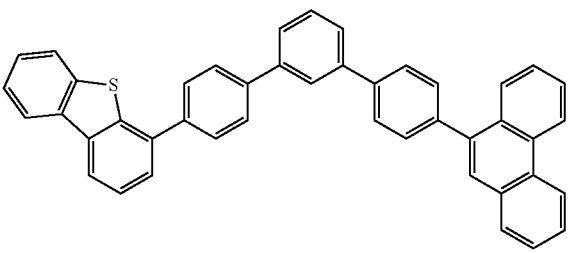

compound 1-5

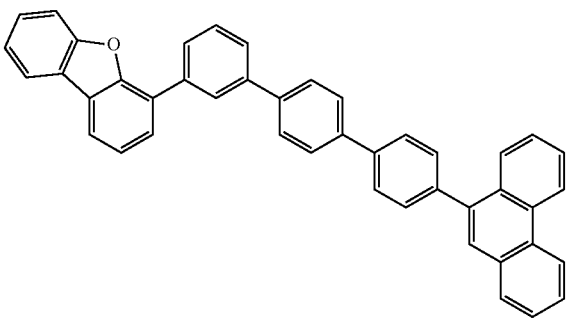

compound 1-6

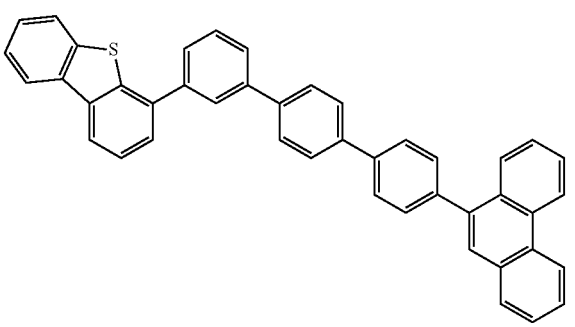

compound 1-7

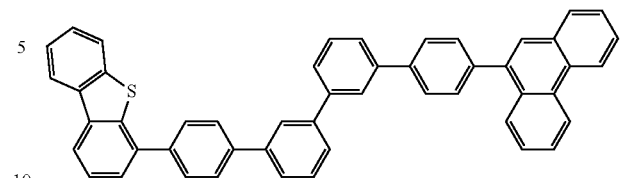

compound 1-8

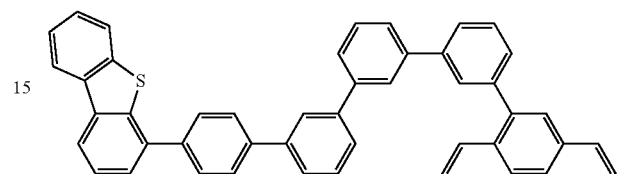

[Sixty-Fourth Chemical Formula]

compound 1-58

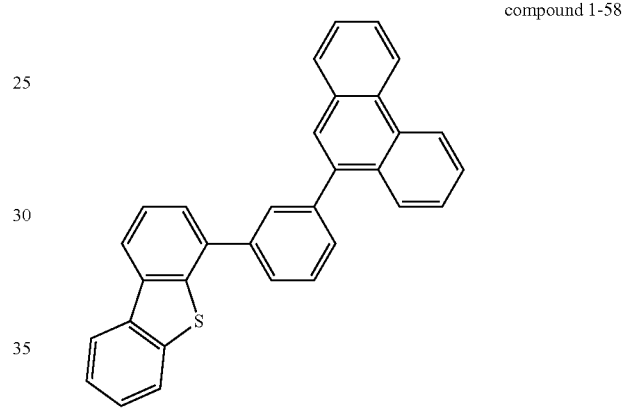

Comparative compounds 1 and 2: the compounds described in a pamphlet of WO 07/069,569

Comparative compound 3: the compound described in JP 2008-545729

Comparative compound 4: the compound described in a pamphlet of WO 09/021126

[Sixty-Fifth Chemical Formula]

comparative compound 1

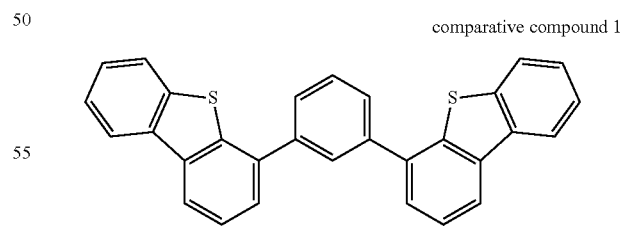

comparative compound 2

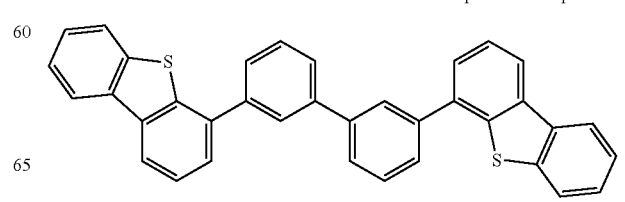

-continued comparative compound 3

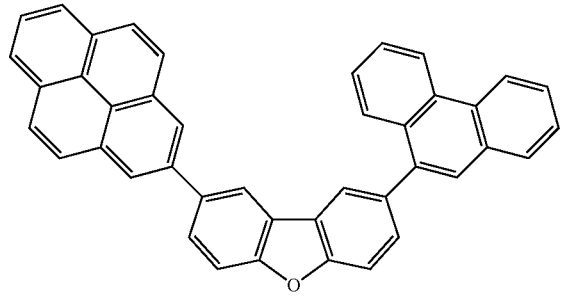

comparative compound 4

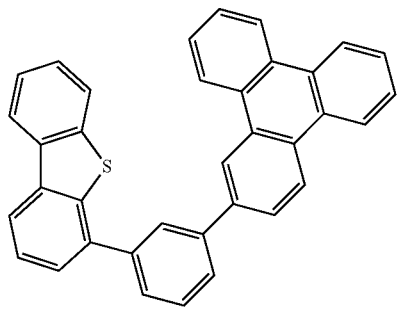

2. Element Production and Evaluation

All the materials used in element production were subjected to sublimation purification, and it was confirmed by high-performance liquid chromatography (Tosoh TSK Gel ODS-100Z) that the purity (absorption intensity surface area ratio of 254 nm) was at least 99.9%.

Comparative Example 1

A glass substrate having an ITO film measuring 2.5 cm square and 0.5 min in thickness (made by Geomatec, surface resistance of 100Ω/□) was put into a washing vessel and ultrasonically washed in 2-propanol, after which it was subjected to UV-ozone processing, for 30 minutes. The following organic layers were successively deposited over this transparent anode (ITO film) by vacuum vapor deposition:

First layer: LG-101, film thickness of 10 nm
Second layer: NPD, film thickness of 30 nm
Third layer: comparative compound 2 and GD-1 (weight ratio of 90:10), film thickness of 30 nm
Fourth layer: comparative compound 1, film thickness of 10 nm
Fifth layer: Alq, film thickness of 40 nm Over this, 0.1 nm of lithium fluoride and 200 nm of metallic aluminum were vapor deposited in that order to form a cathode.

Without coming into contact with the air, this laminate was put into a glove box that had been replaced with nitrogen gas, and sealed with a glass sealing jar and a UV-setting adhesive (XNR5516HV, made by Nagase Chiba[5]), which gave the element of Comparative Example 1.

[5] Translator's note: "Nagase Chiba" is a predecessor of "Nagase ChemteX"

Working Examples 1 to 5 and Comparative Examples 2 to 4

Other than using compounds 1-1, 1-2, 1-4, 1-8, and 1-58 of the present case and comparative compounds 2 to 4 instead of comparative compound 1 as the material of the fourth layer in Comparative Example 1, the elements of Working Examples 1 to 5 and Comparative Examples 2 to 4 were obtained in the same manner as in Comparative Example 1.

These elements were evaluated in terms of efficiency, durability, and drive voltage by the following methods, the results of which are given in Table 1.

(a) Efficiency

DC voltage was applied to each element using a Source Measure Unit 2400 made by Toyo Corporation, and the brightness of the emitted light was measured using a BM-8 luminance meter made by Topcon. The emission spectrum and the emission wavelength were measured using, a PMA-11 spectral analyzer made by Hamamatsu Photonics. On the basis of these [results], the external quantum efficiency near 1000 cd/m$^2$ was calculated by brightness conversion method.

[The results] are shown in Table 1, with ○ indicating that the external quantum efficiency was at least 12%. Δ at least 7% and less than 12%, and x less than 7%.

(b) Durability

DC voltage was applied to each element such that it continuously emitted light at a brightness of 5000 cd/m$^2$ at room temperature, and how long it took for the brightness to drop to 4000 cd/m$^2$ was used as an index of durability. [The results] are shown in Table 1, with ⊚ indicating at least 800 hours, ○ at least 700 hours and less than 800 hours, Δ at least 200 hours and less than 700 hours, and x less than 200 hours.

(c) Drive Voltage

DC voltage was applied to each element such that it emitted light at a brightness of 1000 cd/m$^2$. The applied voltage at this point was used as an index of drive voltage evaluation, [The results] are shown in Table 1, with ○ indicating that the drive voltage was less than 8 V, Δ at least 8 V and less than 9 V, and x at least 9 V.

TABLE 1

|  | Compound | Efficiency | Durability | Drive voltage |
| --- | --- | --- | --- | --- |
| Working Example 1 | compound 1-1 | ○ | ○ | ○ |
| Working Example 2 | compound 1-2 | ○ | ⊚ | ○ |
| Working Example 3 | compound 1-4 | ○ | ○ | ○ |
| Working Example 4 | compound 1-8 | ○ | ○ | ○ |
| Working Example 5 | compound 1-58 | ○ | ○ | ○ |
| Comparative Example 1 | comparative compound 1 | ○ | X | ○ |
| Comparative Example 2 | comparative compound 2 | ○ | Δ | ○ |
| Comparative Example 3 | comparative compound 3 | X | — | — |
| Comparative Example 4 | comparative compound 4 | ○ | Δ | ○ |

Note that in Comparative Example 3, efficiency was low, and not enough light was emitted to evaluate durability and drive voltage, making measurement impossible.

Working Examples 6 to 13 and Comparative Examples 5 to 8

The first layer in Working Example 1 was changed to GD-1, the GD-1 of the third layer was changed to the following red-light-emitting material (iridium complex A), the comparative compound 2 of the third layer was changed to the compound listed in the following table, and the following Balq was used as the material of the fourth layer. Other than that, the elements of Working Examples 6 to 13 and Comparative Examples 5 to 8 were produced in the same manner as in Working Example 1 and were evaluated in terms of efficiency and drive voltage by the same procedure as in Working Example 1.

Note that for the external quantum efficiency, [the results] are shown in Table 2, with ⊙ indicating when it was at least 13.5%, Δ at least 12% and less than 13.5%, and x less than 12%.

For the drive voltage, [the results] are shown in Table 2, with ○ indicating when it was less than 8 V, Δ at least 8 V and less than 8.5 V, and x at least 8.5 V.

DC voltage was applied to each element such that it continuously emitted light at a brightness of 3000 cd/m² at room temperature, and how long it took for the brightness to drop to 2500 cd/m² was used as an index of durability. [The results] are shown in Table 2, with ⊚ indicating at least 100 hours, ○ at least 70 hours and less than 100 hours, Δ at least 50 hours and less than 70 hours, and x less than 50 hours.

TABLE 2

|  | Compound | Efficiency | Durability | Drive voltage |
| --- | --- | --- | --- | --- |
| Working Example 6 | compound 1-1 | ○ | ○ | ○ |
| Working Example 7 | compound 1-2 | ○ | ⊚ | ○ |
| Working Example 8 | compound 1-4 | ○ | ⊚ | ○ |
| Working Example 9 | compound 1-5 | ○ | ○ | ○ |
| Working Example 10 | compound 1-6 | ○ | ⊚ | ○ |
| Working Example 11 | compound 1-7 | ○ | ⊚ | ○ |
| Working Example 12 | compound 1-8 | ○ | ⊚ | ○ |
| Working Example 13 | compound 1-58 | ○ | ○ | ○ |
| Comparative Example 5 | comparative compound 1 | Δ | Δ | X |
| Comparative Example 6 | comparative compound 2 | Δ | Δ | X |
| Comparative Example 7 | comparative compound 3 | X | — | — |
| Comparative Example 8 | comparative compound 4 | Δ | Δ | Δ |

Note that in Comparative Example 7, efficiency was low, and not enough light was emitted to evaluate durability and drive voltage, making measurement impossible.

It was found that using the compound of the present invention yielded an excellent element that had high efficiency, low drive voltage, and also excellent durability. In particular, with a green-light-emitting element, the durability was excellent when [the compound was] used as an intermediate layer between the light-emitting layer and the electron transport layer, and with a red-light-emitting element, efficiency and drive voltage were excellent when [the compound was] used as the host material for the light-emitting layer.

With a light-emitting device, display device, or lighting device, each of the pixels must instantly emit bright light through a high current density, and since the light-emitting element of the present invention is designed for high luminous efficiency in such cases, it can be used advantageously.

In addition, the element of the present invention has excellent luminous efficiency and durability when used in high-temperature environments, such as when installed in a vehicle, making it favorable for a light-emitting device, display device, or lighting device.

The structures of compounds other than the comparative compounds and compounds discussed above and used in Working Examples 1 to 13 and Comparative Examples 1 to 8 are shown below.

[Sixty-Sixth Chemical Formula]

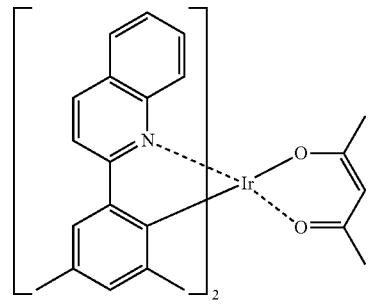

iridium complex A

-continued

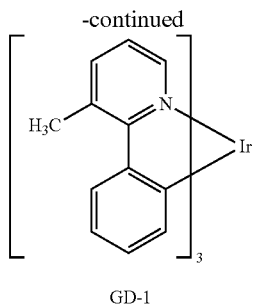

GD-1

-continued

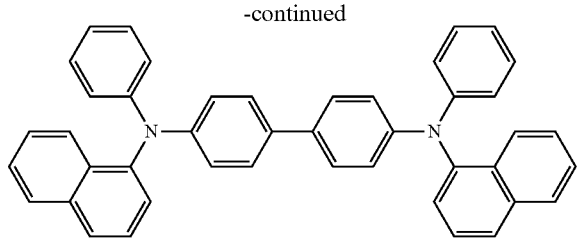

NPD

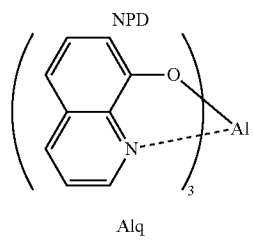

Alq

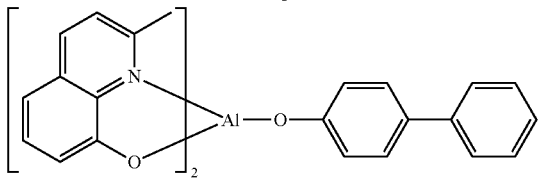

Balq

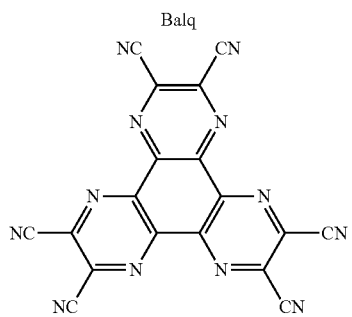

LG-101

INDUSTRIAL APPLICABILITY

With the present invention, it is possible to provide an organic electroluminescent element that has high efficiency, good durability, and low drive voltage.

The present invention was described in detail and by referring to a specific embodiment, but it will be clear to a person skilled in the art that various modifications and changes can be without departing from the sprit and scope of the present invention.

The present application is based on a Japanese patent application filed on Jul. 30, 2010 (Japanese Patent Application 2010-173184), and the content thereof is hereby incorporated as a reference.

DESCRIPTION OF SYMBOLS 2 substrate
3 anode
4 hole injection layer
5 hole transport layer
6 light-emitting layer
7 hole blocking layer
8 electron transport layer
9 cathode
10 organic electroluminescent element (organic EL element)
11 organic layer
12 protective layer
14 adhesive layer
16 sealing container
20 light-emitting device
30 light scattering member
30A light incidence face
30B light emission face
31 transparent substrate
32 micro particles
40 lighting device

The invention claimed is:

1. An organic electroluminescent element having on a substrate a pair of electrodes comprising an anode and a cathode and at least one organic layer including a light-emitting layer between these electrodes, wherein at least one layer out of said at least one organic layer contains at least one type of compound expressed by General Formula 1 below:

General Formula 1

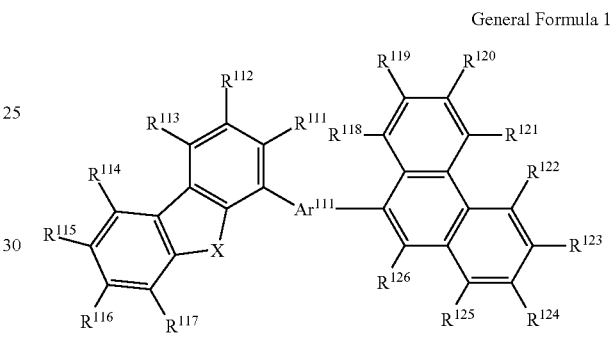

wherein X represents an oxygen atom or a sulfur atom, $R^{111}$ to $R_{126}$ represent each independently a hydrogen atom or a substituent, and $Ar^{111}$ is represented by one of General Formulae (1-3) to (1-5) below:

(1-3)

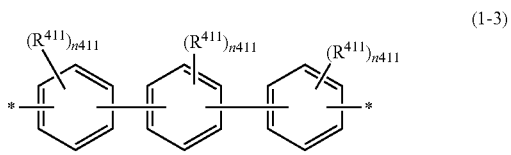

(1-4)

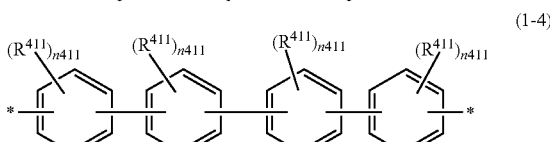

(1-5)

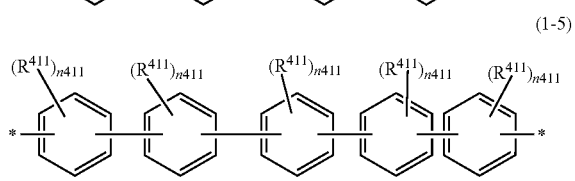

wherein each occurrence of $R^{411}$ independently represents hydrogen or a substituent, with the proviso that two or more of the substituents expressed by $R^{411}$ cannot together form a condensed aromatic ring, and
each occurrence of n411 independently represents an integer from 0 to 4.

2. The organic electroluminescent element according to claim 1, wherein the compound expressed by General Formula 1 above is a compound expressed by General Formula 3 below:

General Formula 3

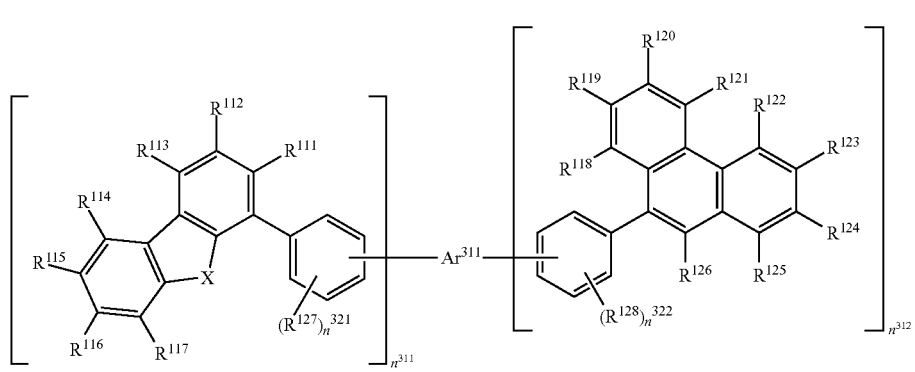

wherein, X represents an Oxygen atom or a sulfur atom, $R^{111}$ to $R^{126}$ represent each independently a hydrogen atom or a substituent, $R^{121}$ and $R^{122}$ do not form a condensed aromatic ring, $R^{127}$ and $R^{128}$ represent each independently a substituent, $n^{311}$ and $n^{312}$ represent each independently 1 or 2, $n^{321}$ and $n^{322}$ represent each independently an integer from 0 to 4, and $Ar^{311}$ is represented by one of General Formula (1-1) to (1-3) below:

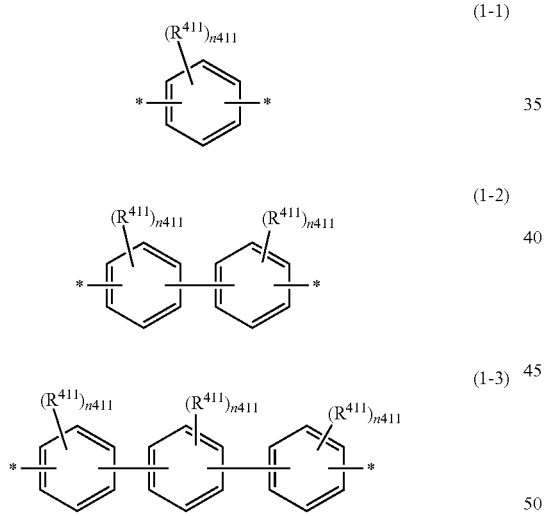

wherein each occurrence of $R^{411}$ independently represents hydrogen or a substituent, and each occurrence of n411 independently represents an integer from 0 to 4.

3. The organic electroluminescent element according to claim 1, wherein said light-emitting layer contains a compound expressed by General Formula 1 above.

4. The organic electroluminescent element according to claim 1, wherein said light-emitting layer contains an iridium complex.

5. The organic electroluminescent element according to claim 1, wherein said light-emitting layer contains an iridium complex expressed by General Formula T-1 below:

(T-1)

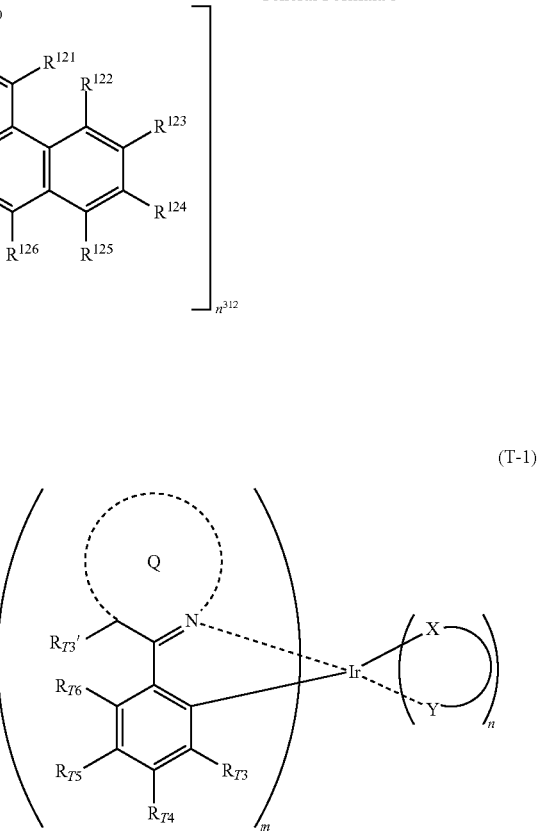

wherein, each of $R_{T3}'$, $R_{T3}$, $R_{T4}$, $R_{T5}$, and $R_{T6}$ independently represents a hydrogen atom or a substituent;

any adjacent two of $R_{T3}$, $R_{T4}$, $R_{T5}$, and $R_{T6}$, may bind together to form a condensed four- to seven-member ring, said condensed four- to seven-member ring is a cycloalkyl, an aryl, or a heteroaryl, and said condensed four- to seven-member ring may further have a substituent;

$R_{T3}'$ and $R_{T6}$ may form a ring by being linked by a linking group selected from among —C(R$_T$)$_2$—C(R$_T$)$_2$—, —CR$_T$=CR$_T$—, —C(R$_T$)$_2$—, —O—, —NR$_T$—, —O—C(R$_T$)$_2$—, —NR$_T$—C(R$_T$)$_2$—, and —N=CR$_T$—, and each occurrence of R$_T$ independently represents a hydrogen atom, an alkyl group, an alkenyl group, an alkynyl group; an aryl group, or a heteroaryl group, and may further have a substituent;

the ring Q is a five- or six-member aromatic heterocycle or condensed aromatic heterocycle including at least one nitrogen; and (X—Y) represents an auxiliary ligand, m is an integer of 1 to 3, n is an integer of 0 to 2, and m+n=3.

6. The organic electroluminescent element according claim 1, wherein there is an electron transport layer between said light-emitting layer and said cathode, there is an intermediate layer between this electron transport layer and said light-emitting layer, and this intermediate layer contains a compound expressed by General Formula 1 above.

7. A compound expressed by General Formula 3:

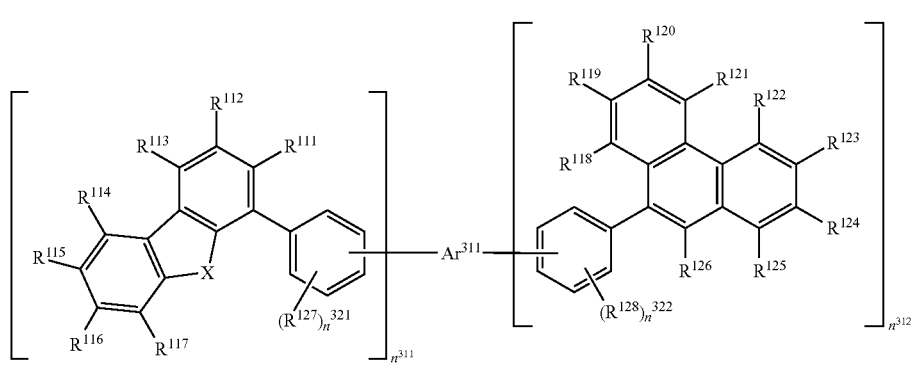

General Formula 3

X represents an oxygen atom or a sulfur atom, $R^{111}$ to $R^{126}$ represent each independently a hydrogen atom or a substituent, $R^{121}$ and $R^{122}$ do not form a condensed aromatic ring, $R^{127}$ and $R^{128}$ represent each independently a substituent, $n^{311}$ and $n^{312}$ represent each independently 1 or 2, $n^{321}$ and $n^{322}$ represent each independently an integer from 0 to 4, and $Ar^{311}$ is represented by or one of General Formula (1-1) to (1-3) below:

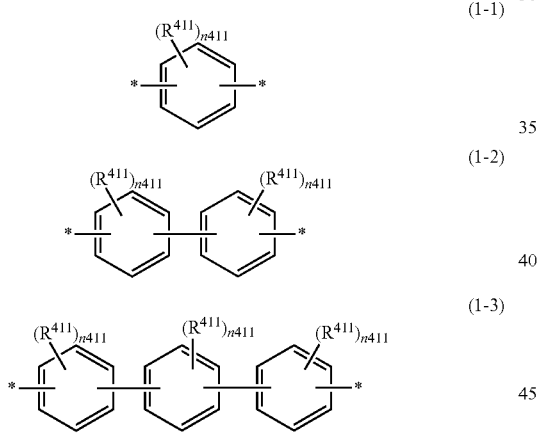

wherein each occurrence of $R^{411}$ independently represents hydrogen or a substituent, with the proviso that two or more of the substituents expressed by $R^{411}$ cannot together form a condensed aromatic ring, and each occurrence of n411 independently represents an integer from 0 to 4.

8. A composition, containing the compound expressed by General Formula 1 above according to claim 1.

9. A thin film, containing the compound expressed by General Formula 1 above according to claim 1.

10. A light-emitting device featuring the organic electroluminescent element according to claim 1.

11. A display device featuring the organic electroluminescent element according to claim 1.

12. A lighting device featuring the organic electroluminescent element according to claim 1.

13. A compound expressed by General Formula 1

General Formula 1

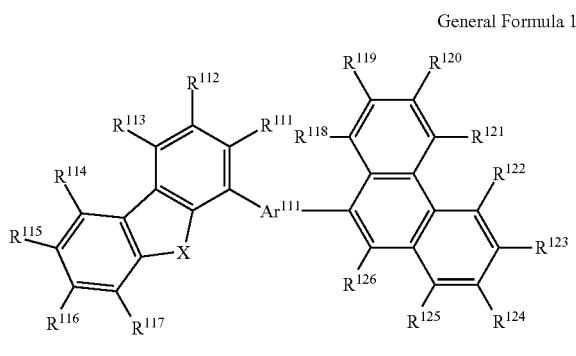

wherein X represents an oxygen atom or a sulfur atom, $R^{111}$ to $R^{126}$ represent each independently a hydrogen atom or a substituent, and $Ar^{111}$ is represented by one of General Formulae (1-3) to (1-5) below:

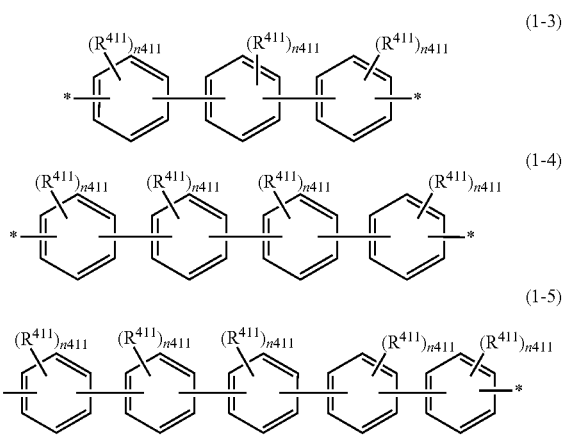

wherein each occurrence of $R^{411}$ independently represents hydrogen or a substituent, with the proviso that two or more of the substituents expressed by $R^{411}$ cannot together form a condensed aromatic ring, and each occurrence of n411 independently represents an integer from 0 to 4.

* * * * *